United States Patent
Chelliah et al.

(10) Patent No.: US 8,609,676 B2
(45) Date of Patent: Dec. 17, 2013

(54) 4, 5, 6-TRISUBSTITUTED PYRIMIDINE DERIVATIVES AS FACTOR IXA INHIBITORS

(75) Inventors: Mariappan V. Chelliah, Edison, NJ (US); Samuel Chackalamannil, Califon, NJ (US); William J. Greenlee, Teaneck, NJ (US); Keith Eagan, Kenilworth, NJ (US); Zhuyan Guo, Scotch Plains, NJ (US); Martin C. Clasby, Plainsboro, NJ (US); Yan Xia, Edison, NJ (US); Charles L. Jayne, Staten Island, NY (US); Michael Dwyer, Scotch Plains, NJ (US); Kartik M. Keertikar, East Windsor, NJ (US); Tin-Yau Chan, Edison, NJ (US); Li Wang, Nanuet, NY (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 0 days.

(21) Appl. No.: 13/388,628

(22) PCT Filed: Aug. 3, 2010

(86) PCT No.: PCT/US2010/044208
§ 371 (c)(1),
(2), (4) Date: Feb. 2, 2012

(87) PCT Pub. No.: WO2011/017296
PCT Pub. Date: Feb. 10, 2011

(65) Prior Publication Data
US 2012/0136016 A1    May 31, 2012

Related U.S. Application Data

(60) Provisional application No. 61/231,070, filed on Aug. 4, 2009.

(51) Int. Cl.
*A01N 43/54* (2006.01)
*A61K 31/505* (2006.01)

(52) U.S. Cl.
USPC .......................................... 514/269; 544/298

(58) Field of Classification Search
USPC .................. 544/319, 326, 328; 514/256, 259
See application file for complete search history.

(56) References Cited

U.S. PATENT DOCUMENTS

| | | | | |
|---|---|---|---|---|
| 4,824,851 | A * | 4/1989 | Takaya et al. | 514/274 |
| 7,211,673 | B2 * | 5/2007 | Hoffmann et al. | 546/275.4 |
| 2011/0212938 | A1 * | 9/2011 | Xia et al. | 514/210.18 |
| 2011/0263624 | A1 * | 10/2011 | Harris et al. | 514/269 |
| 2012/0040975 | A1 * | 2/2012 | Neelamkavil et al. | 514/230.5 |

FOREIGN PATENT DOCUMENTS

| | | |
|---|---|---|
| WO | WO 2004/046133 A1 | 6/2004 |
| WO | WO 2004046133 A1 * | 6/2004 |
| WO | WO2005/047279 A1 | 5/2005 |
| WO | WO 2005079798 A1 * | 9/2005 |
| WO | WO 2007073497 A2 * | 6/2007 |
| WO | WO2009/051822 A1 | 4/2009 |
| WO | WO 2009051119 A1 * | 4/2009 |
| WO | WO 2009055331 A2 * | 4/2009 |

OTHER PUBLICATIONS

PCT/US2010/044208, International Report on Patentability (Feb. 7, 2012).*
The Condensed Chemical Dictionary 822 (Gessner G. Hawley ed., 9th ed., 1977).*
Concise Chemical and Technical Dictionary 1081 (H. Bennett ed., 4th ed., 1986).*
Hawley's Condensed Chemical Dictionary 1186 (Richard J. Lewis, Sr. ed., 15th ed., 2007).*
Vijaykumar, D. et al.: "Discovery of novel hydroxy pyrazole based factor IXa Inhibitor" Bioorganic & Medicinal Chemistry Letters, Pergamon, Elsevier Science, GB LNKDDOI:10.1016/J.BMCL. 2006.01.123, vol. 16, No. 10, May 15, 2006, pp. 2796-2799, XP025106845; ISSN: 0960-894X.
International Search Report for PCT/US2010/044208; Performed by Authorized Officer: Dieter FINK; Completed by the European Patent Office on: Sep. 27, 2010.

* cited by examiner

*Primary Examiner* — James O Wilson
*Assistant Examiner* — Alexander R Pagano
(74) *Attorney, Agent, or Firm* — Richard S. Parr; Catherine D. Fitch

(57) ABSTRACT

The present invention relates to novel heterocyclic compounds of Formulae (I): (Chemical formula should be inserted here as it appears on abstract in paper form) Formula (I) as disclosed herein, or a pharmaceutically acceptable salt, solvate, ester, prodrug or stereoisomer thereof. Also disclosed are pharmaceutical compositions comprising said compounds, and methods for using said compounds for treating or preventing a thromboembolic disorder.

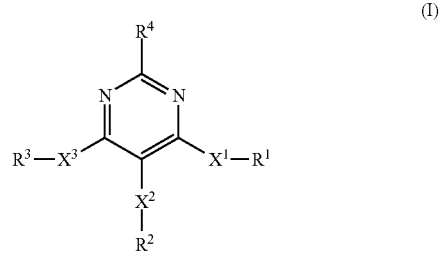

12 Claims, No Drawings

4, 5, 6-TRISUBSTITUTED PYRIMIDINE DERIVATIVES AS FACTOR IXA INHIBITORS

FIELD OF THE INVENTION

The present invention relates to heterocyclic compounds useful as serine protease inhibitors, regulators or modulators, in particular, serine protease enzymes of the coagulation cascade and/or contact activation system; for example thrombin, factor XIa, factor Xa, factor IXa, factor VIIa, and/or plasma kallikrein. In particular, it relates to compounds that are selective factor IXa inhibitors, pharmaceutical compositions comprising the compounds, and methods of treatment using the compounds and compositions to treat various thromboembolic disorders, such as acute coronary syndrome, atrial fibrillation, myocardial infarction, and atherosclerosis.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation involves three distinct phases: initiation, priming and propagation.[1,2,3] Initiation involves binding of tissue factor (TF) to activated factor VII, a circulating coagulation factor. Blood, in general is not exposed to TF which is a transmembrane protein expressed on extravascular cells. Vasular injury causes the TF-bearing cells to be exposed to blood, and initiates the coagulation process.[1]

The TF/VIIa complex activates factors IX and X.[1,4] Factor IXa is relatively unstable in plasma and diffuses toward activated platelets. Factor Xa on the other hand, is unstable in plasma and is rapidly inhibited by TF pathway inhibitor and antithrombin III.[1,5,6] Factor Xa binds factor Va on the surface of TF-bearing cells.[1,7] In turn, the Xa/Va complex generates a small but sufficient amount of thrombin to cause platelet activation.[1,8,9]

Thrombin activates platelets and coagulation factors in the priming phase.[1,2] Thrombin binds and cleaves platelet protease-activated receptors (PAR1 and PAR4), triggering a signaling cascade that catalyzes platelet activation and release of factor V from platelet a granules. Thrombin also activates factors V, VIII, and XI.[1]

It is during the propagation phase that thrombin generation is maximized on the surface of platelets. The primed, activated platelets bind the IXa/VIIIa "tenase" complex. Additional IXa is generated by factor XIa on the platelet surface.[10] The IXa/VIIIa complex, in physical proximity to Va, recruits factor X to the platelet surface for activation. The Xa/Va complex on the platelet surface is protected from TF pathway inhibitor and antithrombin III.[11,12]

Enzymology studies have shown that activation of factor X by IXa/VIIIa is nearly 50× more efficient than activation by factor VIIa/TF.[13] The platelet Xa/Va complex generates a "burst" of thrombin, resulting in a stable fibrin-platelet clot.[1]

The cell-based model of coagulation highlights the importance of the IXa/VIIIa complex in clot formation. Factor IXa therefore represents an excellent target for anticoagulant therapy.[1] There is a need for effective inhibitors of factor IXa in order to treat or prevent thromboembolic disorders.

Vijaykumar et al., *Biorganic & Medicinal Chemistry Letters* (2006), 16 (10), 2796-2799, discloses hydroxy pyrazole based factor IXa inhibitors.

REFERENCES CITED

1. Howard, E L, Becker K C, Rusconi, C P, Becker R C. Factor IXa Inhibitors as Novel Anticoagulents. *Arterioscler Thromb Vasc Biol.* 2007; 27: 722-727.
2. Monroe D M, Hoffman M, Roberts H R. Platelets and thrombin generation. *Arterioscler Thromb Vasc Biol.* 2002; 22: 1381-1389.
3. Ahmad S S, London F S, Walsh P N. The assembly of the factor X-activating complex on activated human platelets. *J Thromb Haemost.* 2003; 1: 48-59.
4. Komiyama Y, Pedersen A H, Kisiel W. Proteolytic activation of human factors IX and X by recombinant human factor VIIa: effects of calcium, phospholipids, and tissue factor. *Biochemistry.* 1990; 29: 9418-9425.
5. Broze G J, Warren L A, Novotny W F, Higuchi D A, Girard J J, Miletich P J. The lipoprotein-associated coagulation inhibitor that inhibits the factor VII-tissue factor complex also inhibits factor Xa: insight into its possible mechanism of action. *Blood.* 1988; 71: 335-343.
6. Rapaport S I. The extrinsic pathway inhibitor: a regulator of tissue factor-dependent blood coagulation. *Thromb Haemost.* 1991; 66: 6-15.
7. Monkovic D D, Tracy P B. Activation of human factor V by factor Xa and thrombin. *Biochemistry.* 1990; 29: 1118-1128.
8. Hoffman M, Monroe D M, Oliver J A, Roberts H R. Factors IXa and Xa play distinct roles in tissue factor-dependent initiation of coagulation. *Blood.* 1995; 86: 1794-1801.
9. Monroe D M, Hoffman M, Roberts H R. Transmission of a procoagulant signal from tissue factor-bearing cells to platelets. *Blood Coagul Fibrinolysis.* 1996; 7: 459-464.
10. Walsh P N, Sinha D, Koshy A, Seaman F S, Bradford H. Functional characterization of platelet-bound factor XIa: retention of factor XIa activity on the platelet surface. *Blood.* 1986; 68: 225-230.
11. Franssen J, Salemink I, Willems G M, Wun T C, Hemker H C, Lindhout T. Prothrombinase is protected from inactivation by tissue factor pathway inhibitor: competition between prothrombin and inhibitor. *Biochem J.* 1997; 323: 33-37.
12. Rezaie A R. Prothrombin protects factor Xa in the prothrombinase complex from inhibition by the heparin-antithrombin complex. *Blood.* 2001; 97: 2308-2313.
13. Lawson J H, Mann K G. Cooperative activation of human factor IX by the human extrinsic pathway of blood coagulation. *J Biol. Chem.* 1991; 266: 11317-11327.

SUMMARY OF THE INVENTION

In its many embodiments, the present invention provides a novel class of heterocyclic compounds, pharmaceutical compositions comprising one or more said compounds, and methods for using said compounds for treating or preventing a thromboembolic disorder.

Accordingly, in one aspect, the present invention provides compounds of Formula (I):

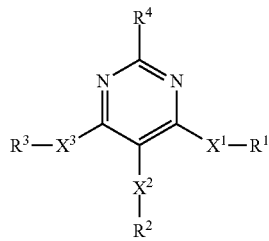

Formula (I)

or a pharmaceutically acceptable salt or solvate thereof, wherein:

$X^1$ is selected from the group consisting of a covalent bond, —S— and —O—;

$R^1$ is selected from the group consisting of halo, cycloalkyl, heterocyclyl, aryl and heteroaryl, wherein when each of said cycloalkyl, heterocyclyl, aryl and heteroaryl has substituents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substituents on adjacent carbon atoms, said substituents can optionally be taken together with the carbon atoms to which they are attached to form a second five- or six-membered cycloalkyl, heterocyclyl, aryl or heteroaryl;

$X^2$ is selected from the group consisting of a covalent bond, and —O—;

$R^2$ is selected from the group consisting of H, halogen and alkyl, with the proviso that when $X^2$ is a covalent bond, $R^2$ is halogen;

$X^3$ is selected from the group consisting of a covalent bond, —N(R)— and —O—;

R is H or alkyl;

$R^3$ is selected from the group consisting of halo, alkyl, cycloalkyl, aryl and heteroaryl, wherein when each of said cycloalkyl, heterocyclyl, aryl and heteroaryl has substituents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substituents on adjacent carbon atoms, said substituents can optionally be taken together with the carbon atoms to which they are attached to form a second five- or six-membered cycloalkyl, heterocyclyl, aryl or heteroaryl; and $R^4$ is selected from the group consisting of alkyl, cycloalkyl, heterocyclyl, aryl and heteroaryl;

with the proviso that when $X^1$ and $X^3$ are both —O—, then —$X^2$—$R^2$ is other than -halo.

In another aspect, the compounds of Formula I, or a pharmaceutically acceptable salt, solvate or ester thereof can be useful for treating or preventing a disorder or disease mediated by factor IXa, or a thromboembolic disorder (each disorder being a "Condition").

In another aspect, the present invention provides pharmaceutical compositions comprising at least one compound of Formula I or a pharmaceutically acceptable salt, solvate or ester thereof, and a pharmaceutically acceptable carrier. The compositions can be useful for treating or preventing a Condition.

In still another aspect, the present invention provides methods for treating a Condition, the method comprising administering to a patient an effective amount of at least one compound of Formula I, or a pharmaceutically acceptable salt, solvate or ester thereof.

DETAILED DESCRIPTION OF THE INVENTION

In an embodiment, the present invention provides at least one compound of Formula I or a pharmaceutically acceptable salt, solvate, ester or prodrug thereof. The compounds of formula I can be useful for treating or preventing a Condition in a patient.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heteroaryl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, heteroaryl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

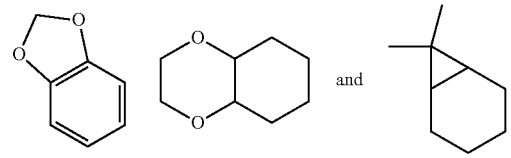

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

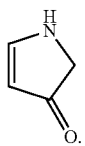

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

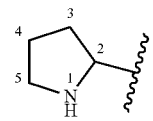

there is no —OH attached directly to carbons marked 2 and 5.

It should also be noted that tautomeric forms such as, for example, the moieties:

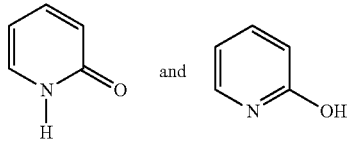 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan. In one embodiment, such purity means at least 95% pure, in another embodiment at lest 90% pure, in another embodiment at least 80% pure, in another embodiment at least 70% pure, and in another embodiment at least 60% pure.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis*, $4^{th}$ edition (2007), Wiley, New York.

When any variable (e.g., aryl, heterocycle, $R^2$, etc.) occurs more than one time in any constituent or in Formula I-VI, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$- $C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

The physical properties of some of the deuterated analogs described here can be significantly modified by substituting hydrogen with deuterium by employing reagents containing deuterium. This can lead to compounds with improved pharmacokinetic profiles. Three representative examples of possible method of preparation of deuterium containing analogs are presented below: Intermediate 2 can be reduced with Raney nickel under deuterium gas that will provide 3-D. Using sodiumborodeutiride, intermediate 77 can be reduced to provide analog 78-D. Similarly, P51 can be first converted to its imine and subsequently reduced with sodiumcyanoborodeuteride followed by debenzylation to give 80-D.

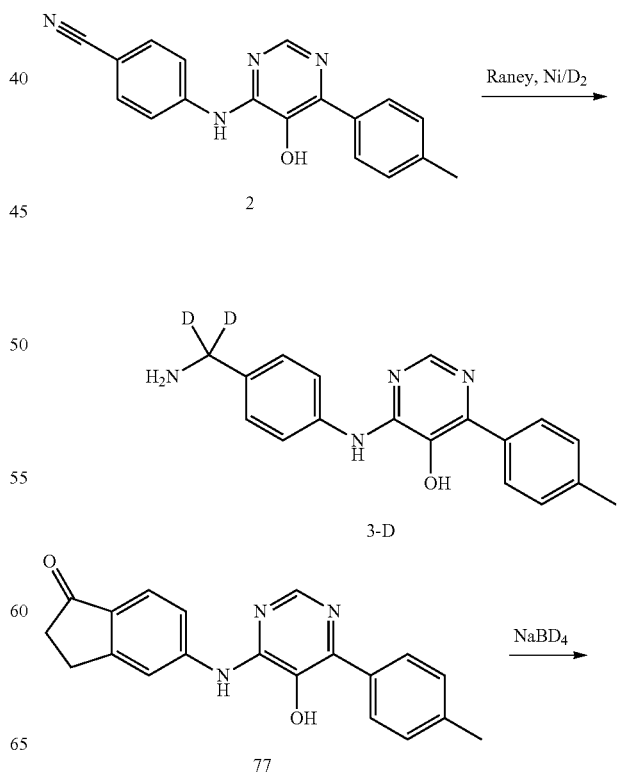

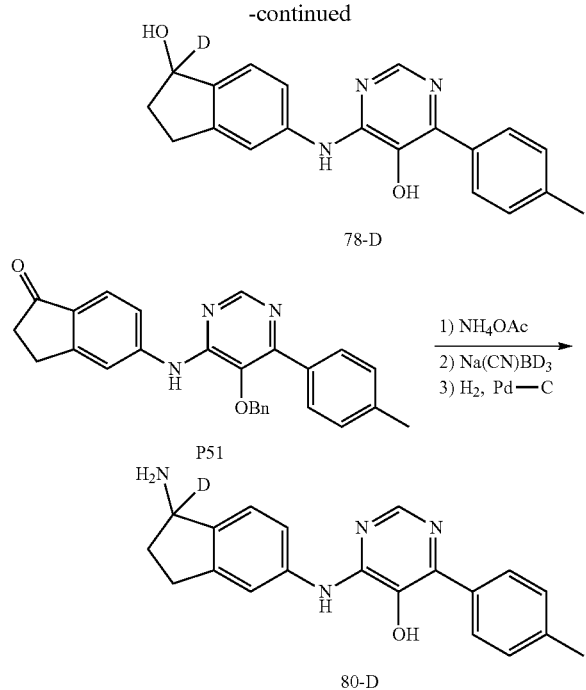

Polymorphic forms of the compounds of Formula I, and of the salts, solvates, esters and prodrugs of the compounds of Formula I, are intended to be included in the present invention.

Heterocyclic Compounds of the Invention the present invention provides compounds of Formula (I):

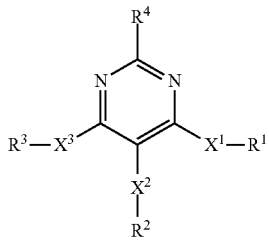

Formula (I)

or a pharmaceutically acceptable salt or solvate thereof, wherein:

$X^1$ is selected from the group consisting of a covalent bond, —S— and —O—;

$R^1$ is selected from the group consisting of halo, cycloalkyl, heterocyclyl, aryl and heteroaryl, wherein when each of said cycloalkyl, heterocyclyl, aryl and heteroaryl has substitutents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substitutents on adjacent carbon atoms, said substituents can optionally be taken together with the carbon atoms to which they are attached to form a second five- or six-membered cycloalkyl, heterocyclyl, aryl or heteroaryl;

$X^2$ is selected from the group consisting of a covalent bond, and —O—;

$R^2$ is selected from the group consisting of H, halogen and alkyl, with the proviso that when $X^2$ is a covalent bond, $R^2$ is halogen;

$X^3$ is selected from the group consisting of a covalent bond, —N(R)— and —O—;

R is H or alkyl;

$R^3$ is selected from the group consisting of halo, alkyl, cycloalkyl, heterocyclyl, aryl and heteroaryl, wherein when each of said cycloalkyl, heterocyclyl, aryl and heteroaryl has substitutents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substitutents on adjacent carbon atoms, said substituents can optionally be taken together with the carbon atoms to which they are attached to form a second five- or six-membered cycloalkyl, heterocyclyl, aryl or heteroaryl; and $R^4$ is selected from the group consisting of alkyl, cycloalkyl, heterocyclyl, aryl and heteroaryl;

with the proviso that when $X^1$ and $X^3$ are both —O—, then —$X^2$—$R^2$ is other than -halo.

In another embodiment, in Formula (I), $X^2$ is —O— and $R^2$ is H or alkyl.

In another embodiment, in Formula (I), $X^2$ is a covalent bond, and $R^2$ is halo.

In another embodiment, in Formula (I), —$X^2R^2$ is selected from the group consisting of hydroxyl, methoxy, and fluoro.

In another embodiment, in Formula (I), $X^1$ is selected from the group consisting of a covalent bond and —O—.

In another embodiment, in Formula (I), wherein $X^1$ is a covalent bond, and $R^1$ is halo.

In another embodiment, in Formula (I), $R^1$ aryl is phenyl which is unsubstituted or substituted with at least one ring system substituent.

In another embodiment, in Formula (I), $R^1$ aryl is phenyl which is unsubstituted or substituted with at least one ring system substituent, wherein the ring system substituent is selected from the group consisting of halo, alkyl, haloalkyl, haloalkoxy, —C(=O)OH, and —C(=NH)NH$_2$.

In another embodiment, in Formula (I), X is —O—, and $R^1$ is phenyl which is substituted with a ring system substituent selected from the group consisting of fluoro, chloro, trifluoromethyl, trifluoromethoxy, methyl, ethyl, and —C(=NH)NH$_2$.

In another embodiment, in Formula (I), $X^3$ is NH, and $R^3$ is selected from the group consisting of alkyl, cylcloalkyl, heterocyclyl, and aryl, wherein when each of said cycloalkyl, heterocyclyl, and aryl has substitutents on adjacent carbon atoms, said substituents can optionally be taken together with the carbon atoms to which they are attached to form a five- or six-membered aryl or heteroaryl.

In another embodiment, in Formula (I), $X^3$ is NH, and $R^3$ is alkyl which is unsubstituted or substituted with a substituent selected from the group consisting of aryl, wherein when said aryl has substitutents on adjacent carbon atoms, said substituents can optionally be taken together with the carbon atoms to which they are attached to form a five- or six-membered aryl or heteroaryl In another embodiment, in Formula (I), $X^3$ is NH, and $R^3$ is alkyl-benzopyridyl, wherein the benzopyridyl is attached to the alkyl through the benzene ring of said benzopyridyl, wherein said benzopyridyl is unsubstituted or substituted with a ring system substitutent.

In another embodiment, in Formula (I), $X^3$ is NH, and $R^3$ is alkyl-benzopyridyl, wherein the benzopyridyl is attached to the alkyl through the benzene ring of said benzopyridyl, wherein said benzopyridyl is unsubstituted or substituted with a ring system substitutent, wherein said ring system substituent is —NH$_2$.

In another embodiment, in Formula (I), X$^3$ is NH, and R$^3$ is cycloalkyl, wherein when said cycloalkyl has substitutents on adjacent carbon atoms, said substituents can optionally be taken together with the carbon atoms to which they are attached to form a five- or six-membered aryl or heteroaryl.

In another embodiment, in Formula (I), X$^3$ is NH, and R$^3$ is cycloalkyl, wherein when said cycloalkyl has substitutents on adjacent carbon atoms, said substituents can optionally be taken together with the carbon atoms to which they are attached to form a five- or six-membered aryl or heteroaryl, wherein said R$^3$ cycloalkyl, optionally with said five- or six-membered aryl or heteroaryl is unsubstituted or substituted with at least one ring system substituent.

In another embodiment, in Formula (I), X$^3$ is NH, and R$^3$ is cycloalkyl selected from the group consisting of cyclohexyl, and thiazolyl-fused cyclohexyl, each of which unsubstituted or substituted with a ring system substituent.

In another embodiment, in Formula (I), X$^3$ is NH, and R$^3$ is cycloalkyl selected from the group consisting of cyclohexyl, and thiazolyl-fused cyclohexyl, each of which unsubstituted or substituted with a ring system substituent, wherein the ring system substituent is selected from the group consisting of alkyl, —NH$_2$, aminoalkyl, -alkyl-NH—C(=O)O-alkyl, —NH—C(=O)O-alkyl.

In another embodiment, in Formula (I), X$^3$ is NH, and R$^3$ is heterocyclyl, wherein when said heterocyclyl has substitutents on adjacent carbon atoms, said substituents can optionally be taken together with the carbon atoms to which they are attached to form a five- or six-membered aryl or heteroaryl.

In another embodiment, in Formula (I), X$^3$ is NH, and R$^3$ is heterocyclyl, wherein when said heterocyclyl has substitutents on adjacent carbon atoms, said substituents can optionally be taken together with the carbon atoms to which they are attached to form a five- or six-membered aryl or heteroaryl, wherein said R$^3$ heterocyclyl, optionally with said five- or six-membered aryl or heteroaryl is unsubstituted or substituted with at least one ring system substituent.

In another embodiment, in Formula (I), X$^3$ is NH, and R$^3$ is piperidinyl which is unsubstituted or substituted with at least one ring system substituent.

In another embodiment, in Formula (I), X$^3$ is NH, and R$^3$ is piperidinyl which is unsubstituted or substituted with at least one ring system substituent,
wherein the ring system substituent is —C(=O)—O-alkyl.

In another embodiment, in Formula (I), X$^3$ is NH, and R$^3$ is aryl, wherein when said aryl has substitutents on adjacent carbon atoms, said substituents can optionally be taken together with the carbon atoms to which they are attached to form a five- or six-membered cyclohexyl, aryl, or heteroaryl.

In another embodiment, in Formula (I), X$^3$ is NH, and R$^3$ is aryl, wherein when said aryl has substitutents on adjacent carbon atoms, said substituents can optionally be taken together with the carbon atoms to which they are attached to form a five- or six-membered cyclohexyl, aryl, or heteroaryl, wherein said R$^3$ aryl, optionally with said five- or six-membered heteroaryl is unsubstituted or substituted with at least one ring system substituent.

In another embodiment, in Formula (I), X$^3$ is NH, and R$^3$ is aryl, wherein when said aryl has substitutents on adjacent carbon atoms, said substituents can optionally be taken together with the carbon atoms to which they are attached to form a five- or six-membered cyclohexyl, aryl, or heteroaryl, wherein said R$^3$ aryl is selected from the group consisting of phenyl,

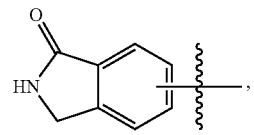

isoindolinyl, benzoimidazolyl, benzoxazolyl, benzopyrrolyl, benzopyrrazolyl,

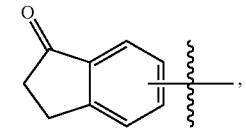

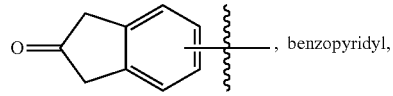, benzopyridyl,

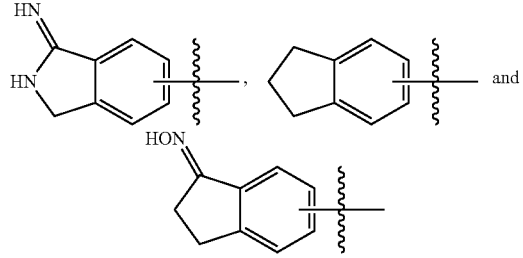 and

each of which is independently unsubstituted or substituted with at least one ring system substituent, and wherein

indicates the point of attachment of the R$^3$ aryl.

In another embodiment, in Formula (I), X$^3$ is NH, and R$^3$ is aryl, wherein when said aryl has substitutents on adjacent carbon atoms, said substituents can optionally be taken together with the carbon atoms to which they are attached to form a five- or six-membered cyclohexyl, aryl, or heteroaryl, wherein said R$^3$ aryl, optionally with said five- or six-membered heteroaryl is unsubstituted or substituted with at least one ring system substituent, wherein the ring system substituent is selected from the group consisting of alkyl, aminoalkyl, —NH$_2$, —C(=NH)NH$_2$, cyano, halo, —C(=O)O-alkyl, alkoxy, haloalkoxy, heteroaryl, hydroxyl, and —C(=O)NH$_2$.

In another embodiment, in Formula (I), X$^3$ is a covalent bond, and R$^3$ is heteroaryl, wherein when said heteroaryl has substitutents on adjacent carbon atoms, said substituents can optionally be taken together with the carbon atoms to which they are attached to form a five- or six-membered aryl or heteroaryl.

In another embodiment, in Formula (I), X$^3$ is a covalent bond, and R$^3$ is heteroaryl, wherein when said heteroaryl has substitutents on adjacent carbon atoms, said substituents can optionally be taken together with the carbon atoms to which they are attached to form a five- or six-membered aryl or heteroaryl, wherein said R³, optionally with said five- or six-membered aryl or heteroaryl, is unsubstituted or substituted with at least one ring system substituent.

In another embodiment, in Formula (I), X³ is a covalent bond, and R³ is heteroaryl, wherein when said heteroaryl has substitutents on adjacent carbon atoms, said substituents can optionally be taken together with the carbon atoms to which they are attached to form a five- or six-membered aryl or heteroaryl, wherein said R³, optionally with said five- or six-membered aryl or heteroaryl, is unsubstituted or substituted with at least one ring system substituent, wherein said R³ heteroaryl is benzopyrrolidinyl which is unsubstituted or substituted with at least one ring system substituent.

In another embodiment, in Formula (I), X³ is a covalent bond, and R³ is heteroaryl, wherein when said heteroaryl has substitutents on adjacent carbon atoms, said substituents can optionally be taken together with the carbon atoms to which they are attached to form a five- or six-membered aryl or heteroaryl, wherein said R³, optionally with said five- or six-membered aryl or heteroaryl, is unsubstituted or substituted with at least one ring system substituent, wherein the ring system substituent is selected from the group consisting of cyano, alkyl, and aminoalkyl-.

In another embodiment, in Formula (I), X³ is a covalent bond, and R³ is halo.

In another embodiment, in Formula (I), X¹ and X³ are both —O—, and R¹ and R³ are both H or aryl.

In another embodiment, in Formula (I), R⁴ is alkyl and is t-butyl.

In another embodiment, in Formula (I), R⁴ is cycloalkyl and is selected from the group consisting of cyclopropyl and cyclohexyl.

In another embodiment, in Formula (I), R⁴ is aryl and is phenyl.

In another embodiment, the compound of Formula (I) is selected from the group consisting of:

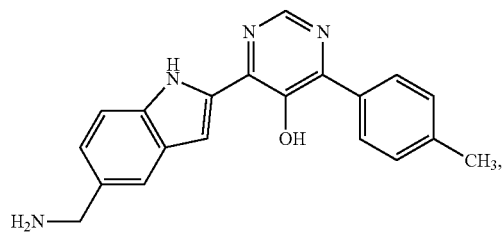

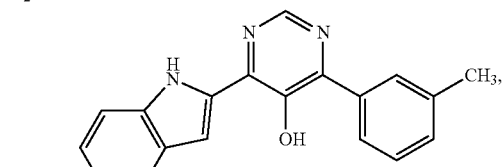

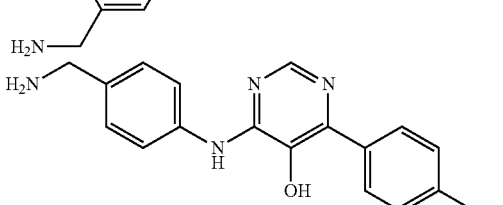

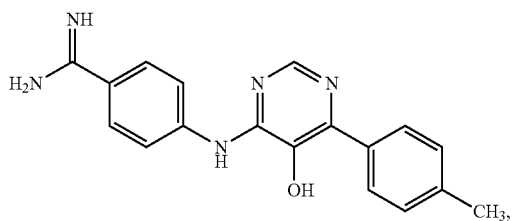

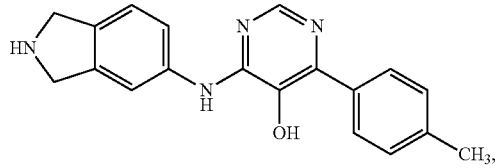

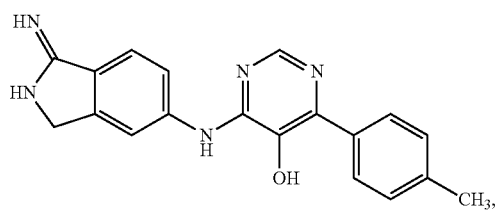

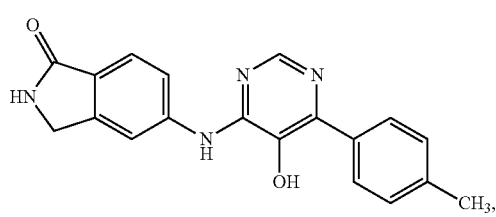

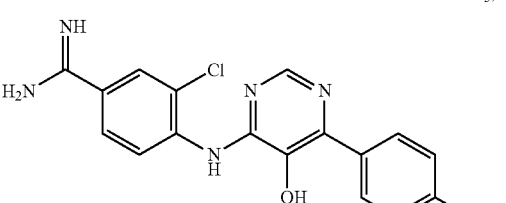

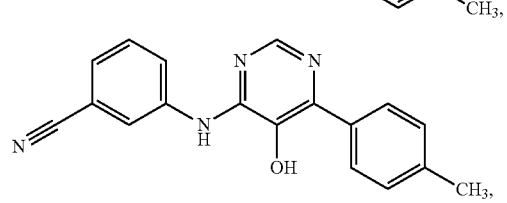

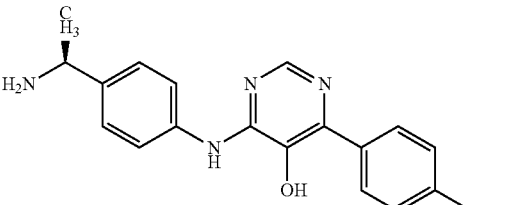

-continued
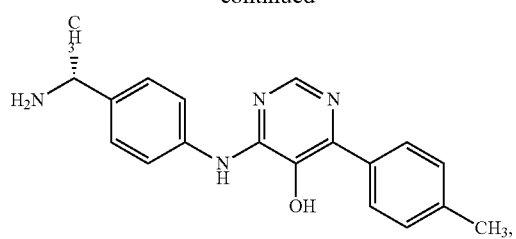
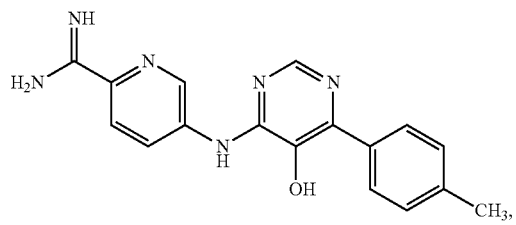
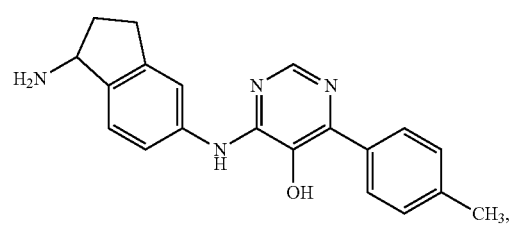
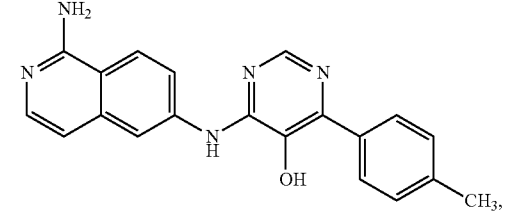
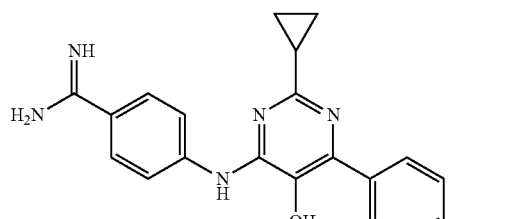
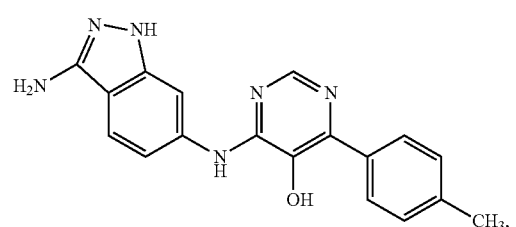
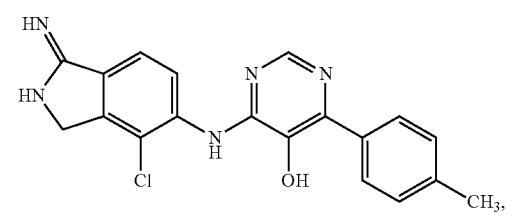
-continued
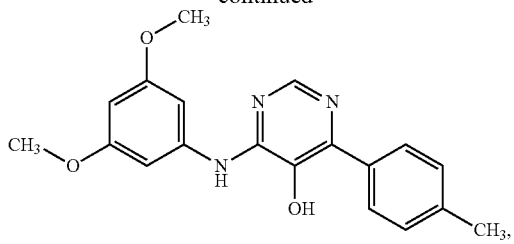
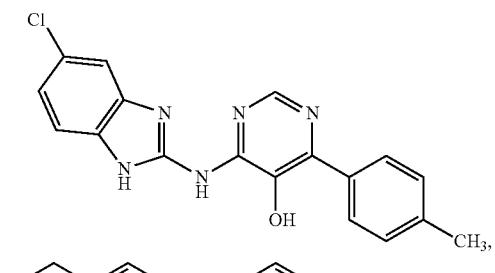
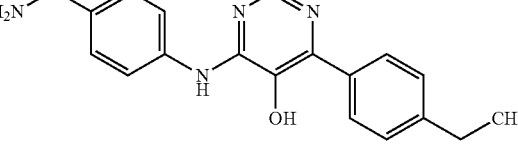
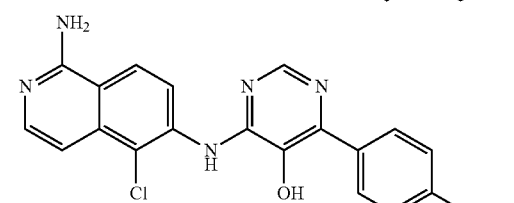
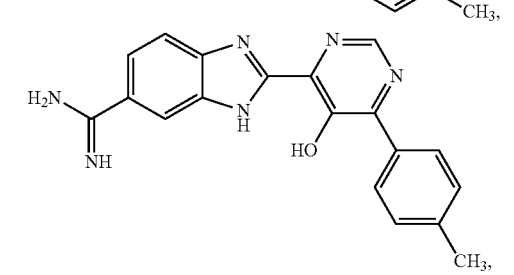
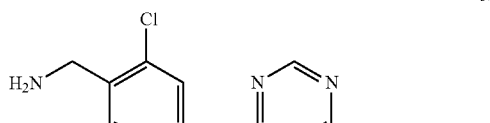
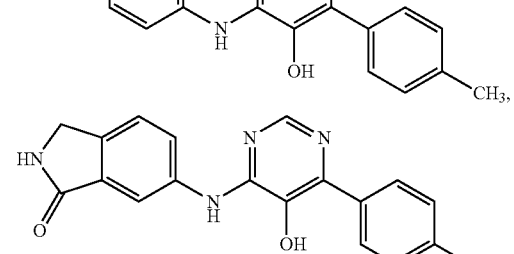
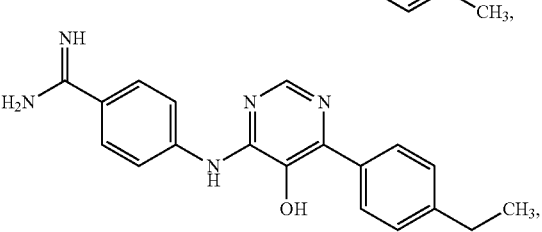

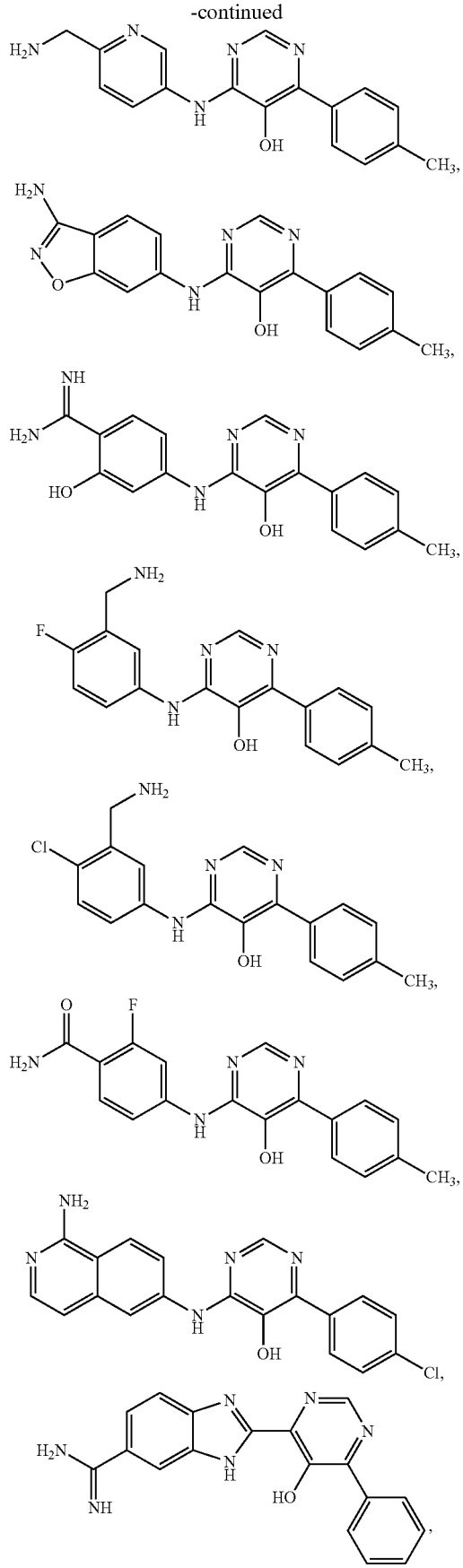
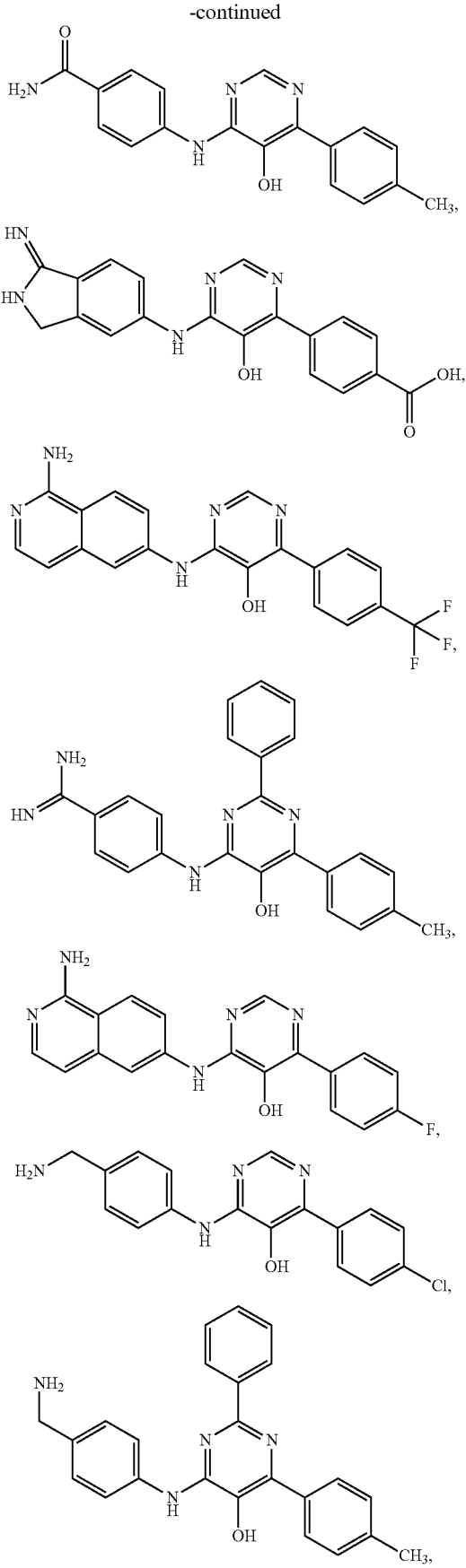

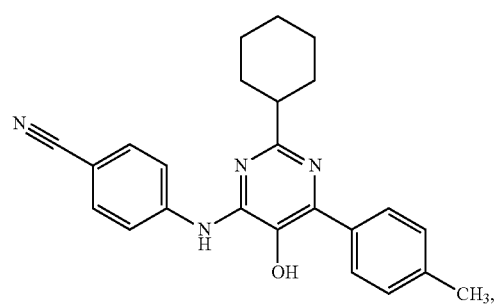
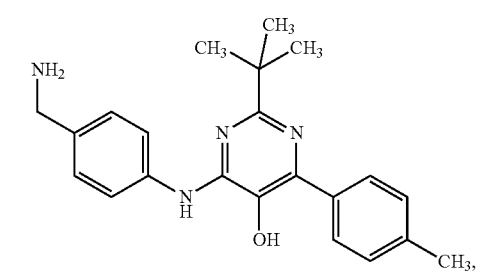
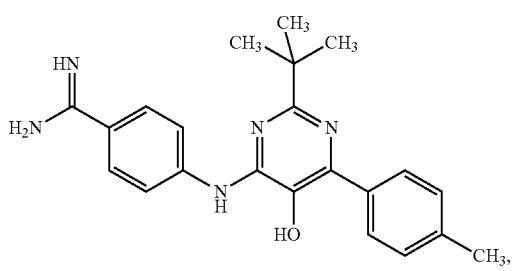
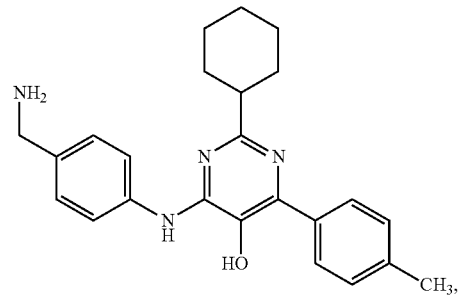
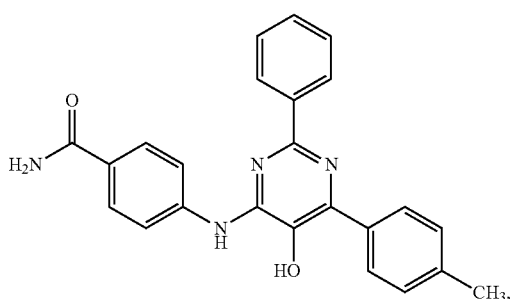
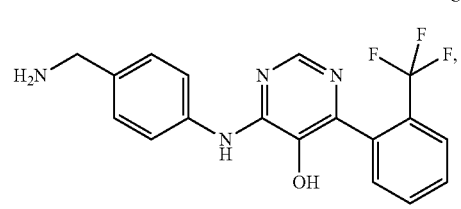
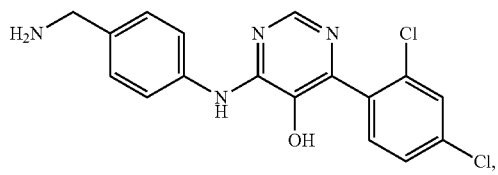
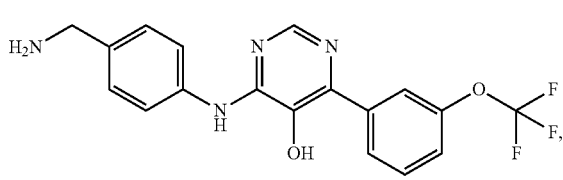
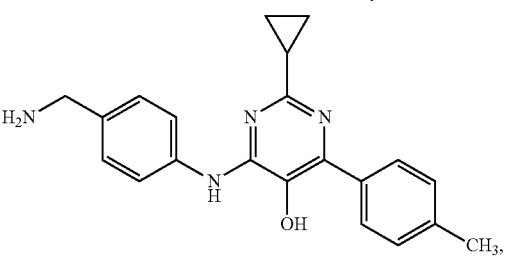
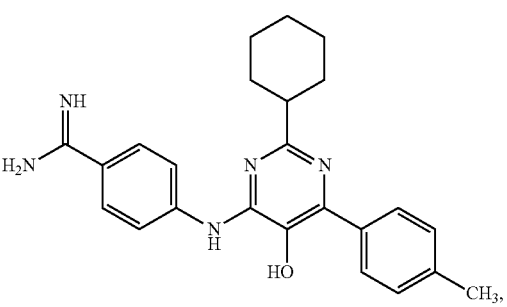
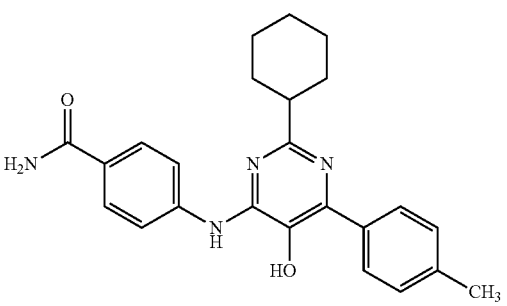
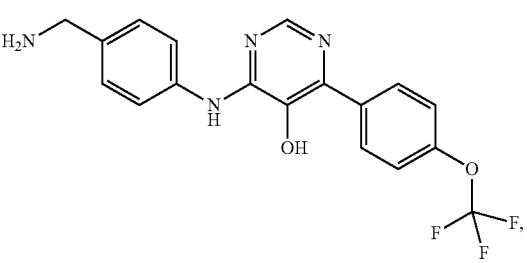
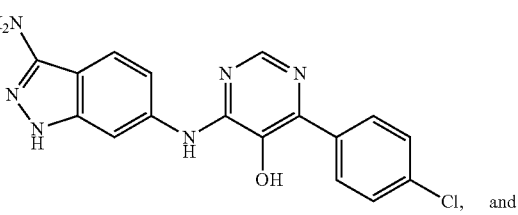

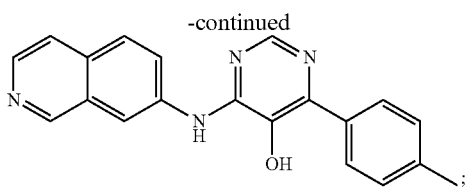

or a pharmaceutically acceptable salt or solvate thereof.

Methods for Making the Compounds of Present Invention

General Methods

ABBREVIATIONS USED

μW microwave
10% Pd(C) 10% palladium on carbon
Ac acetyl
AcOH acetic acid
$Ag_2CO_3$ silver carbonate
$BBr_3$ borontribromide
$BF_3.OEt_2$ borontrifluoride etherate
$BH_3.SMe_2$ borane dimethylsulfide complex
n-BuOH n-butanol
t-BuOH tert-butanol
t-BuOK potassium tert-butoxide
$CH_2Cl_2$ or DCM methylene chloride
$Cs_2CO_3$ cesium carbonate
DIPEA N,N-diisopropylethylamine
DME 1,2-dimethoxyethane
DMAP dimethylaminopyridine
DMF N,N-dimethylfomamide
DMSO dimethylsulfoxide
DPPA diphenylphosphonyl azide
EDCl 1-ethyl-3-(3-dimethylaminopropyl)carbodiimide
Et ethyl
$Et_3N$ triethylamine
EtOAc ethyl acetate
EtOH ethanol
$H_2O$ water
HATU 2-(1H-7-azabenzotriazol-1-yl)-1,1,3,3-tetramethyluronium hexafluorophosphate
HCl hydrogen chloride
HPLC high performance liquid chromatography
hr or h hour
KOH potassium hydroxide
LiOH lithium hydroxide
Me methyl
MeCN acetonitrile
MeOH methanol
MeI iodomethane
$MgSO_4$ magnesium sulfate
$NaHCO_3$ sodium bicarbonate
NaH sodium hydride
$NaN_3$ sodium azide
NaOAc sodium acetate
$Na_2CO_3$ sodium carbonate
NaOEt sodium ethoxide
$NH_4OAc$ ammonium acetate
$NH_3$ ammonia
$NH_4Cl$ ammonium chloride
$Pd_2(dba)_3$ tris(dibenzylideneacetone)dipalladium(0))
PhSNa sodium thiophenolate
PMB para-methoxybenzyl
RT or rt room temperature
SGC silca gel chromatography
TBAF tertabutylammonium fluoride
TBS tert-butyldimethylsilyl
TFA trifluoroacetic acid
THF tetrahydrofuran
TLC thin layer chromatography Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from $Me_4Si$ with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. MS data were obtained using Agilent Technologies LC/MSD SL or 1100 series LC/MSD mass spectrometer.

EXPERIMENTAL

Scheme A:

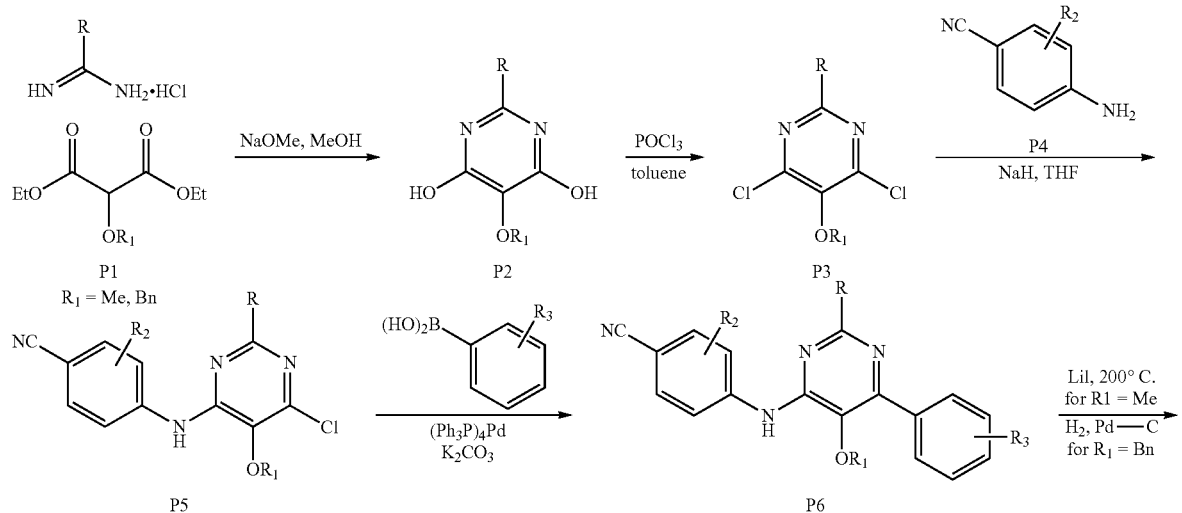

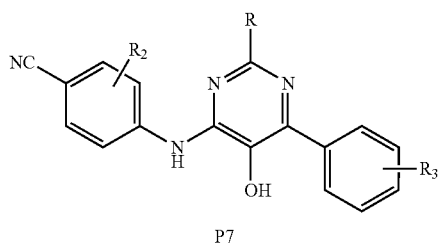

P7

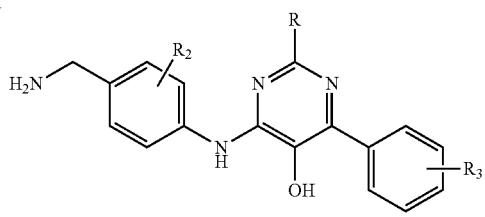

P8

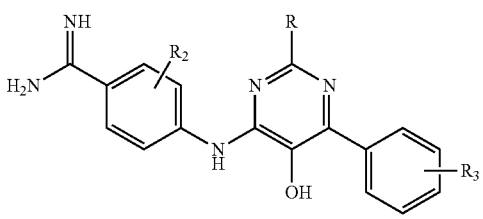

P9

Also:

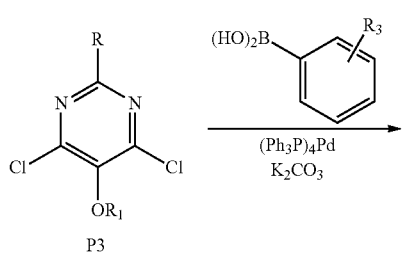

A general synthesis of compounds such as P6-P9 is described in scheme A. The synthesis starts with commercially available formamidines which on reaction with malonate P1 gave P2 which on subsequent treatment with POCl$_3$ gave P3. Aminobenzonitriles P4 can be reacted with P3 to give P5 which can be subjected to a Suzuki reaction to give P6. Deprotection of the phenolic ether can be achieved either using LiI at elevated temperature (for R$_1$=Me) of using H$_2$, Pd—C (for R$_1$=Bn). The nitrile group of P7 can be converted to benzylamine P8 and amidine P9. The intermediate P6 can also be synthesized via an alternate route as depicted in the scheme.

Dichloropyrimidine intermediate P3 can be subjected to a Suzuki reaction first to give P10 which can be coupled with aniline P4 either using NaH or using palladium mediated cross coupling reaction to give P6.

Example 1

4-[[5-Methoxy-6-(4-methylphenyl)-4-pyrimidinyl]amino]benzonitrile

Step 1

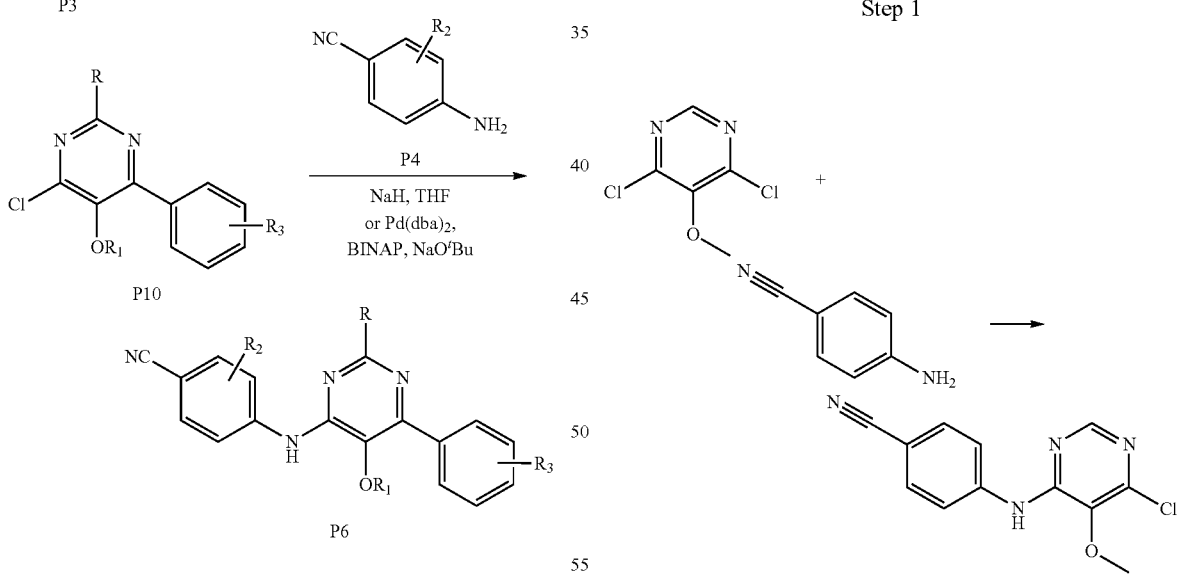

To 1 g of 4-aminobenzonitrile in 50 mL of dry THF at 0° C. was added 1.34 g of 60% sodium hydride in mineral oil and the mixture stirred under nitrogen for 10 minutes. 1.5 g of the 4,6-dichloro-5-methoxypyrimidine (commercially available) was then added and the mixture allowed warming to room temperature while stirring. After about 16 hours the reaction mixture was quenched with water then the mixture extracted three times with ethyl acetate. The combined extracts were washed with brine, dried with magnesium sulfate, filtered and evaporated to dryness yielding 2.73 g of a tan solid. The solid was triturated with diethyl ether and filtered yielding 1.73 g of the desired product.

Step 2

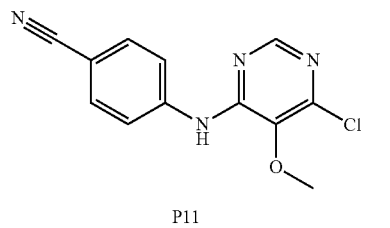

P11

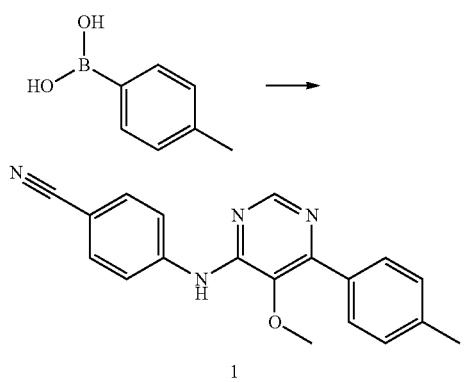

To 750 mg of P11 in 4 mL of toluene, 2 mL of water and 2 mL of DME was added 490 mg of p-tolylboronic acid, 1.19 g of potassium carbonate and 330 mg of tetrakis(triphenylphosphine)palladium. After bubbling with argon for 2 minutes the reaction mixture was heated to 100° C. for 16 hours in an oil bath. The reaction mixture was poured onto water and extracted three times with ethyl acetate. The combined extracts were washed with brine, dried with magnesium sulfate, filtered and evaporated to dryness. The residue was purified by flash chromatography yielding 210 mg of 1. LCMS: 317.4 (MH$^+$)

Example 2

4-[[5-Hydroxy-6-(4-methylphenyl)-4-pyrimidinyl]amino]benzonitrile

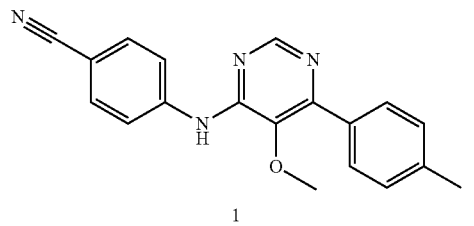

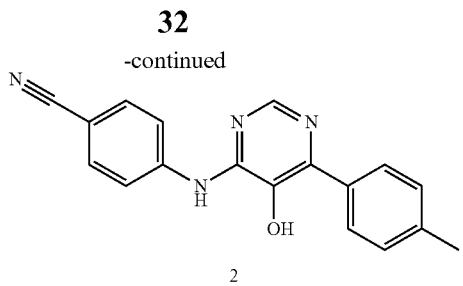

To 200 mg of 1 in 3 mL of quinoline was added 845 mg of lithium iodide and the mixture bubbled with argon for several minutes. The reaction mixture was sealed in a pressure tube and heated to 200° C. for 10 minutes using a microwave reactor. The residue, now solid at room temperature, was purified by flash chromatography yielding 232 mg of 2. LCMS: 303.2 (MH$^+$)

Example 3

4-[[4-(Aminomethyl)phenyl]amino]-6-(4-methylphenyl)-5-pyrimidinol

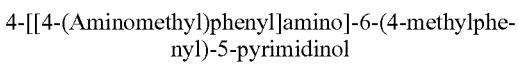

To 110 mg of 2 in 5 mL of 7M ammonia in methanol was added about 3 mL of a 50% Raney nickel slurry in water and the mixture shaken under 45 psi of H$_2$ for 2 hours. The reaction mixture was filtered and evaporated to dryness. Purification by RP-HPLC yielded 53 mg of 3. LCMS: 307.2 (MH$^+$)

Example 4

4-[[5-Hydroxy-6-(4-methylphenyl)-4-pyrimidinyl]amino]benzenecarboximidamide

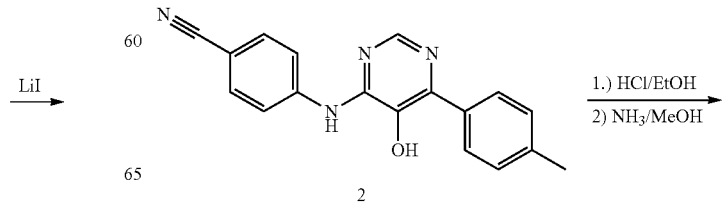

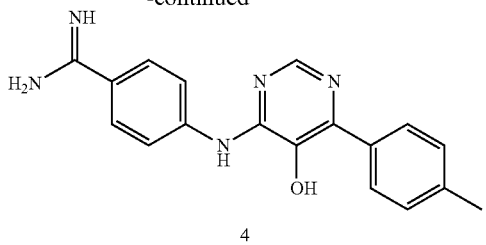

4

To 975 mg of 2 in 175 mL of EtOH at −78° C. was bubbled HCl gas until solution became saturated. The reaction flask was then sealed with rubber septa and allowed to warm to room temperature while stirring. After 16 hours the reaction mixture was evaporated to dryness. To the residue was twice added EtOH then evaporated to dryness. To the residue was added 150 mL of 7M ammonia in methanol and the mixture stirred at room temperature in a flask sealed with rubber septa. After 16 hours, the reaction mixture was evaporated to dryness and the residue purified by RP-HPLC yielding 395 mg of 4.

LCMS: 320.2 (MH$^+$)

Example 5

Step 1

2-[5-Methoxy-6-(4-methylphenyl)-4-pyrimidinyl]-1h-indole-6-carbonitrile

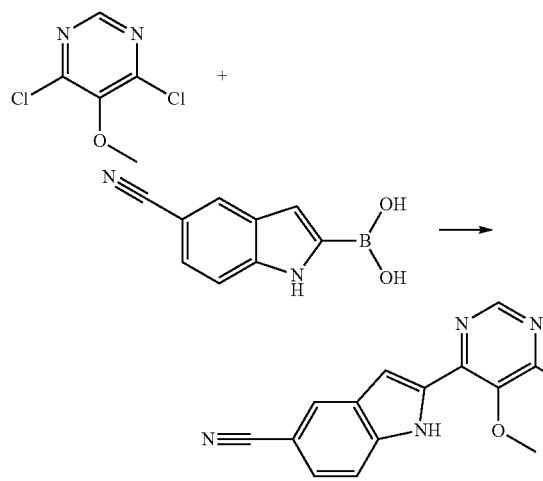

P12

To 1.44 g of 4,6-dichloro-5-methoxypyrimidine in 5 mL of toluene, 3 mL of water and 3 mL of DME was added 1 g of 5-cyanoindole-2-boronic acid, 2.23 g of potassium carbonate and 311 mg of tetrakis(triphenylphosphine)palladium. After bubbling with argon for 2 minutes the reaction mixture was heated to 140° C. in a pressure tube using a microwave reactor. The reaction mixture was poured onto water and extracted three times with ethyl acetate. The combined extracts were washed with brine, dried with magnesium sulfate, filtered and evaporated to dryness. The solid residue was triturated in ethyl acetate and filtered. The filtrate then evaporated to dryness and purified by flash chromatography yielding 240 mg of P12.

Step 2

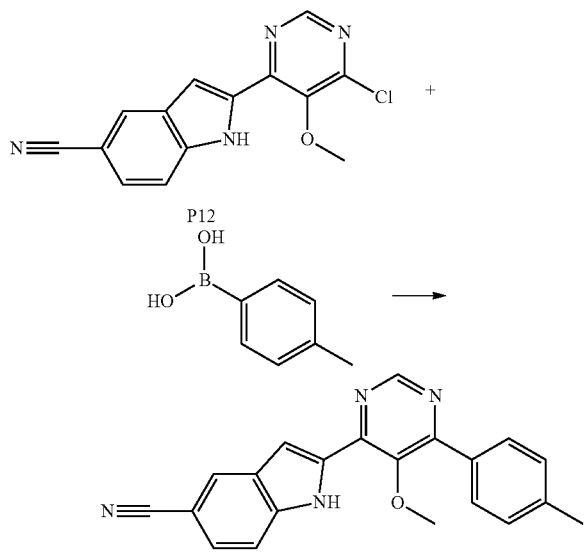

5

To 240 mg of P12 in 2 mL of toluene, 1 mL of water and 1 mL of DME was added 4-tolylboronic acid, 350 mg of potassium carbonate and 49 mg of tetrakis(triphenylphosphine) palladium. After bubbling with argon for 2 minutes the reaction mixture was heated to 100° C. for 16 hours in an oil bath. The reaction mixture was poured onto water and extracted three times with ethyl acetate. The combined extracts were washed with brine, dried with magnesium sulfate, filtered and evaporated to dryness. The residue was purified by flash chromatography yielding 69 mg of 5. LCMS: 341.2 (MH$^+$)

Example 6

4-[5-(Aminomethyl)-1h-indol-2-yl]-6-(4-methylphenyl)-5-pyrimidinol

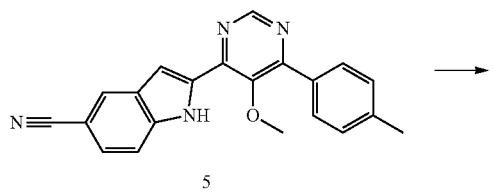

5

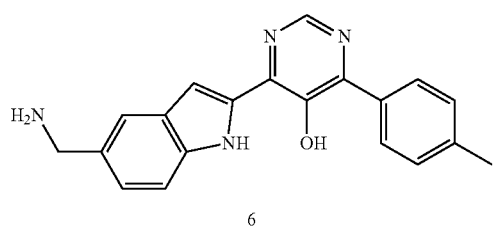

6

To 200 mg of 11 in 1.5 mL of quinoline was added 138 mg of lithium iodide and the mixture bubbled with argon for several minutes. The reaction mixture was sealed in a pressure tube and heated to 200° C. for 10 minutes using a microwave reactor. The reaction mixture was evaporated to dryness and purified by flash chromatography yielding 23 mg of demethylated product.

To a solution of the above product in 5 mL of 2M ammonia in methanol was injected into an H-Cube hydrogenation device equipped with a Raney Ni cartridge and processed with 60 psi of $H_2$ at 50° C. with a flow rate of 0.5 mL/min. After four cycles through the device the effluent was evaporated to dryness and the residue purified by RP-HPLC yielding 12 mg of 6. LCMS: 331.2 ($MH^+$)

Example 7

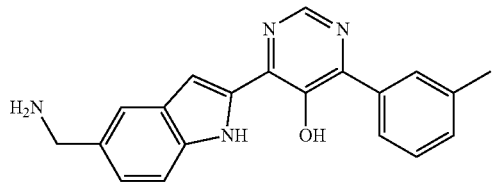

7

Example 7 was prepared using a procedure similar to the preparation of 6.

LCMS: 331.2 ($MH^+$)

Example 8

1,1-Dimethylethyl 1,3-dihydro-5-[[5-methoxy-6-(4-methylphenyl)-4-pyrimidinyl]amino]-2h-isoindole-2-carboxylate Step 1

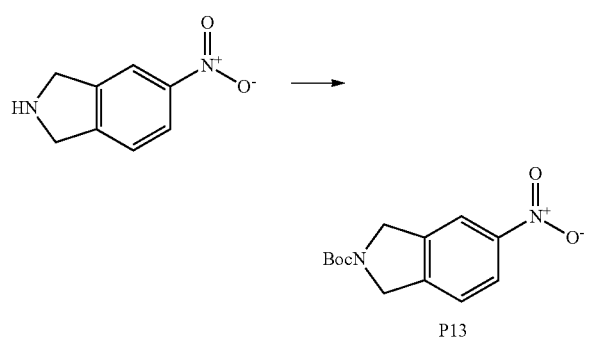

P13

To 390 mg of 5-nitrosoindoline in 50 mL of DCM at 0° was added 540 uL of triethylamine and 510 mg of di-tert-butyl-dicarbonate and the mixture stirred under nitrogen while warming to room temperature. After 16 hours the reaction mixture was poured onto water and extracted three times with DCM. The combined extracts were washed with brine, dried with magnesium sulfate, filtered and evaporated to dryness yielding 560 mg of P13.

Step 2

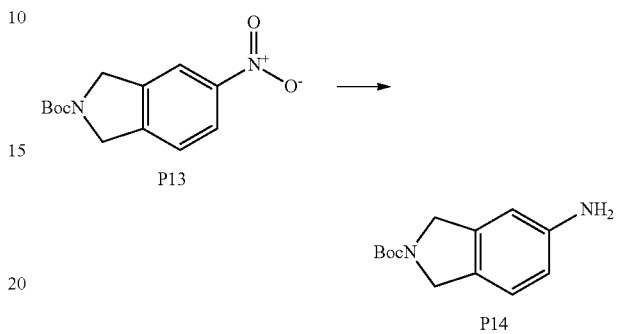

P13

P14

To 560 mg of P13 in 20 mL of ethanol was added 56 mg of 10% Pd/C and the mixture shaken under 35 psi of hydrogen gas for 15 minutes. The mixture was filtered and evaporated to dryness yielding 516 mg of P14.

Step 3

P15

To 2.5 g of 4,6-dichloro-5-methoxypyrimidine in 20 mL of toluene, 5 mL of water and 5 mL of DME was added 1.9 g of 4-tolyl boronic acid, 5.8 g of potassium carbonate and 810 mg of tetrakis(triphenylphosphine)palladium. After bubbling with argon for 2 minutes the reaction mixture was heated to 100° C. for 16 hours in an oil bath. The reaction mixture was poured onto water and extracted three times with ethyl acetate. The combined extracts were washed with brine, dried with magnesium sulfate, filtered and evaporated to dryness. The residue was purified by flash chromatography yielding 2.17 g of P15.

Step 4

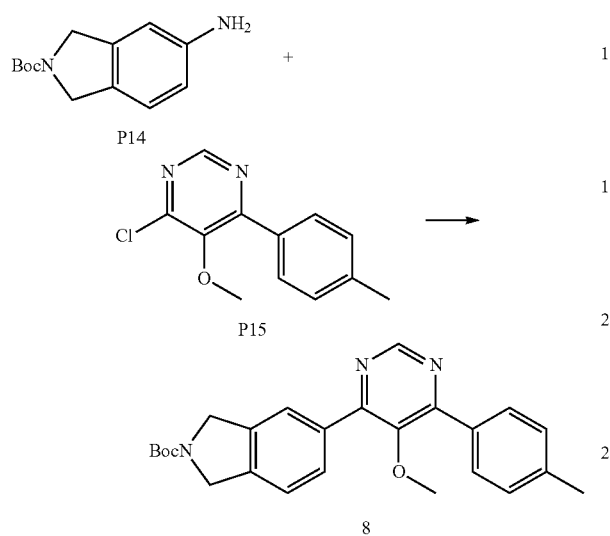

To 517 mg of P14 in 15 mL of THF at 0° C. was added 350 mg of 60% sodium hydride in mineral oil and the mixture stirred for 10 minutes. 570 mg of P15 was then added and the mixture warmed to room temperature. After three days the reaction mixture was quenched with water then extracted three times with ethyl acetate. The combined extracts were washed with brine, dried with magnesium sulfate, filtered and evaporated to dryness. Purification by flash chromatography yielded 450 mg of 8. LCMS: 433.2 (MH$^+$)

Example 9

4-[(2,3-Dihydro-1 h-isoindol-5-yl)amino]-6-(4-methylphenyl)-5-pyrimidinol

Step 1

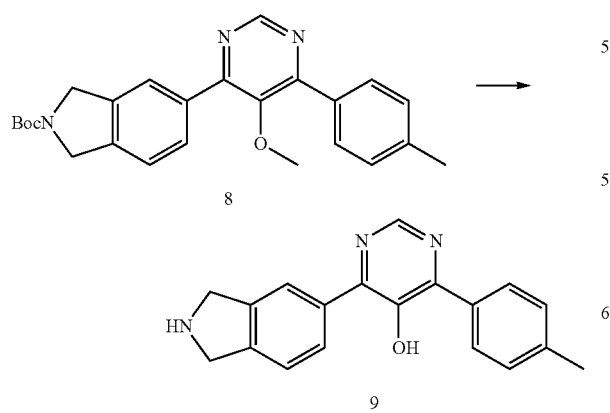

To 100 mg of 8 in 7 mL of DME was added 132 uL of TMSI and the mixture stirred under nitrogen for four hours. An additional 198 uL of TMSI was added and the mixture heated to 80° C. in a pressure tube for two days. The reaction mixture was poured onto water and extracted three times with DCM. The combined extracts were washed with brine, dried with magnesium sulfate, filtered and evaporated to dryness. Purification by RP-HPLC yielded 25 mg of 9.

LCMS: 319.2 (MH$^+$)

Example 10

4,6-Bis(4-fluorophenoxy)-5-methoxypyrimidine

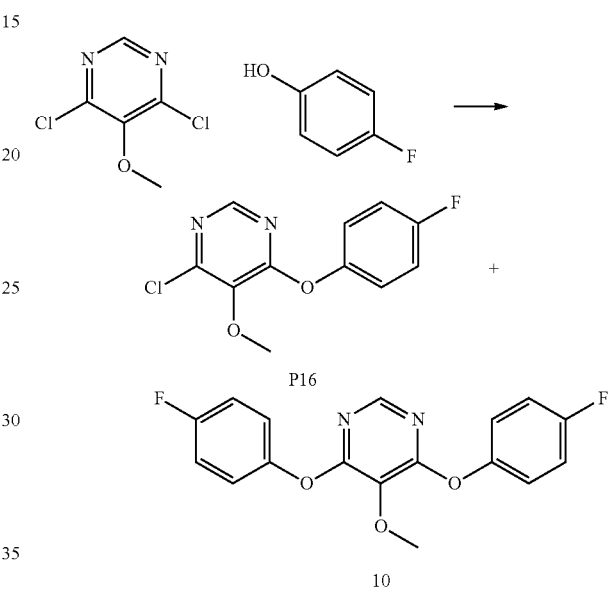

To a solution of 4-fluorophenol (630 mg, 5.61 mmol) in 20 ml THF at rt was added $^t$BuOK (815 mg, 7.26 mmol, 1.3 eq.) and mixture for about 10 min. and cooled to 0° C. To this was added 4,6-dichloro-5-methoxypyrimidine (1.0 g, 5.59 mmol) in one portion and the mixture was stirred overnight while allowing to warm to rt. It was quenched with aq. NH$_4$Cl, extracted 3× with ethyl acetate, the combined organic layer was washed with brine, dried over MgSO$_4$, filtered, concentrated and the residue purified by flash chromatography using 10% ethyl acetate in hexanes to provide 950 mg of P16 and 14 mg of 10.

LCMS for 10: 331.2 (MH$^+$)

Example 11

4-[[6-(4-Fluorophenoxy)-5-methoxy-4-pyrimidinyl]amino]benzonitrile

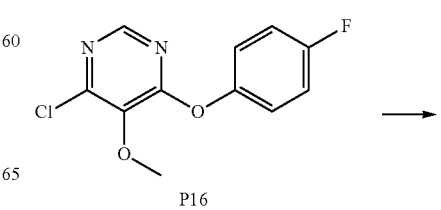

-continued

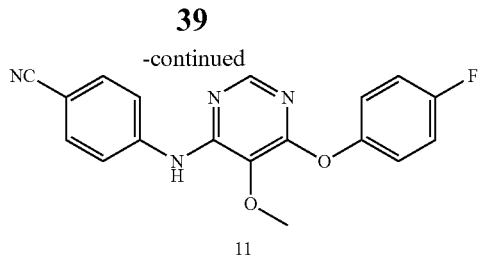
11

To solution of P16 (520 mg, 2.04 mmol) and 4-aminobenzonitrile (265 mg, 2.24 mmol, 1.1 eq.) in 10 ml DMF at rt was added a 60% suspension of sodium hydride in mineral oil (410 mg, 10.25 mmol, 5 eq.) and the mixture was stirred for 2 hr. It was quenched with aq. NH$_4$Cl, extracted 3× with ethyl acetate, the combined organic layer washed with brine, dried over MgSO$_4$, filtered, concentrated and the crude purified by flash chromatography using 5% ethyl acetate in dichloromethane to provide 239 mg of 11.

LCMS: 337.2 (MH$^+$)

Example 12

4-[[6-(4-Fluorophenoxy)-5-hydroxy-4-pyrimidinyl]amino]benzenecarboximidamide

Step 1

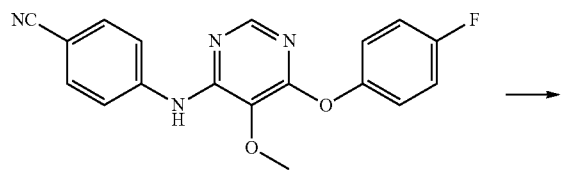

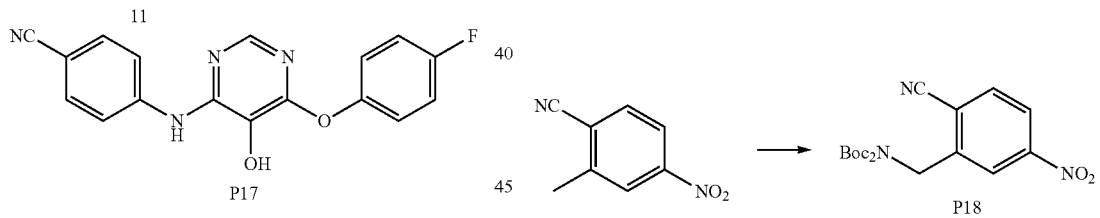

A mixture of 11 (185 mg, 0.55 mmol), lithium iodide (740 mg, 5.53 mmol, 10 eq.) in 5 ml 2-picoline was heated in a sealed tube in a microwave reactor at 200° C. for 15 min. The mixture was diluted with ethyl acetate, washed 3× with water, brine, dried over MgSO$_4$, filtered, concentrated and purified flash chromatography using 40% ethyl acetate in hexanes to provide 109 mg of P17.

Step 2

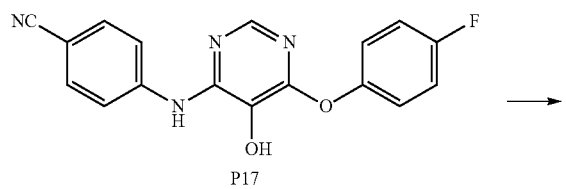

-continued

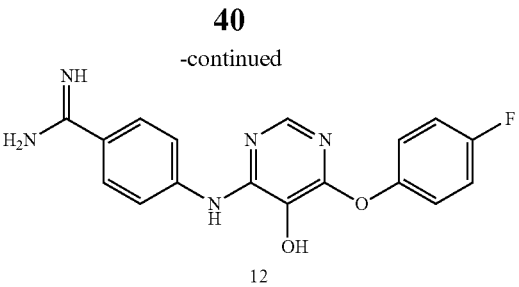
12

To a flask containing P17 (45 mg) was added 1.4 ml of absolute ethanol. The flask was flushed with nitrogen and capped with septa. Using a copper wire the septa was tied tightly to the flask so that it can withstand the small pressure that will develop during the reaction. The solution was cooled in an ice-bath and 1.1 ml of acetyl chloride was added drop by drop over a period of few minutes. Once the addition was complete, the mixture was stirred overnight while allowing warming to rt. The solvent was evaporated to dryness and the residue was taken in 7N NH$_3$ in MeOH and heated in a sealed tube at 60° C. for 2.5 hr. The solvent was evaporated to dryness and the residue was purified by RP-HPLC to provide 31 mg 12. LCMS: 340.2 (MH$^+$)

Examples 13 and 14

4-[(2,3-Dihydro-1-imino-1h-isoindol-5-yl)amino]-6-(4-methylphenyl)-5-pyrimidinol (13)

2,3-Dihydro-1-imino-n-[5-methoxy-6-(4-methylphenyl)-4-pyrimidinyl]-1h-isoindol-5-amine (14)

Step 1

A degassed solution of 2-methyl-4-nitrobenzonitrile (10 g, 61.7 mmol), N-bromosuccinimide (13.2 g (74.17 mmol, 1.2 eq.) and azobisisobutyronitrile (AIBN) (2.0 g, 12.18 mmol, 0.2 eq) in 300 ml CCl$_4$ was heated at reflux for 3 days. After solvent was evaporated the residue was taken in ethyl acetate and washed 2× with aq. NaHCO$_3$, aq. Na$_2$S$_2$O$_3$, brine, dried over MgSO$_4$, filtered, concentrated and purified chromatography using 15% ethyl acetate in hexane to provide 11.7 g of 2-bromomethyl-4-nitrobenzonitrile.

A mixture of above product, Di-tert-butyl iminodicarboxylate (13.8 g, 63.5 mmol, 1.3 eq.), potassium carbonate (13.3 g, 97.7 mmol, 2 eq) and tetrabutylammonium iodide (1.8 g, 4.87 mmol, 0.1 eq) in 150 ml DMF was stirred overnight at rt, diluted with water and extracted 3× with ether. The combined organic layer washed with water, brine, dried over MgSO$_4$, filtered, concentrated and purified flash chromatography using 15% ethyl acetate in hexanes to provide 14.4 g of P18.

The combined organic layer was washed with brine, dried over MgSO₄, filtered, concentrated and purified by flash chromatography using 30% ethyl acetate in hexanes to provide 132 mg of P20.

Step 2

Step 4

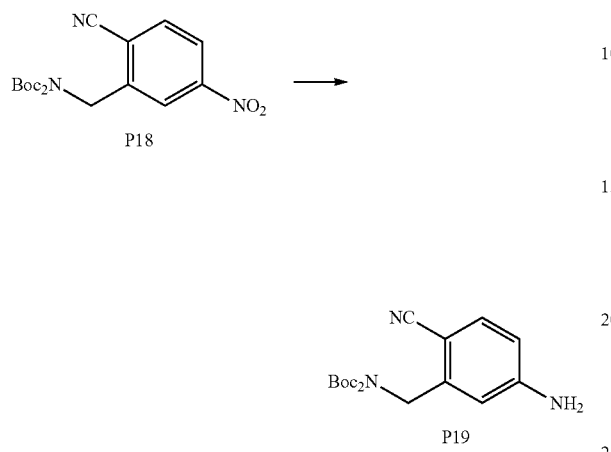

A suspension of P18 (3.3 g) and 10% Pd—C (330 mg) in 30 ml each of THF and methanol was stirred overnight under a hydrogen balloon. The catalyst was removed by filtration through a CELITE pad; the filtrate was concentrated and purified by flash chromatography using 30% ethyl acetate in hexanes to provide 2.1 g of P19.

Step 3

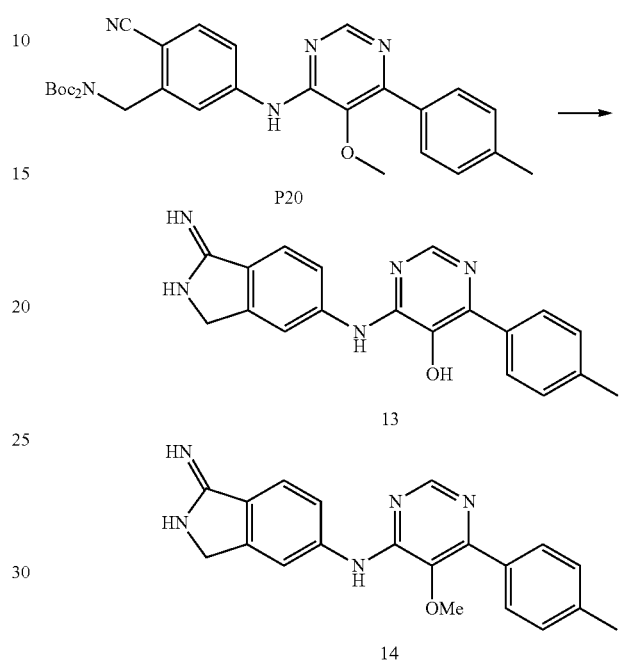

A mixture of P20 (80 mg, 0.18 mmol) and tetrabutylammonium iodide (14 mg, 0.038 mmol, 0.2 eq.) in 2 ml of 47% aq. hydroiodic acid in a microwave reactor vessel was stirred vigorously using a vortex mixture. The vessel was capped then heated in a microwave reactor at 100° C. for 30 min. The mixture was evaporated to dryness then evaporated twice with ethanol. The residue was purified by RP-HPLC to provide 20 mg of 13 and 44 mg of 14. LCMS for 13: 333.2 (MH⁺); LCMS for 14: 346.2 (MH⁺)

Example 15

4-[(6-Chloro-2,3-dihydro-1-imino-1h-isoindol-5-yl)amino]-6-(4-methylphenyl)-5-pyrimidinol Step 1

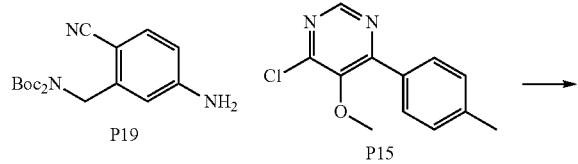

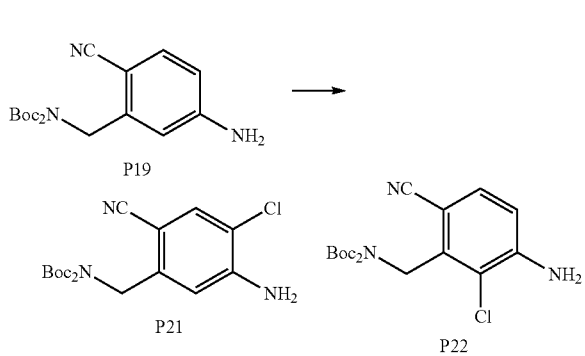

A mixture of P19 (300 mg, 0.795 mmol), P15 (190 mg (0.81 mmol), tris(dibenzylideneacetone)dipalladium (23 mg, 0.04 mmol, 5 mol %), (±) BINAP (74 mg, 0.119 mmol, 15 mol %) and sodium tert-butoxide (115 mg, 1.20 mmol, 1.5 eq.) in 5 ml toluene in a sealed was bubbled with argon and heated overnight in an oil bath at 110° C. The mixture was quenched with aq. NH₄Cl and extracted 3× with ethyl acetate.

To a solution of P19 (950 mg, 2.73 mmol) in 10 ml isopropanol at 60° C. was added N-chlorosuccinimide (400 mg, 2.99 mmol, 1,1 eq). The mixture was heated at reflux for 1.5 hr, left overnight at rt, concentrated and diluted with ethyl acetate. The solution was washed 2× with water, brine, dried over MgSO$_4$, filtered, concentrated and purified by flash chromatography using 40% ethyl acetate in hexanes to provide 319 mg of P21 and 288 mg of P22.

Step 2

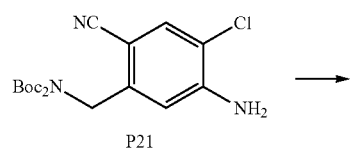

P21

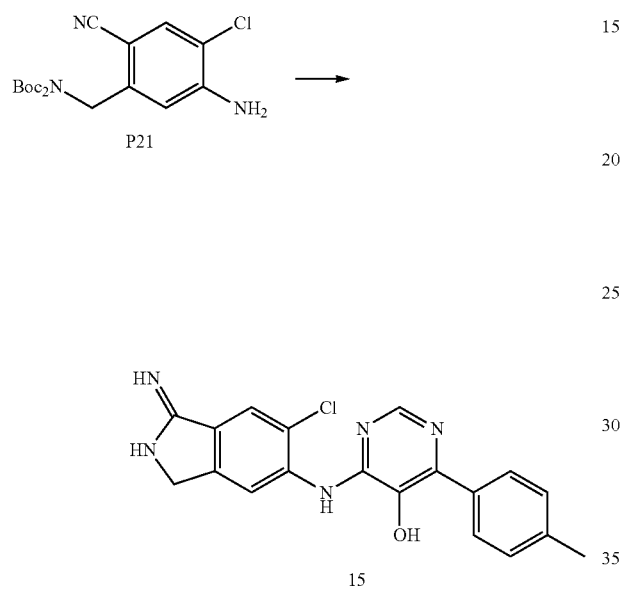

15

Using a procedure similar to the transformation of P19 to 13, 15 was obtained from P21. LCMS: 366.2 (MH$^+$)

Example 16

6-Chloro-2,3-dihydro-1-imino-n-[5-methoxy-6-(4-methylphenyl)-4-pyrimidinyl]-1h-isoindol-5-amine Step 1

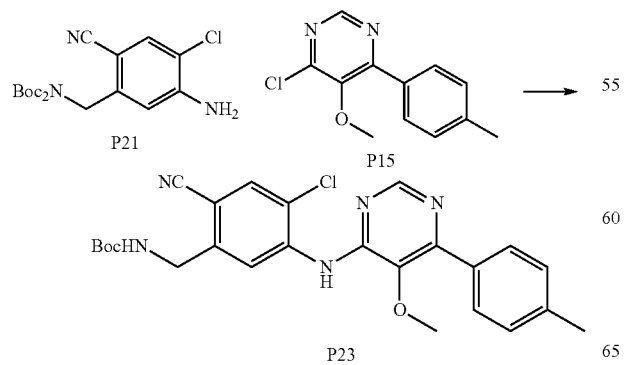

P23

Using a procedure similar to the transformation of P19 to P20, P23 was obtained from P21.

Step 2

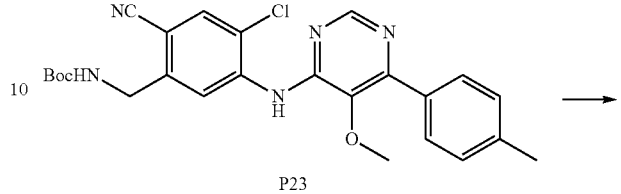

P23

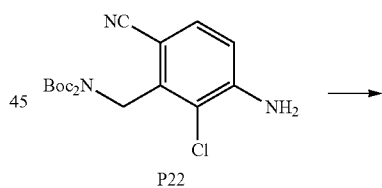

16

A solution of 20 mg of P23 was stirred rt with 0.5 ml each of trifluoroacetic acid and dichloromethane for 2 hr. It was concentrated and purified by RP-HPLC to obtained 15 mg of 16. LCMS: 380.2 (MH$^+$)

Example 17

4-[(4-Chloro-2,3-dihydro-1-imino-1h-isoindol-5-yl)amino]-6-(4-methylphenyl)-5-pyrimidinol

P22

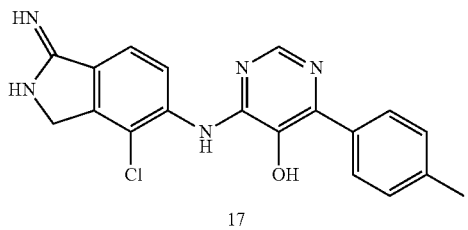

17

Using a procedure similar to the transformation of P19 to 13, 17 was obtained from P22. LCMS: 366.2 (MH+)

Example 18

4-[6-[(2,3-Dihydro-1-imino-1h-isoindol-5-yl)amino]-5-hydroxy-4-pyrimidinyl]benzoic acid Step 1

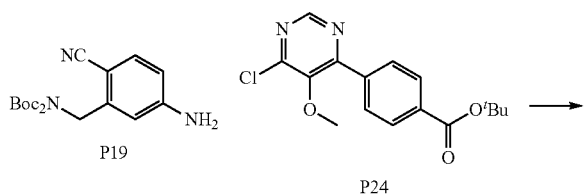

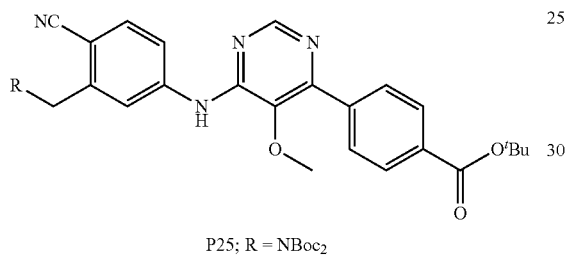

P25; R = NBoc₂
P26; R = NHBoc

P24 was prepared from 3,5-dichloro-5-methoxypyrimidine and 4-(tert-butoxycarbonyl)phenylboronic acid using a procedure similar to the preparation of P15.

A mixture of P19 (300 mg, 0.795 mmol), P24 (255 mg, 0.795 mmol), tris(dibenzylideneacetone)dipalladium (23 mg, 0.04 mmol, 5 mol %), BINAP (74 mg, 0.119 mmol, 15 mol %) and sodium tert-butoxide (115 mg, 1.20 mmol, 1.5 eq.) in 5 ml toluene in a sealed was bubbled with argon and heated for about 20 hr in an oil bath at 110° C. The mixture was quenched with aq. NH₄Cl and extracted 3× with ethyl acetate. The combined organic layer was washed with brine, dried over MgSO₄, filtered, concentrated and purified by flash chromatography using 30% ethyl acetate in hexanes to provide 72 mg of P25 and 151 mg of P26.

Step 2

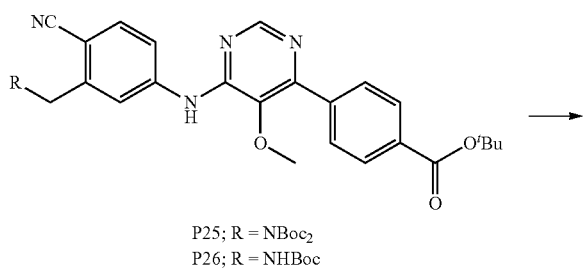

P25; R = NBoc₂
P26; R = NHBoc

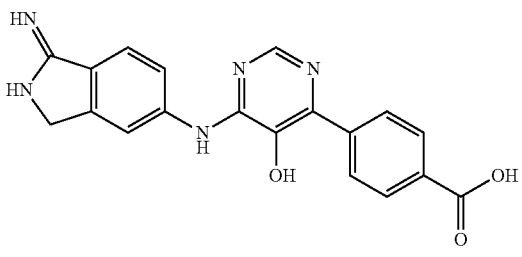

18

A mixture of 100 mg of P25, 150 mg of P26 and 30 mg of tetrabutylammonium iodide in 3 ml of con. hydroiodic acid was heated in a microwave reactor at 130° C. for 30 min. The product was filtered to obtain 120 mg of solid which on analysis indicated incomplete reaction. It was once again dissolved in 2 ml of con. hydroiodic acid and heated with 20 mg of tetrabutylammonium iodide for another 30 min. at 130° C. The solid was filtered, washed with water, ether and dried in vacuum oven to provide 52 mg of 18 as the hydroiodide salt. LCMS: 362.2 (MH+)

Example 19

5-[[5-Methoxy-6-(4-methylphenyl)-4-pyrimidinyl]amino]-2-pyridinecarbonitrile

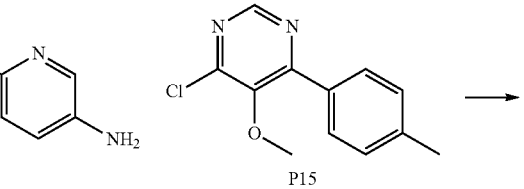

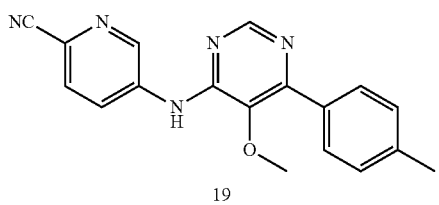

19

To a solution of P15 (500 mg, 2.13 mmol) and 3-amino-6-cyanopyridine (330 mg, 2.77 mmol, 1.3 eq.) in 10 ml DMF at rt was added a 60% suspension of sodium hydride in mineral oil (430 mg, 10.75 mmol, 5 eq.) and stirred at rt for 2 hr. It was quenched by the addition of aq. NH₄Cl and extracted 3× with ethyl acetate. The combined organic layer was washed with brine, dried over MgSO₄, filtered, concentrated and purified by chromatography using 20% ethyl acetate in dichloromethane to provide 510 mg of 19. LCMS: 318.2 (MH+)

Example 20

5-[[5-Hydroxy-6-(4-methylphenyl)-4-pyrimidinyl]amino]-2-pyridinecarbonitrile

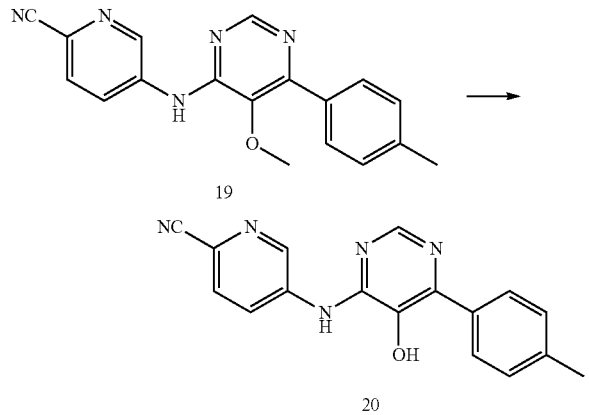

Using a procedure similar to the transformation of 1 to 2, 19 was transformed to 20. LCMS: 304.2 (MH+)

Example 21

5-[[5-Hydroxy-6-(4-methylphenyl)-4-pyrimidinyl]amino]-2-pyridinecarboximidamide

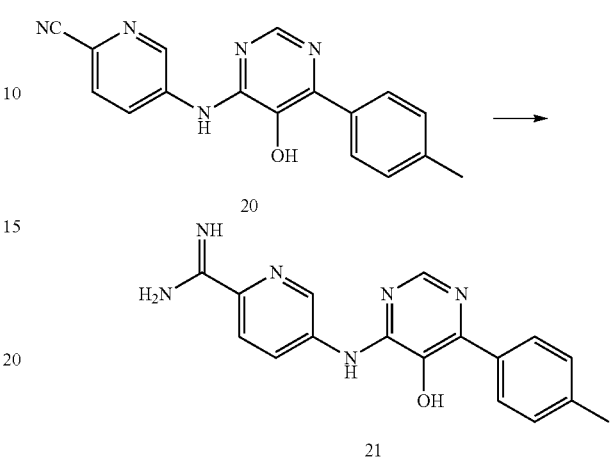

Using a procedure similar to the transformation of P17 to 12, 20 was transformed to 21. LCMS: 321.2 (MH+)

Examples 22-29

Using procedures similar to those described above, the following examples were prepared.

| Compound # | Structure | LCMS (MH+) |
|---|---|---|
| 22 | 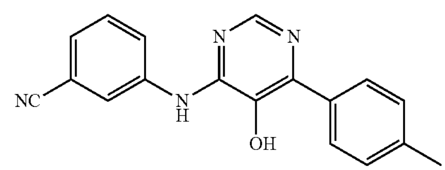 [SMILES: Cc1ccc(-c2ncnc(Nc3cccc(C#N)c3)c2O)cc1] | 303.2 |
| 23 | 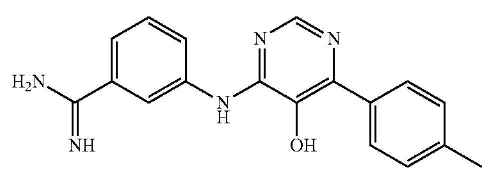 [SMILES: Cc1ccc(-c2ncnc(Nc3cccc(C(=N)N)c3)c2O)cc1] | 320.2 |
| 24 | 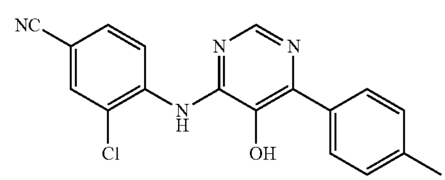 [SMILES: Cc1ccc(-c2ncnc(Nc3ccc(C#N)cc3Cl)c2O)cc1] | 337.2 |
| 25 | 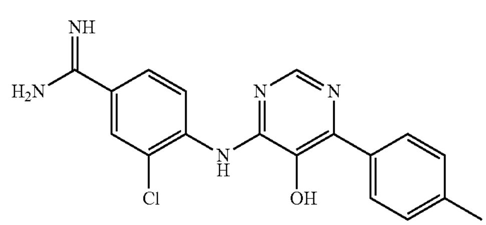 [SMILES: Cc1ccc(-c2ncnc(Nc3ccc(C(=N)N)cc3Cl)c2O)cc1] | 354.2 |

| Compound # | Structure | LCMS (MH+) |
|---|---|---|
| 26 | 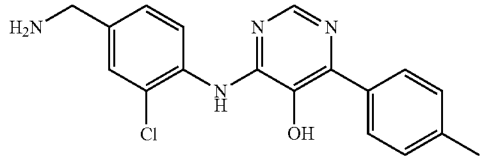 [SMILES: Cc1ccc(-c2ncnc(Nc3ccc(CN)cc3Cl)c2O)cc1] | 341.2 |
| 27 | 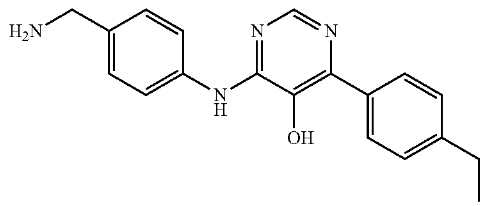 [SMILES: CCc1ccc(-c2ncnc(Nc3ccc(CN)cc3)c2O)cc1] | 321.2 |
| 28 | 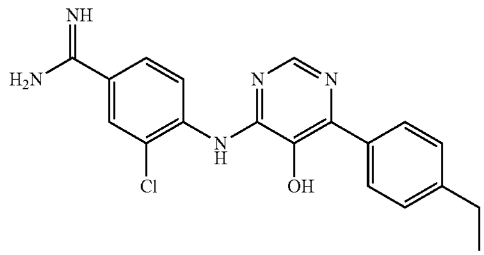 [SMILES: CCc1ccc(-c2ncnc(Nc3ccc(C(=N)N)cc3Cl)c2O)cc1] | 334.2 |
| 29 | 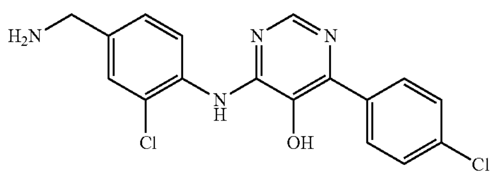 [SMILES: NCc1ccc(Nc2ncnc(-c3ccc(Cl)cc3)c2O)c(Cl)c1] | 327.2 |

Example 30

1-Amino-n-[5-methoxy-6-(4-methylphenyl)-4-pyrimidinyl]-6-isoquinolinemethanamine To a solution of 50 mg of 1 in 3 mL of DMF was added 44 mg of 6-(aminomethyl)isoquinolin-1-amine and 59 mg of potassium carbonate and the mixture stirred under nitrogen for 16 hours then the temperature raised to 60° C. After ten days the reaction mixture was poured onto water and extracted three times with ethyl acetate. The combined extracts were washed with brine, dried with magnesium sulfate, filtered and evaporated to dryness. The residue was purified by flash chromatography yielding 30 mg of 30. LCMS: 372.2 (MH+)

Example 31

3-Chloro-4-[[5-hydroxy-6-(4-methylphenyl)-4-pyrimidinyl]oxy]benzonitrile

Step 1

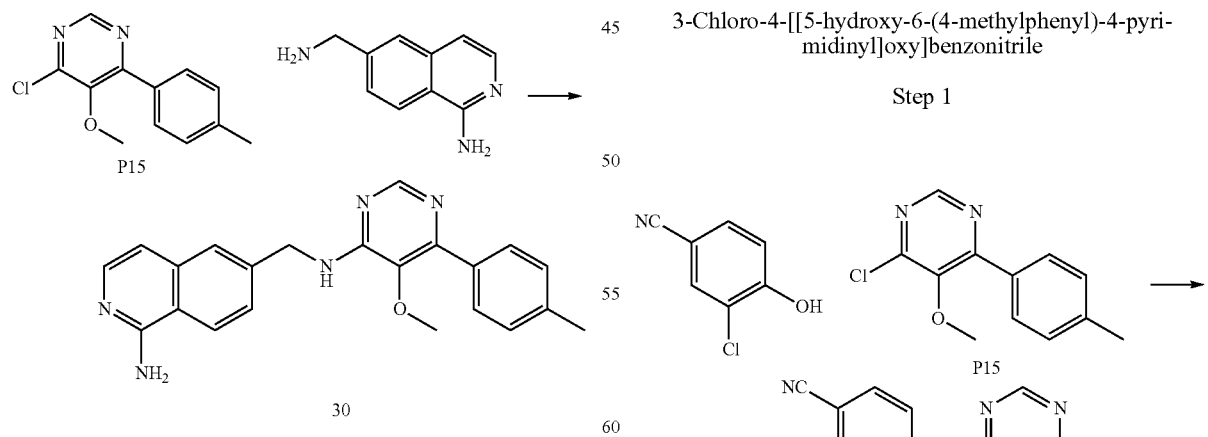

A mixture of P15 (500 mg, 2.14 mmol), 3-chloro-4-hydroxybenzonitrile (400 mg, 2.60 mmol, 1.2 eq.), tetrabutylammonium iodide (480 mg, 1.30 mmol, 0.6 eq.) and potassium carbonate (350 mg, 2.57 mmol, 1.2 eq.) in 10 ml DMSO was heated in sealed tube at 130° C. for 2 hr. It was diluted with ethyl acetate, washed 3× with water, brine, dried over MgSO₄, filtered, concentrated and purified by chromatography using 15% ethyl acetate in hexanes to provide 370 mg of P27.

Step 2

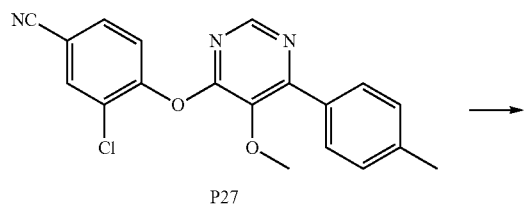

P27

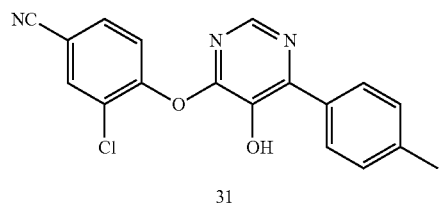

31

Using a procedure similar to the transformation of 1 to 2, 31 was obtained from P27. LCMS: 338.2 (MH⁺)

Example 32

3-Chloro-4-[[5-hydroxy-6-(4-methylphenyl)-4-pyrimidinyl]oxy]benzenecarboximidamide

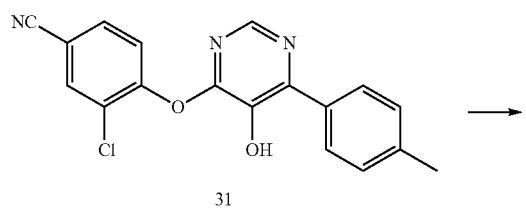

31

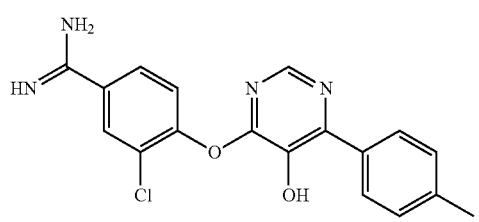

32

Using procedure similar to the transformation of P17 to 12, 32 was obtained from 31. LCMS: 355.2 (MH⁺)

Example 33

4-[[5-Hydroxy-6-(4-methylphenyl)-4-pyrimidinyl]oxy]benzenecarboximidamide

Step 1

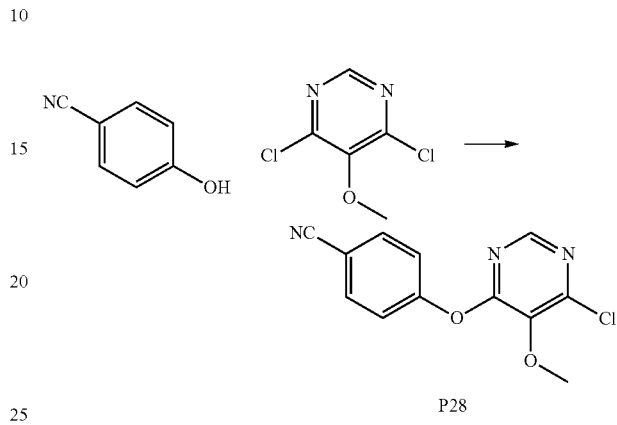

P28

To a solution of 4-cynaophenol (400 mg, 3.36 mmol) in 10 ml THF at rt was added potassium-tert-butoxide (380 mg, 3.39 mmol, 1.2 eq) and stirred for 20 minutes. To this was added 4,6-dichloro-5-methoxypyrimidine (500 mg, 2.79 mmol) and stirred for 3 days at rt. It was quenched by the addition of aq. NH₄Cl and extracted 3× with ethyl acetate. The combined organic layer was washed with brine, dried over MgSO₄, filtered, concentrated and purified by flash chromatography using 20% ethyl acetate in hexanes to provide 175 mg of P28.

Step 2

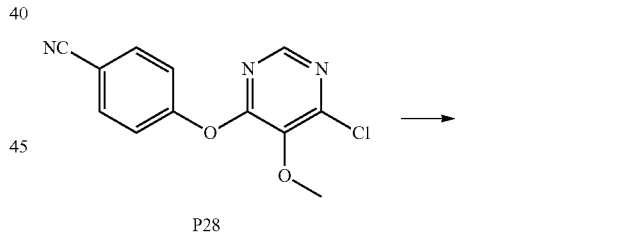

P28

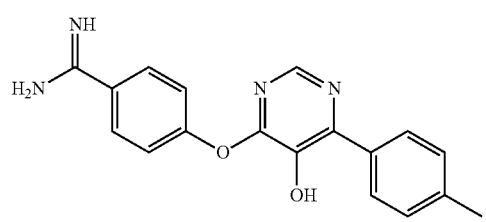

33

Using procedure similar to the transformation of P11 to 4, 33 was obtained from P28. LCMS: 321.2 (MH⁺)

Example 34

2,3-Dihydro-5-[[5-hydroxy-6-(4-methylphenyl)-4-pyrimidinyl]amino]-1h-isoindol-1-one Step 1

A degassed solution of methyl 2-methyl-4-nitrobenzoate (3.5 g, 18.19 mmol), N-bromosuccinimide (3.9 g, 21.91 mmol, 1.2 eq) and benzoyl peroxide (3.63 mmol, 0.2 eq.) in 100 ml 0014 was heated at reflux for 4 hr. It was concentrated to dryness, dissolved in ether, washed 2× with water, aq. Na₂S₂O₃, brine, dried over MgSO₄, filtered, concentrated and purified by chromatography using 15% ethyl acetate in hexanes to provide 4.11 g of methyl 2-bromomethyl-4-nitrobenzoate.

To a solution of the above product in 40 ml DMF at rt was added 2,4-dimethoxybenzyl amine (2.7 ml, 17.98 mmol, 1.2 eq.), potassium carbonate (4.1 g, 30.12 mmol, 2 eq.) and the mixture stirred overnight at rt. It was diluted with ethyl acetate, washed 2× with water, 1N HCl, brine, dried over MgSO₄, filtered, concentrated and purified by chromatography using 5% ethyl acetate in dichloromethane to provide 2.43 g of P29.

Step 2

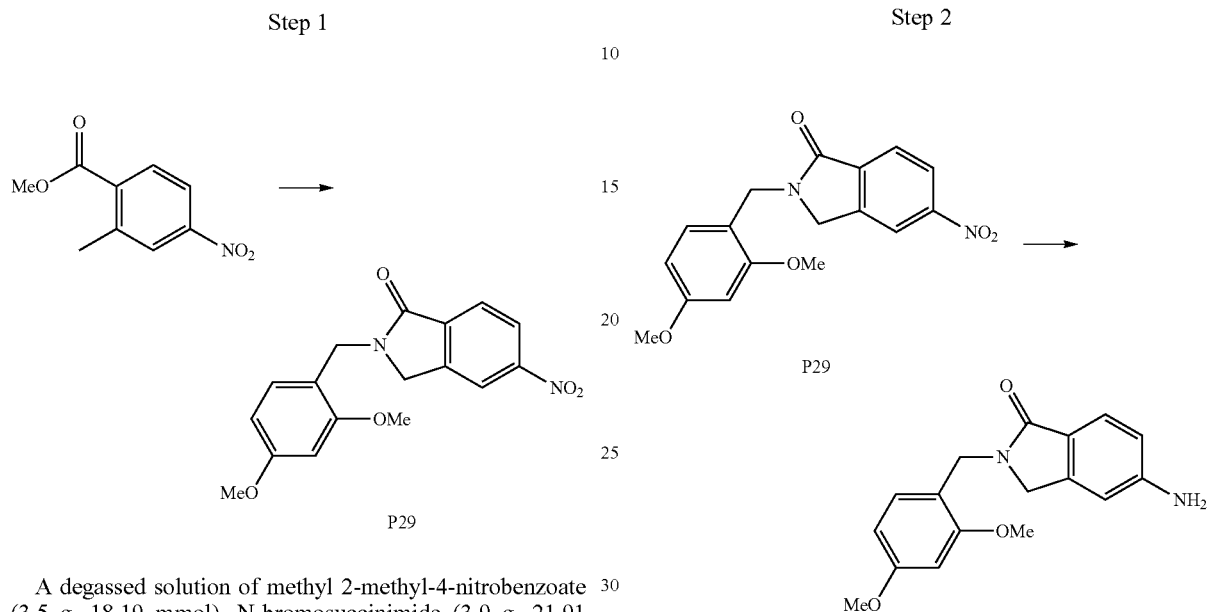

A mixture of 500 mg of P29 and 100 mg of 10% Pd—C in 15 ml ethanol and 10 ml THF was stirred under a hydrogen balloon for 1 hr. It was filtered through a CELITE pad and concentrated to provide 440 mg of P30.

Step 3

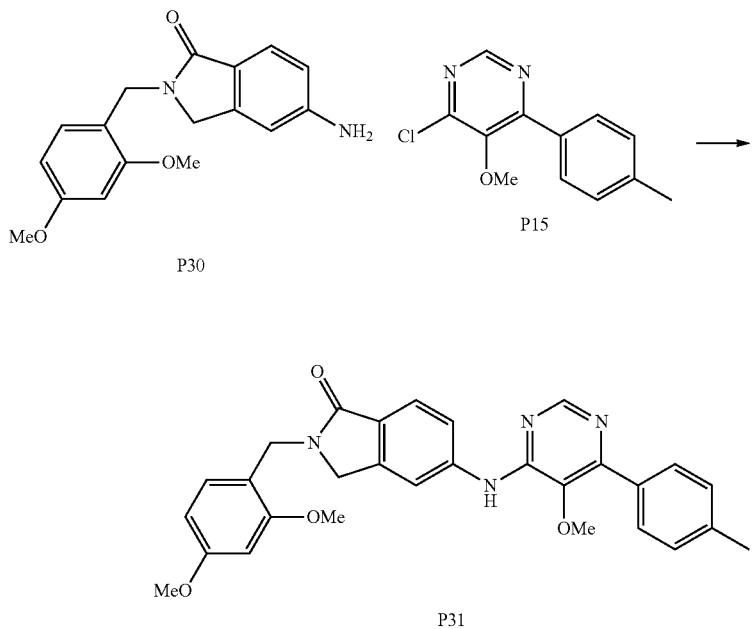

Using a procedure similar to the transformation of P15 to 19, P15 was converted to P31.

Step 4

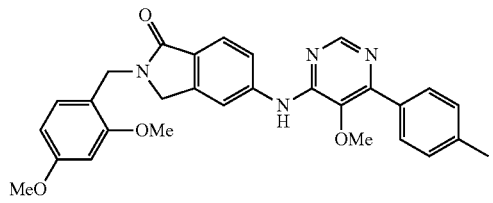

P31

A solution of 220 mg of P31 in 5 ml of 95:5 TFA-water mixture was heated in a microwave reactor at 120° C. for 20 min. It was concentrated and diluted with aq. NaHCO₃. The solid was filtered, washed with water, ether and dried in vacuum oven to provide 200 mg of P32.

Step 5

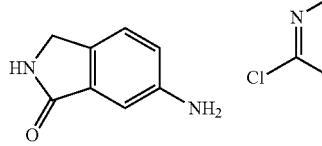

P32

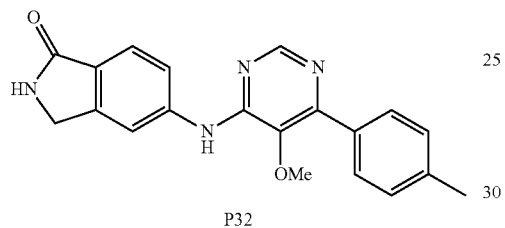

34

Using a procedure similar to the preparation of 1 to 2, 34 was obtained from P32. LCMS: 333.2 (MH⁺)

Example 35

2,3-Dihydro-6-[[5-hydroxy-6-(4-methylphenyl)-4-pyrimidinyl]amino]-1h-isoindol-1-one Step 1

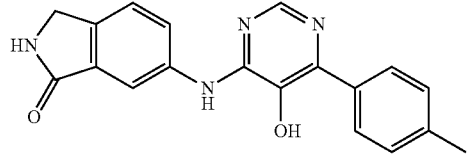

P15

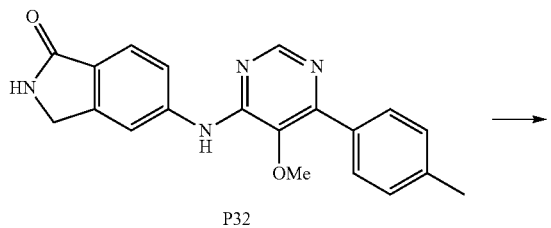

P33

Commercially available 6-amino-2,3-dihydro-isoindol-1-one was coupled with P15 using procedure similar to the transformation of P19 to P20 to obtain P33.

Step 2

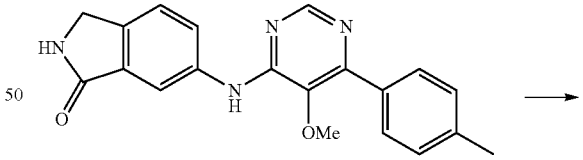

P33

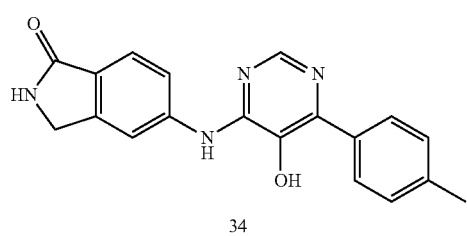

SCH 2341580
35

A mixture of P33 (28 mg, 0.081 mmol), tetrabutylammonium iodide (6 mg, 0.2 eq.) in 1 ml concentrated hydroiodic acid was heated in a microwave reactor at 130° C. for 30 min.

The mixture was concentrated and purified by RP-HPLC to provide 11 mg of 35. LCMS: 333.2 (MH+)

Example 36

4-[(4-Ethenylphenyl)amino]-6-(4-methylphenyl)-5-pyrimidinol

Step 1

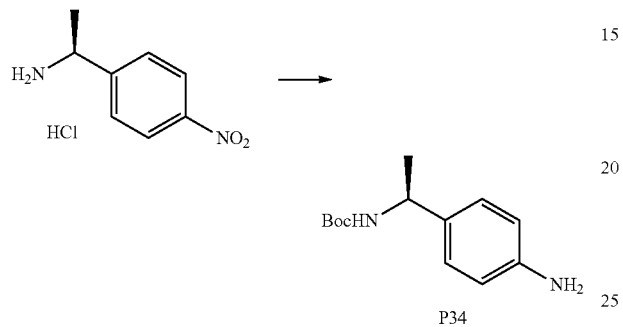

P34

To a solution of in di-tert-butyldicarbonate (4.9 g, 22.45 mmol, 1.5 eq.) in 30 ml THF at rt was added (R)-alpha-methyl-4-nitrobenzylamine hydrochloride (3.0 g, 14.81 mmol) followed by 30 ml of 1N aq. NaOH solution. The mixture was stirred vigorously for 2 hr, diluted with water and extracted 3× with ether. The combined organic layer was washed with brine, dried over MgSO$_4$, filtered and concentrated to provide 5.50 g (S)-tert-butyl 1-(4-nitrophenyl)ethyl-carbamate.

A mixture of 2.7 g of the above product and 500 mg of 10% Pd—C in 25 ml each of THF and EtOH was stirred overnight under a hydrogen balloon. The mixture was filtered through a CELITE pad, concentrated and purified by chromatography using 30% ethyl acetate to provide 1.05 g of P34.

Step 2

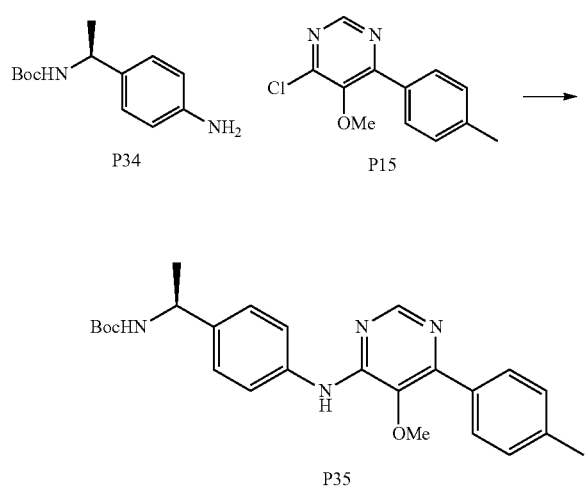

P35

Using a procedure similar to the transformation of P15 to 19, P35 was obtained from P34 and P15.

Step 3

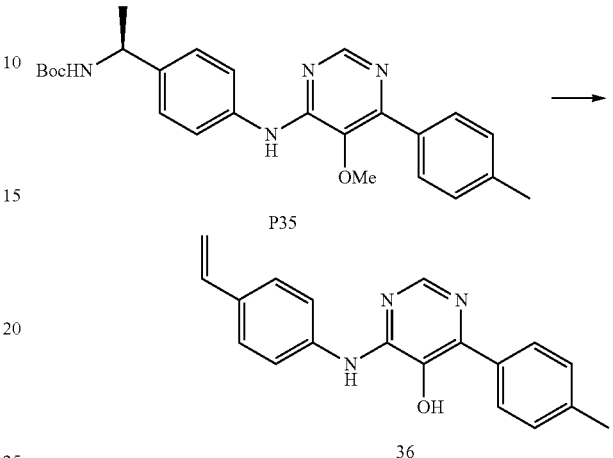

When P35 was subjected to reaction conditions similar to the transformation of 1 to 2, 36 was obtained. LCMS: 304.2 (MH+)

Example 37

4-[[4-(Aminomethyl)phenyl]amino]-2-cyclopropyl-6-(4-methylphenyl)-5-pyrimidinol Step 1

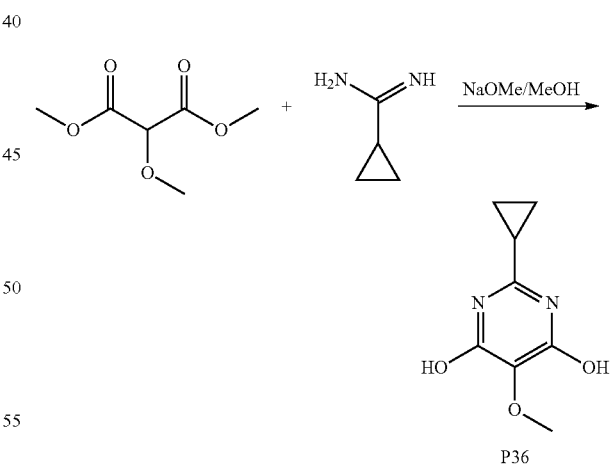

P36

To 17 mL of a 30% weight solution of sodium methoxide in methanol at 0° C. was added 3.65 mL of dimethyl methoxy-malonate and, in portions, 3.34 g of cyclopropanecarboxami-dine hydrochloride. After 30 minutes the mixture was heated to reflux for 1.5 hours then cooled to room temperature. After 16 hours the mixture was cooled to 0° C. and quenched with 8 mL of concentrated aq. HCl. The white precipitate was concentrated by vacuum filtration then dried in a vacuum oven at 50° C. overnight. 3.76 g of P36 was obtained.

Step 2

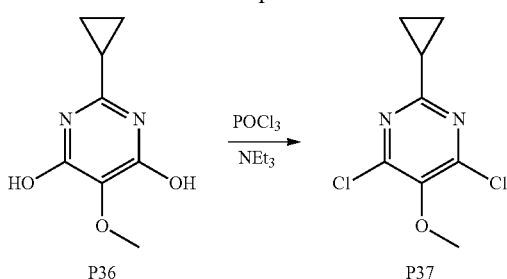

To 3.76 g of P36 in 4 mL of toluene was added 3.2 mL of triethylamine and, at near refluxing, 4.2 mL of phosphorous oxychloride added drop wise. The mixture was then heated to reflux for 2 hours then cooled to room temperature and ice added to the mixture which was stirred until the ice had melted. The phased were separated and the aqueous phase was extracted twice with toluene. The combined organic phases were washed with aq. sodium bicarbonate and brine, dried with magnesium sulfate, filtered and evaporated to dryness yielding 3.85 g of P37.

Step 3

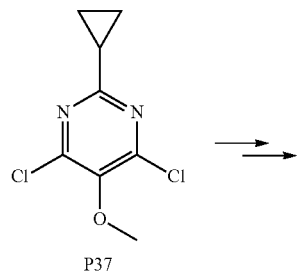

Using procedures analogous to the preparation of example 3, P37 was converted to example 37. LCMS: 347.2 (MH$^+$)

Example 38

4-[[2-Cyclopropyl-5-hydroxy-6-(4-methylphenyl)-4-pyrimidinyl]amino]benzenecarboximidamide

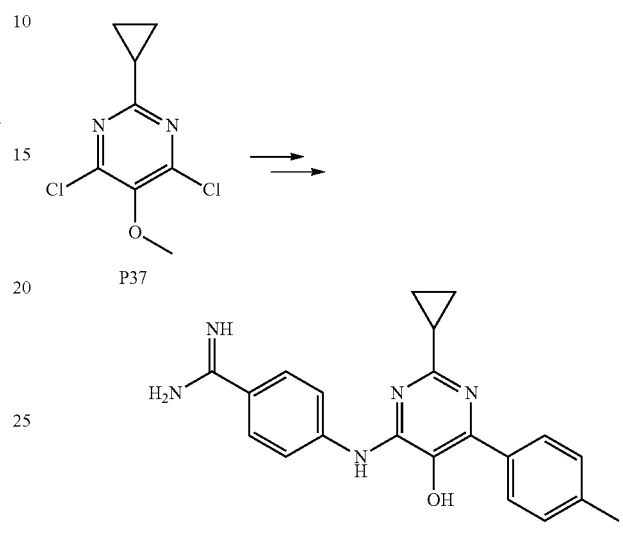

Using procedures analogous to the preparation of example 4, P37 was converted to example 38. LCMS: 360.2 (MH$^+$)

Example 39

2-Fluoro-4-(5-hydroxy-6-p-tolylpyrimidin-4-ylamino)benzonitrile

Step 1:—Dimethyl 2-(benzyloxy)malonate

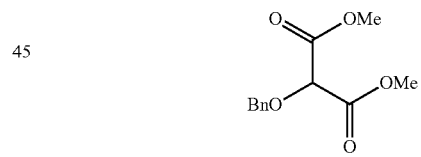

Dimethyl 2-(benzyloxy)malonate was synthesized as reported in Tetrahedron Asymmetry; 12 (2001) p 271-277.

Step 2:—5-(benzyloxy)pyrimidine-4,6-diol

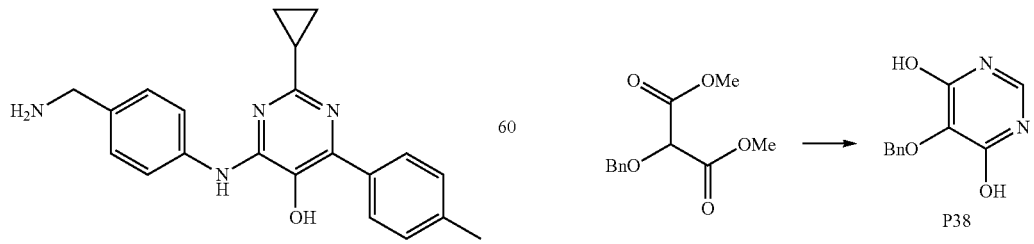

Dimethyl 2-(benzyloxy)malonate (16.1 g, 0.0675 mol) was dissolved in MeOH (27 ml), NaOMe (42.59 ml of a 30% solution in MeOH, 3.5 eq) was added and the mixture cooled to 0 C. Formamidine hydrochloride (5.68 g, 1.05 eq) was added and the mixture stirred at 0° C. for 30 minutes and then at reflux for 2 hours. After cooling to 0° C. concentrated HCl (21 ml) was added and the solid was collected by filtration (washing with cold water 3×20 ml) to give 15.14 g of the title compound.

Step 3:—5-(benzyloxy)-4,6-dichloropyrimidine

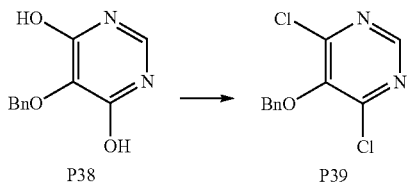

The compound from step 2 (15.14 g, 0.0694 mol) was dissolved in PhMe (70 ml) and Et$_3$N (10.72 ml, 1.1 eq) was added. The solution was heated to 80° C. and POCl3 (13.93 ml, 2.2 eq) was added. Once the addition was complete the mixture was heated at reflux for 2 hours. After cooling to 0° C. the mixture was quenched with ice and extracted with EtOAc. The EtOAc extracts were washed with water, NaHCO$_3$ $_{(sat)}$, dried (MgSO$_4$) and concentrated to give 12.78 g of the title compound.

Step 4:—5-(benzyloxy)-4-chloro-6-p-tolylpyrimidine

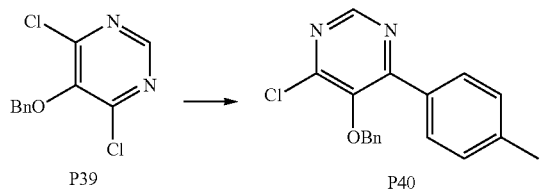 [SMILES: "P39" ; Clc1ncnc(Cl)c1OCc1ccccc1 ; "P40" ; Cc1ccc(-c2ncnc(Cl)c2OCc2ccccc2)cc1]

The compound from step 3 (12.78 g, 0.05 mol) was dissolved in (4:1:1) PhMe/H$_2$O/DME (111 ml). Pd(Ph$_3$P)$_4$ (2.9 g, 0.05 eq), K$_2$CO$_3$, and p-tolylboronic acid (6.81 g, 1 eq) were added, the mixture was degassed and heated at 100° C. overnight. After cooling to room temperature the organic layer was purified by silica gel chromatography (0-10% EtOAc in hexane) to give 5.5 g of the title compound.

Step 5:—4-(5-(benzyloxy)-6-p-tolylpyrimidin-4-ylamino)-2-fluorobenzonitrile

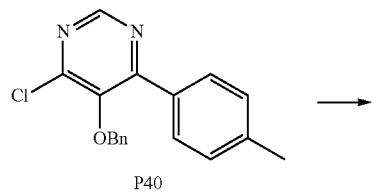

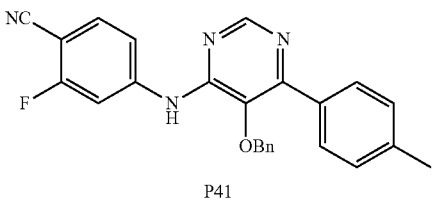

The compound from step 4 (0.3 g, 0.96 mmol) was dissolved in DMF (4.83 ml), 4-cyano-3-fluoroaniline (0.131 g, 1 eq) and NaH (0.155 g of 60% dispersion in mineral oil, 4 eq) were added. After 1 hour LCMS showed complete conversion, the reaction was quenched with NH$_4$Cl$_{(sat)}$ and extracted with EtOAc. The extracts were dried concentrated and the residue purified by silica gel chromatography (0-20% EtOAc in hexane) to give 0.3 g of the title compound.

LCMS MH$^+$=411.

Step 6:—2-fluoro-4-(5-hydroxy-6-p-tolylpyrimidin-4-ylamino)benzonitrile

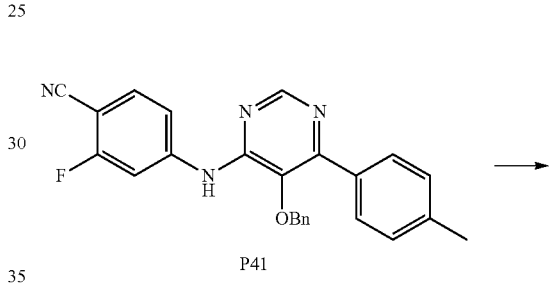

The compound from step 5 (0.3 g, 0.73 mmol) was dissolved in (3:1) MeOH/THF (7.3 ml), 10% Palladium on carbon (30 mg) was added and the mixture placed under H$_2$ (1 atm). After 1 hour LCMS showed that the reaction was complete, the catalyst was removed by filtration and the mixture concentrated to give 200 mg of the title compound. LCMS=321.2 (MH$^+$)

The following compounds were synthesized using analogous procedures.

| Example | Structure | Mol Weight | LCMS (MH+) |
|---|---|---|---|
| 40 | 4-[(3,4-dimethoxyphenyl)amino]-6-(4-methylphenyl)pyrimidin-5-ol | 337.372 | 338.2 |
| 41 | 4-[(4-methoxyphenyl)amino]-6-(4-methylphenyl)pyrimidin-5-ol | 307.346 | 308.2 |
| 42 | 4-[(2,4-dimethoxyphenyl)amino]-6-(4-methylphenyl)pyrimidin-5-ol | 337.372 | 338.2 |
| 43 | 6-(4-methylphenyl)-4-{[4-(trifluoromethoxy)phenyl]amino}pyrimidin-5-ol | 361.318 | 362.2 |
| 44 | 4-({3-chloro-4-(trifluoromethoxy)phenyl}amino)-6-(4-methylphenyl)pyrimidin-5-ol | 395.763 | 396.2 |
| 45 | 6-(4-methylphenyl)-4-{[2-(trifluoromethoxy)phenyl]amino}pyrimidin-5-ol | 361.318 | 362.2 |

-continued
| Example | Structure | Mol Weight | LCMS (MH+) |
|---|---|---|---|
| 46 | 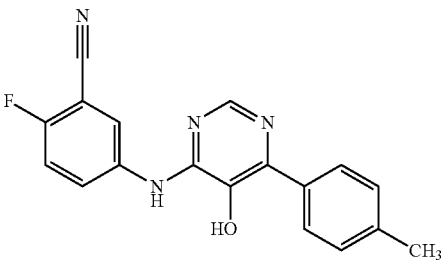 [SMILES: Cc1ccc(-c2ncnc(Nc3ccc(F)c(C#N)c3)c2O)cc1] | 320.32 | 321.2 |
| 47 | 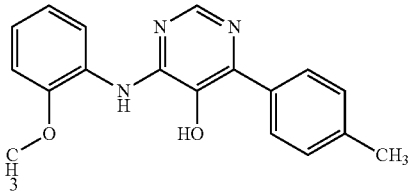 [SMILES: COc1ccccc1Nc1ncnc(-c2ccc(C)cc2)c1O] | 307.346 | 308.2 |
| 48 | 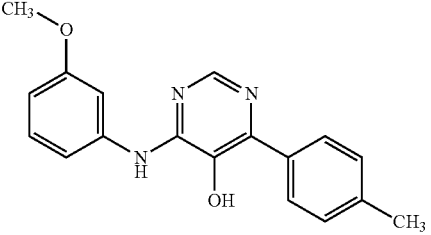 [SMILES: COc1cccc(Nc2ncnc(-c3ccc(C)cc3)c2O)c1] | 307.346 | 308.2 |
| 49 | 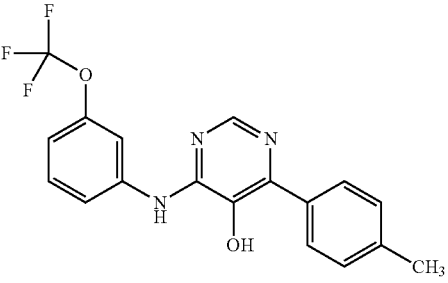 [SMILES: Cc1ccc(-c2ncnc(Nc3cccc(OC(F)(F)F)c3)c2O)cc1] | 361.318 | 362.2 |
| 50 | 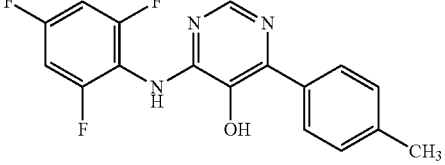 | 331.292 | 332.0 |
| 51 | 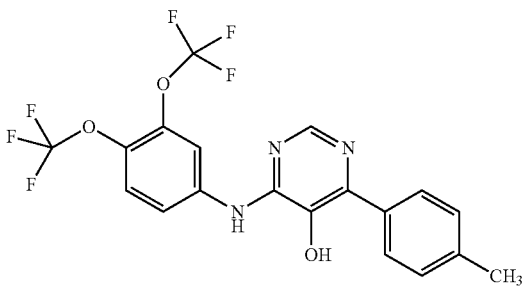 | 445.315 | 446.0 |

-continued

| Example | Structure | Mol Weight | LCMS (MH+) |
|---|---|---|---|
| 52 | 2-chloro-4-[[5-hydroxy-6-(4-methylphenyl)pyrimidin-4-yl]amino]benzonitrile | 336.775 | 337.2 |
| 53 | 3,5-dimethoxy-N-[5-hydroxy-6-(4-methylphenyl)pyrimidin-4-yl]aniline | 337.372 | 338.2 |
| 54 | 2-chloro-5-[[5-hydroxy-6-(4-methylphenyl)pyrimidin-4-yl]amino]benzonitrile | 336.775 | 337.2 |
| 55 | 4-[[6-(4-chlorophenyl)-5-hydroxypyrimidin-4-yl]amino]-2-fluorobenzonitrile | 340.739 | 341.0 |

Example 56

4-(3-Amino-1H-indazol-6-ylamino)-6-p-tolylpyrimidin-5-ol

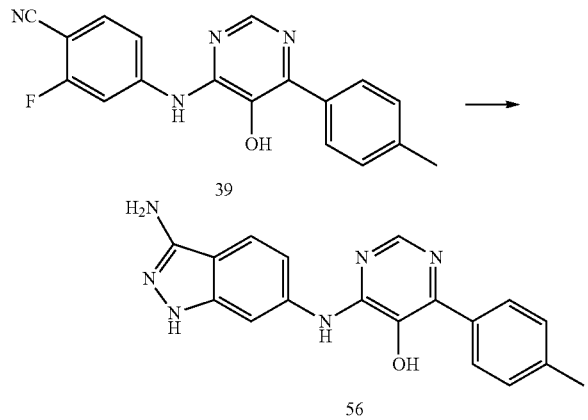

Example 39 (80 mg, 0.25 mmol) was dissolved in BuOH (1.67 ml), hydrazine hydrate (0.785, 100 eq) was added and the mixture heated at 120° C. overnight. After cooling to room temperature the mixture was concentrated and purified by C18 HPLC (89.95:9.95:0.1 H$_2$O:MeCN:HCO$_2$H-9.95:89.95:0.1 H$_2$O:MeCN:HCO$_2$H) to give 52 mg of the title compound. LCMS=333.2 (MH$^+$)

Example 57

4-(3-Amino-1H-indazol-6-ylamino)-6-(4-chlorophenyl)pyrimidin-5-ol

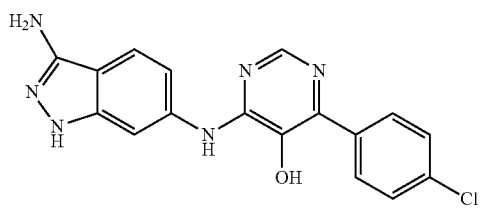

Example 57 was synthesized from 55 in a similar manner to that previously described. LCMS=353.0 (MH$^+$)

Example 58

4-(3-Amino-1H-indazol-5-ylamino)-6-p-tolylpyrimidin-5-ol

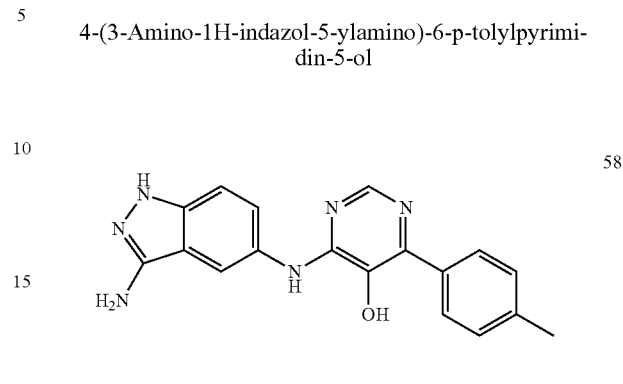

Example 58 was synthesized from 46 in a similar manner to that previously described. LCMS=353.0 (MH$^+$)

Example 59

4-(4-(Aminomethyl)-3-fluorophenylamino)-6-p-tolylpyrimidin-5-ol

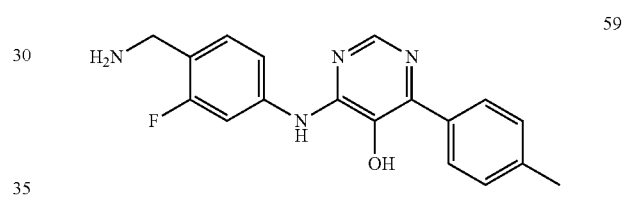

Example 39 (0.047 mg, 0.147 mmol) was dissolved in THF (4.9 ml) to this was added borane dimethylsulfide complex (0.367 ml of a 2M solution in THF, 5 eq) followed by boron trifluoride etherate (0.091 ml, 5 eq). The mixture was then heated at reflux for 6 hours, after cooling to room temperature 6N HCl was added and the mixture heated at reflux for an additional hour and then concentrated under reduced pressure. The residue was purified by C18 HPLC (89.95:9.95:0.1 H$_2$O:MeCN:HCO$_2$H-9.95:89.95:0.1 H$_2$O:MeCN:HCO$_2$H) to give 25 mg of the title compound. LCMS=325.2 (MH$^+$).

The following compounds were synthesized using analogous procedures from the appropriate starting material.

| Example | Structure | Mol Weight | LCMS (MH$^+$) |
|---|---|---|---|
| 60 | 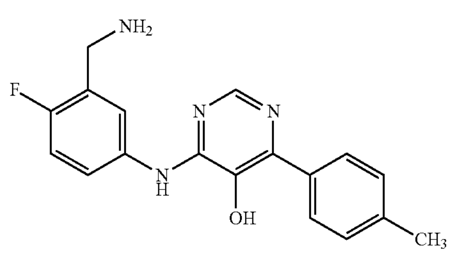 [SMILES: Cc1ccc(-c2ncnc(Nc3ccc(F)c(CN)c3)c2O)cc1] | 324.352 | 325.2 |

-continued

| Example | Structure | Mol Weight | LCMS (MH+) |
|---------|-----------|------------|------------|
| 61 | 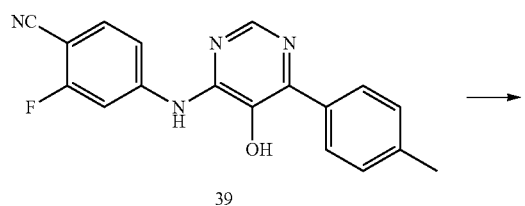 | 340.807 | 341.2 |
| 62 | 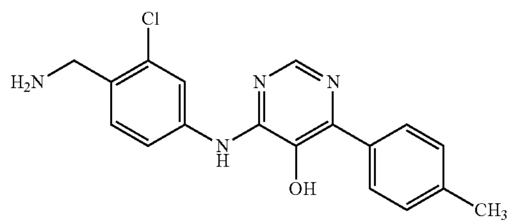 [SMILES: Cc1ccc(-c2ncnc(Nc3ccc(CN)c(Cl)c3)c2O)cc1] | 340.807 | 341.2 |

Example 63

2-Fluoro-4-(5-hydroxy-6-p-tolylpyrimidin-4-ylamino)benzamide

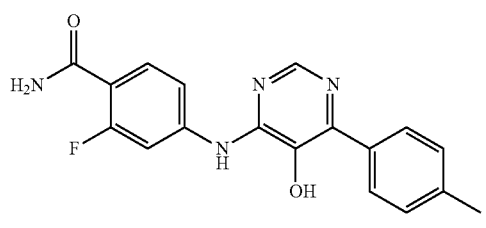

Example 39 (0.075 mg, 0.234 mmol) was dissolved in a 1:1 mixture of EtOH/THF (3.9 ml). A solution of 30% $H_2O_2$ (0.7 ml) was added followed by 3 M NaOH (0.7 ml), the mixture was then stirred for 4 days. The mixture was neutralized with dilute HCl washed with EtOAc to leave an aqueous suspension. The aqueous layer was filtered and the solid dried to give 49 mg of the title compound. LCMS=339.2 (MH+)

Example 64

4-(3-Aminobenzo[d]isoxazol-6-ylamino)-6-p-tolylpyrimidin-5-ol

Step 1:—2-fluoro-44(6-p-tolyl-5-((2-(trimethylsilyl)ethoxy)methoxy)pyrimidin-4-yl)((2-(trimethylsilyl)ethoxy)methyl)amino)benzonitrile

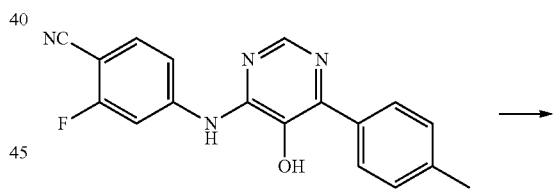

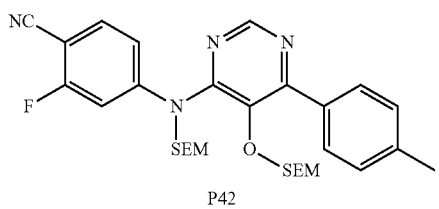

Example 39 (100 mg, 0.312 mmol) was dissolved in DMF, NaH (37.5 mg of a 60% dispersion in mineral oil, 3 eq) was added, 10 minutes later SEMCl (0.131 ml, 2.4 eq) was added and the mixture stirred overnight. The reaction was quenched with $NH_4Cl_{(sat)}$ and extracted with EtOAc. The extracts were dried concentrated and the residue purified by silica gel chromatography (0-20% EtOAc in hexane) to give 0.146 g of the title compound. LCMS=581 (MH+).

Step 2:—4-(3-aminobenzo[d]isoxazol-6-ylamino)-6-p-tolylpyrimidin-5-ol

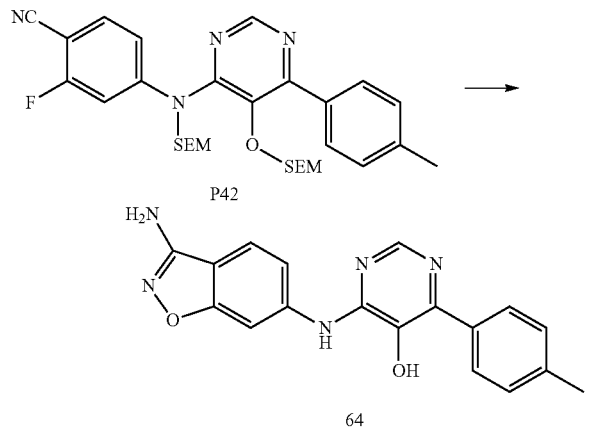

Acetone oxime (23.9 mg, 1.3 eq) and t-BuOK (36.7 mg, 1.3 eq) were mixed together in DMF (1 ml), after stirring for 30 minutes the compound from step 1 (0.146, 0.251 mmol) in DMF (2 ml) was added and the resulting mixture stirred for 1 hour. The mixture was diluted with EtOAc and washed with $H_2O/NH_4Cl_{(sat)}$, dried (MgSO$_4$), and concentrated. The resulting residue was dissolved in 1:1 1N HCl/EtOH and heated at 80° C. for 2.5 hours. The mixture was cooled to room temperature quenched with NaHCO$_{3(sat)}$ and extracted with EtOAc, the extracts were dried (MgSO$_4$) and concentrated to give 31 mg of the title compound.
LCMS=334.2 (MH+)

Example 65

2-Hydroxy-4-(5-hydroxy-6-p-tolylpyrimidin-4-ylamino)benzimidamide

Step 1:—N$^6$-(5-methoxy-6-p-tolylpyrimidin-4-yl)benzo[d]isoxazole-3,6-diamine

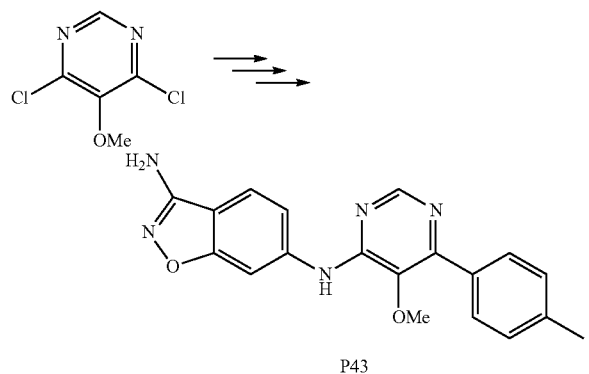

The title compound was synthesized from 4,6-dichloro-5-methoxypyrimidine using procedures described previously.

Step 2:—2-hydroxy-4-(5-hydroxy-6-p-tolylpyrimidin-4-ylamino)benzimidamide

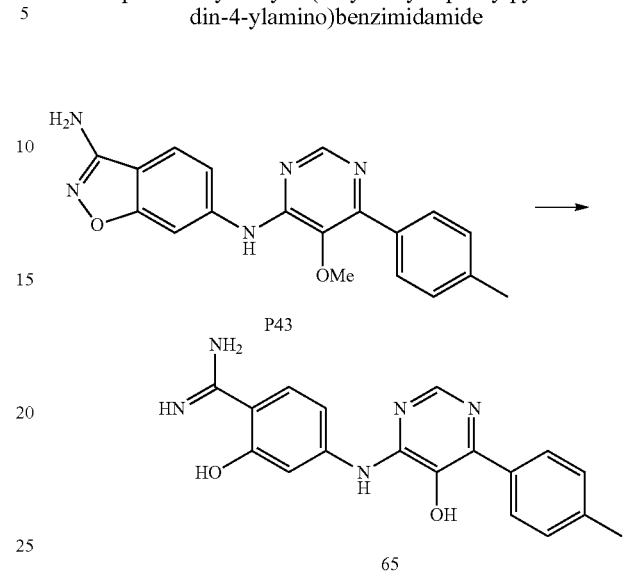

The product from step 1 (75 mg, 0.216 mmol) was dissolved in concentrated (47%) HI$_{(aq)}$ (2.16 ml), Bu$_4$I (16 mg, 0.2 eq) was added and the mixture heated at 130° C. for 30 minutes in a microwave. The mixture was evaporated to dryness and concentrated from EtOH (×2). The residue was purified by C18 HPLC (89.95:9.95:0.1 H$_2$O:MeCN:HCO$_2$H-9.95:89.95:0.1 H$_2$O:MeCN:HCO$_2$H) to give 25 mg of the title compound. LCMS=336.2 (MH+)

Example 66

4-(Benzo[d]oxazol-6-ylamino)-6-p-tolylpyrimidin-5-ol

Step 1:—N-(5-(benzyloxy)-6-p-tolylpyrimidin-4-yl)benzo[d]oxazol-6-amine

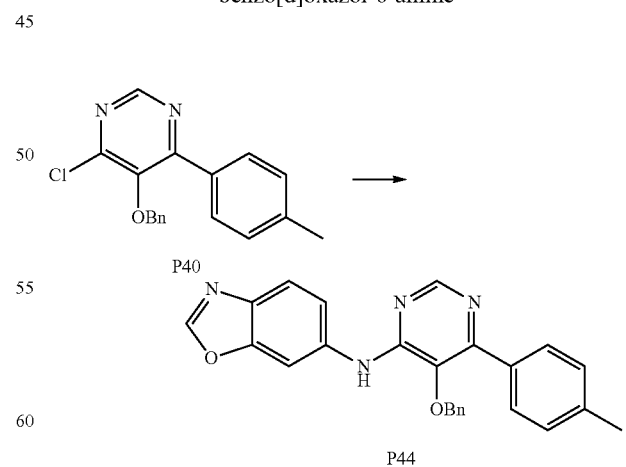

5-(benzyloxy)-4-chloro-6-p-tolylpyrimidine (50 mg, 0.161 mmol) was dissolved in PhMe, to this was added benzo[d]oxazol-6-amine (23.7 mg, 1.1 eq), Pd(dba)$_2$ (4.6 mg, 0.05 eq), t-BuONa (31 mg, 2 eq), and (±)-BINAP (15 mg, 0.15 eq).

The mixture was degassed and heated at 115° C. overnight. The mixture was cooled to room temperature, diluted with EtOAc and washed with H₂O. Preparative TLC gave 17 mg of the title compound.

Step 2:—4-(benzo[d]oxazol-6-ylamino)-6-p-tolylpyrimidin-5-ol

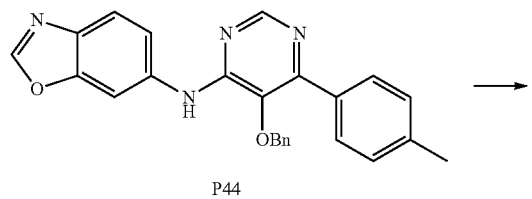

P44

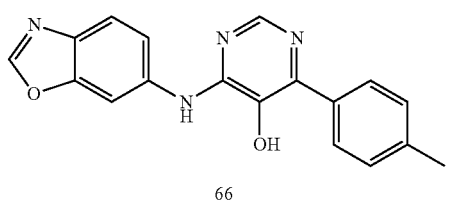

66

The compound P44 17 mg, 0.042 mmol) was dissolved in MeOH (4 ml), 10%
Palladium on carbon (5 mg) was added and the mixture placed under H₂ (1 atm). After 1.5 hour LCMS showed that the reaction was complete, the catalyst was removed by filtration and the mixture concentrated to give 10 mg of the title compound. LCMS=319.2 (MH⁺)

Example 67

4-(6-chloro-1H-benzo[d]imidazol-2-ylamino)-6-p-tolylpyrimidin-5-ol

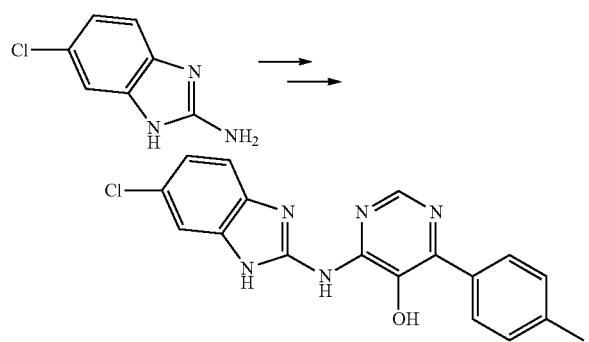

67

Example 67 was synthesized in an analogous manner to 66 using 6-chloro-1H-benzo[d]imidazol-2-amine. LCMS=352.2 (MH⁺)

Example 68

4-[[4-(1(S)-Aminoethyl)phenyl]amino]-6-(4-methylphenyl)-5-pyrimidinol

Step 1

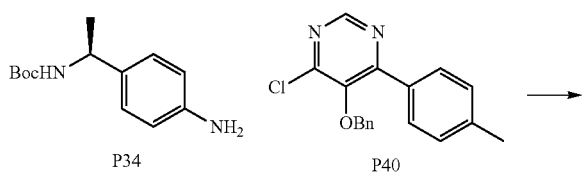

P34        P40

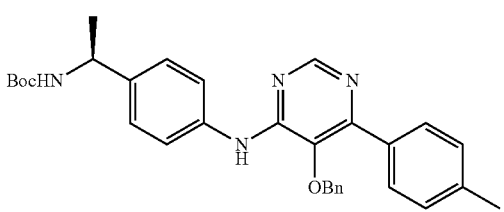

P45

P34 coupled with P40 using a procedure similar to the transformation of P19 to P20.

Step 2

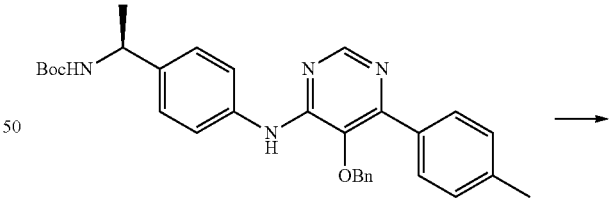

P45

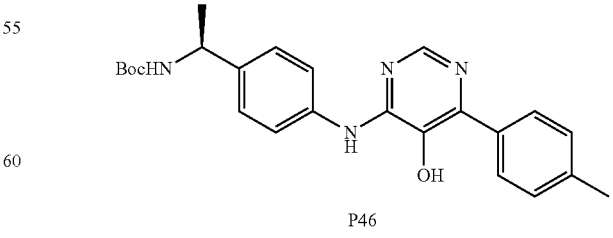

P46

A suspension of 80 mg of P45 and 12 mg of 10% Pd—C in 5 ml ethyl acetate was stirred under hydrogen balloon for 2 hr at which time additional 10 mg of the catalyst was added and stirred for another 2 hr. It was filtered through a CELITE pad and concentrated to provide 60 mg of P46.

Step 3

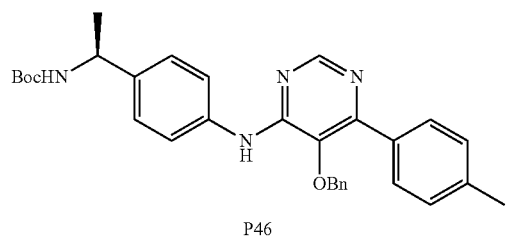

P46

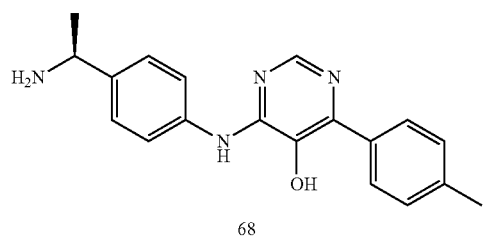

68

A solution of 60 mg of P46 in 1 ml each of TFA and DCM was stirred at 0° C. for 1.5 hr, concentrated then added HCl in ether to provide 58 mg of 68. LCMS: 321.2 (MH$^+$)

Example 69

4-[[4-(1(R)-Aminoethyl)phenyl]amino]-6-(4-methylphenyl)-5-pyrimidinol

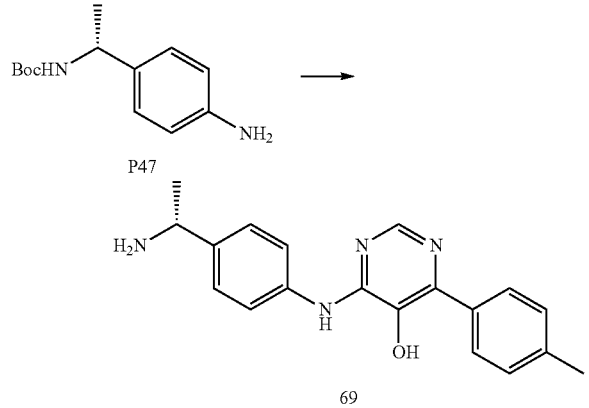

P47 was prepared using a procedure similar to the preparation of P34 and converted to 69 using a procedure similar to the preparation of 68. LCMS: 321.2 (MH$^+$)

Example 70

4-[[6-(Aminomethyl)-3-pyridinyl]amino]-6-(4-methylphenyl)-5-pyrimidinol

Step 1

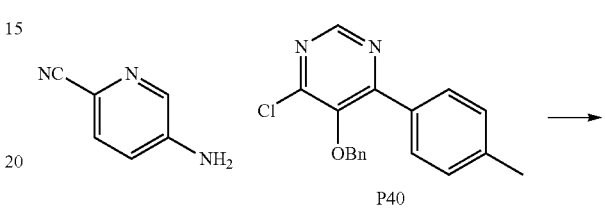

P40

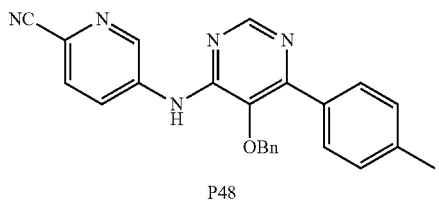

P48

P40 converted to P48 using a procedure similar to the preparation of 19.

Step 2

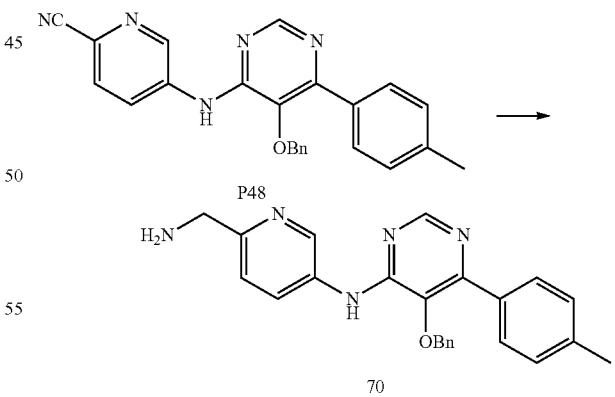

70

A suspension of 350 mg of P48 and 60 mg of 10% Pd—C in 5 ml each of THF and MeOH was stirred under hydrogen balloon. After 3 hr, additional 50 mg of catalyst was added and the mixture stirred overnight. It was filtered through a CELITE pad, concentrated and purified by RPHPLC to provide 51 mg of 70.

LCMS: 308.2 (MH$^+$)

Example 71

4-[[5-HYDROXY-6-(4-METHYLPHENYL)-4-PYRIMIDINYL]AMINO]BENZAMIDE

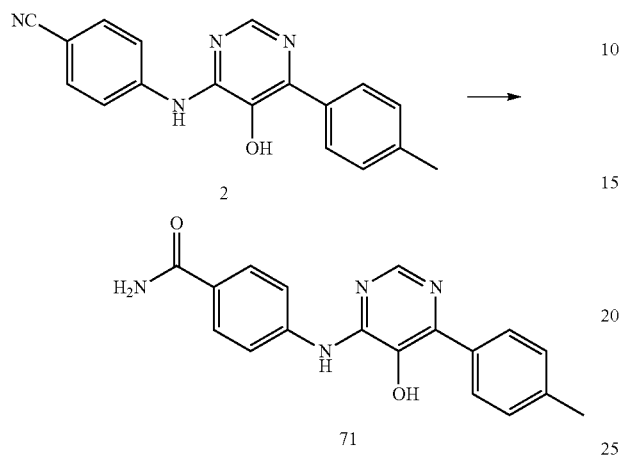

A mixture of 2 (90 mg, 0.30 mmol) and KOH (85 mg, 1.52 mmol, 5 eq.) in 1 ml each of THF, MeOH and water in a sealed tube was stirred overnight at 110° C. The mixture was purified by RP-HPLC to provide 18 mg of 71. LCMS: 321.2 (MH+)

Example 72

4-[[4-(Aminomethyl)phenyl]amino]-6-(3-methylphenyl)-5-pyrimidinol

Step 1

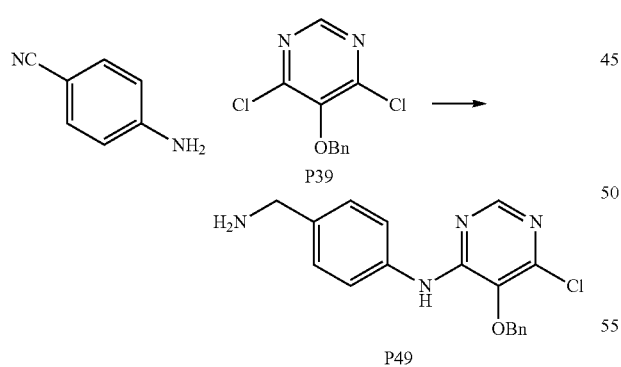

To a solution of 4-aminobenzonitrile (3.0 g, 11.76 mmol) in 30 ml DMF at rt was added a 60% suspension of sodium hydride in mineral oil and stirred for 10 min. It was cooled to 0° C. then P39 was added in one portion. The mixture was stirred at rt for 1 hr, quenched with aq. NH₄Cl and extracted 3× with ethyl acetate. The combined organic layer was washed with brine, dried over MgSO₄, filtered, concentrated and purified flash chromatography using 1:1:3 ethyl acetate-dichloromethane-hexanes to provide 820 mg of P49.

Step 2

P50 was prepared from P49 and m-tolylboronic acid using a procedure similar to the preparation of 1.

Step 3

A mixture of 75 mg of P50, ~75 mg of $R^a$—Ni and 10 mg of 10% Pd—C in 3 ml of 7N NH₃ in methanol solution was stirred under a hydrogen balloon for 1 hr. It was filtered, concentrated and purified by RP-HPLC to provide 24 mg of 72.

LCMS: 307.2 (MH+)

The following examples were prepared in a similar manner.

| Cpd# | Structure | LCMS (MH+) |
|---|---|---|
| 73 | 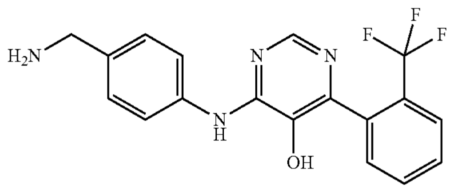 [SMILES: NCc1ccc(Nc2ncnc(-c3ccccc3C(F)(F)F)c2O)cc1] | 361.2 |
| 74 | 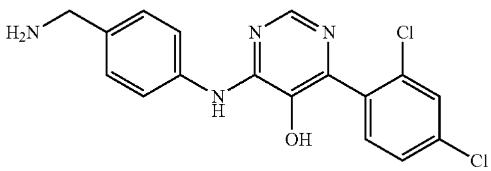 [SMILES: NCc1ccc(Nc2ncnc(-c3ccc(Cl)cc3Cl)c2O)cc1] | 361.2 |
| 75 | 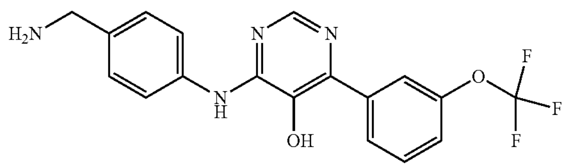 [SMILES: NCc1ccc(Nc2ncnc(-c3cccc(OC(F)(F)F)c3)c2O)cc1] | 377.2 |
| 76 | 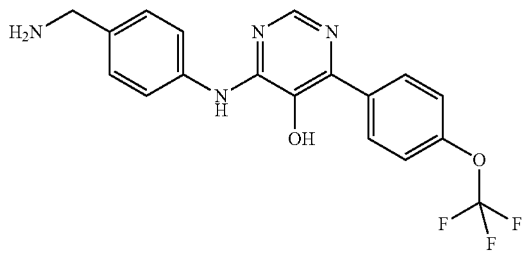 [SMILES: NCc1ccc(Nc2ncnc(-c3ccc(OC(F)(F)F)cc3)c2O)cc1] | 377.2 |

Example 77

2,3-Dihydro-5-[[5-hydroxy-6-(4-methylphenyl)-4-pyrimidinyl]amino]-1h-inden-1-one

Step 1

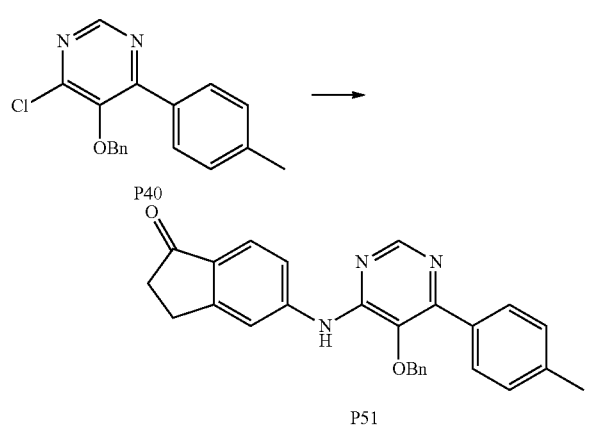

Compound P40 (34 mg, 0.11 mmol), 5-amino-2,3-dihydro-1H-inden-1-one (29 mg, 0.20 mmol), cesium carbonate (89 mg, 0.27 mmol), Pd$_2$(dba)$_3$ (9 mg, 0.01 mmol), and racemic BINAP (8 mg, 0.01 mmol) were combined in toluene (1 mL). The mixture was purged with nitrogen and stirred at 130° C. for 16 h. The mixture was filtered, washed with EtOAc, and concentrated in vacuo. The residue was separated on a silica gel cartridge (eluting with acetone in DCM (0-20%) to give compound P51 as a tan solid (26 mg, 56% yield).

Step 2

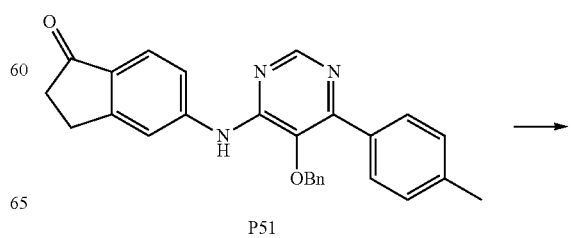

-continued

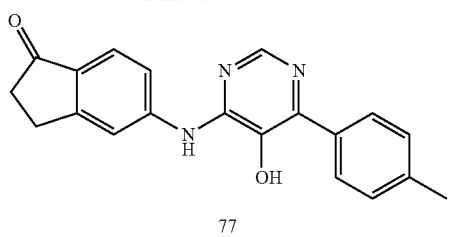

77

Compound P51 was stirred over 10% Pd/C in MeOH under a hydrogen atmosphere at room temperature for 2 h. The mixture was filtered and concentrated in vacuo to give compound 77 as a yellow solid (100%). LCMS: 332.2 (MH+).

Example 78

4-[(2,3-Dihydro-1-hydroxy-1h-inden-5-yl)amino]-6-(4-methylphenyl)-5-pyrimidinol

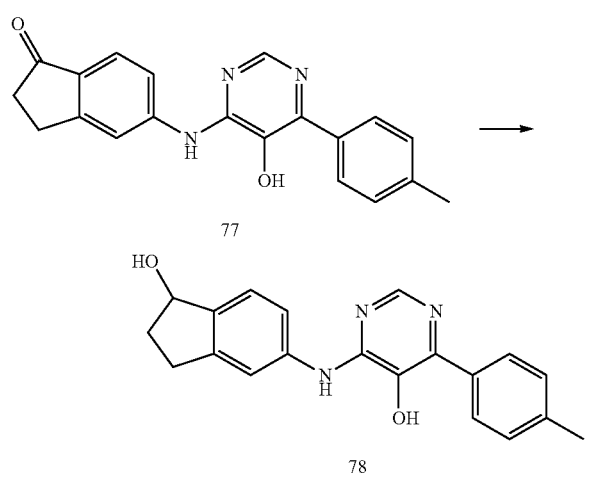

The ketone 77 was reduced in a conventional way with NaBH₄ in MeOH at room temperature to give the alcohol 78 as a yellow solid. LCMS: 334.2 (MH+).

Example 79

(1E)-2,3-Dihydro-5-[[5-hydroxy-6-(4-methylphenyl)-4-pyrimidinyl]amino]-1h-inden-1-one oxime

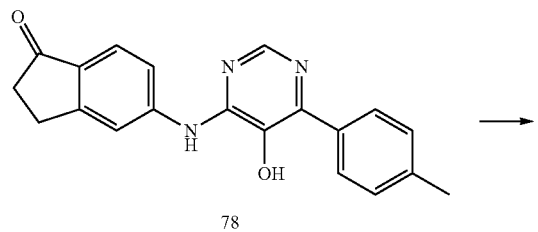

-continued

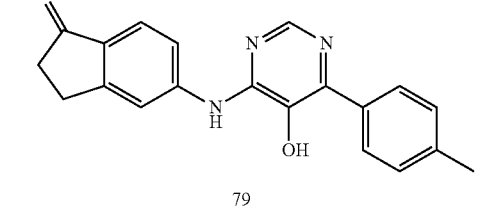

79

The ketone 78 was treated in a conventional way with hydroxylamine hydrochloride in pyridine at room temperature to give the oxime 79 as a yellow solid. LCMS: 347.2 (MH+).

Example 80

4-[(1-Amino-2,3-dihydro-1h-inden-5-yl)amino]-6-(4-methylphenyl)-5-pyrimidinol

Step 1

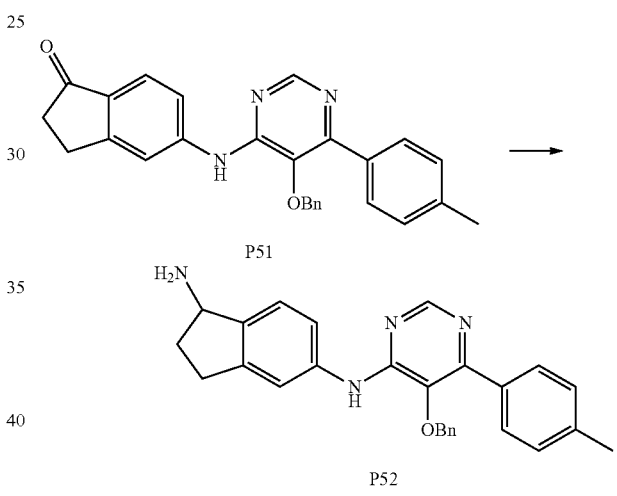

Compound P51 (13 mg, 0.031 mmol) and ammonium acetate (0.10 g, 1.4 mmol) were stirred in i-PrOH (1.5 mL) at room temperature for 1 h. Sodium cyanoborohydride (11 mg, 0.18 mmol)) was added and heated at 100° C. for 4 h. The mixture was quenched with saturated NH₄Cl and washed with DCM. The organic layer was dried (MgSO₄) and concentrated in vacuo. The residue was separated on a preparative TLC plate (5% 2N NH₃/MeOH in DCM) to give compound P52 as a clear resin.

Step 2

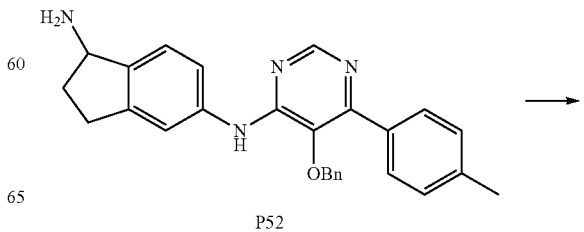

-continued

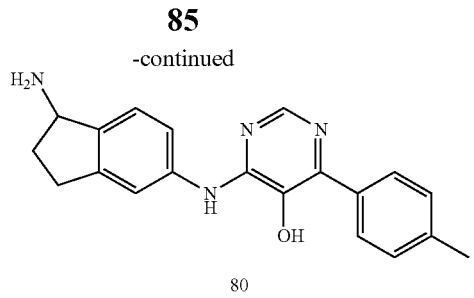
80

Compound P52 was converted to compound 80 in a similar fashion as the preparation of compound 77. LCMS: 333.2 (MH$^+$).

Example 81

4-[(1-Amino-6-isoquinolinyl)amino]-6-(4-methylphenyl)-5-pyrimidinol

Step 1

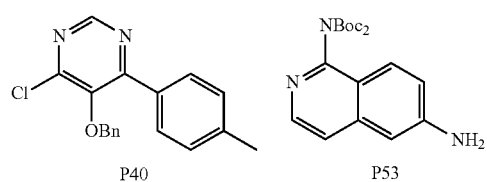

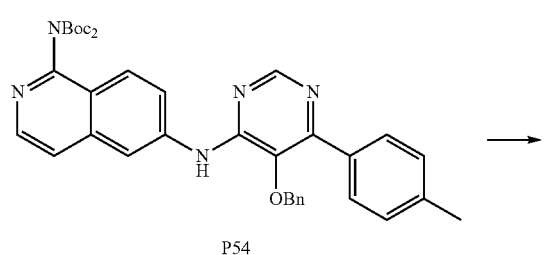
P54

Compound P40 was converted to compound P54 in a similar fashion as preparation of compound P51, using aniline P53 (prepared as shown in WO 2007002313).

Step 2

-continued

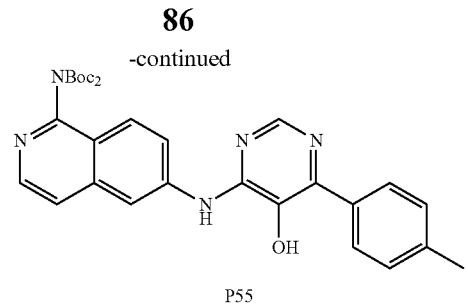
P55

Compound 54 was converted to compound 55 in a similar fashion as

Preparation of Compound 77 from P51

Step 2

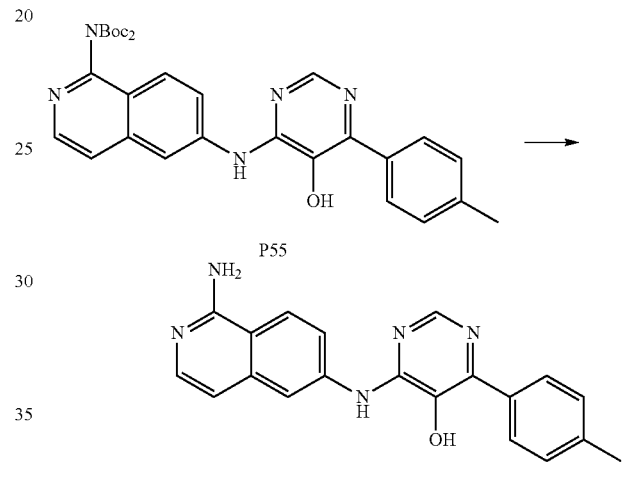

Compound P55 was deprotected with trifluoroacetic acid in DCM at room temperature. Concentration in vacuo followed by purification with reverse phase HPLC gave compound 81 formate as a yellow solid. LCMS: 344.2 (MH$^+$).

Example 82

4-[(1-Amino-5-chloro-6-isoquinolinyl)amino]-6-(4-methylphenyl)-5-pyrimidinol

Step 1

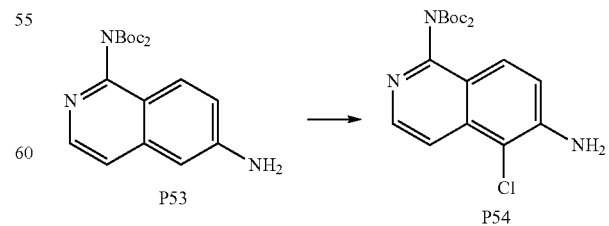

Compound P53 (0.10 g, 0.26 mmol) and N-chlorosuccinimide (0.038 g, 0.28 mmol) were stirred in DMF (2 mL) at room temperature for 2 h. The mixture was concentrated in vacuo. The residue was separated on a silica gel cartridge (eluting with EtOAc in hexanes (0→50%) to give compound P54 (0.06 g).

Using a procedure similar to the transformation of P40 to P51, P53 was coupled with P39 to obtain P55.

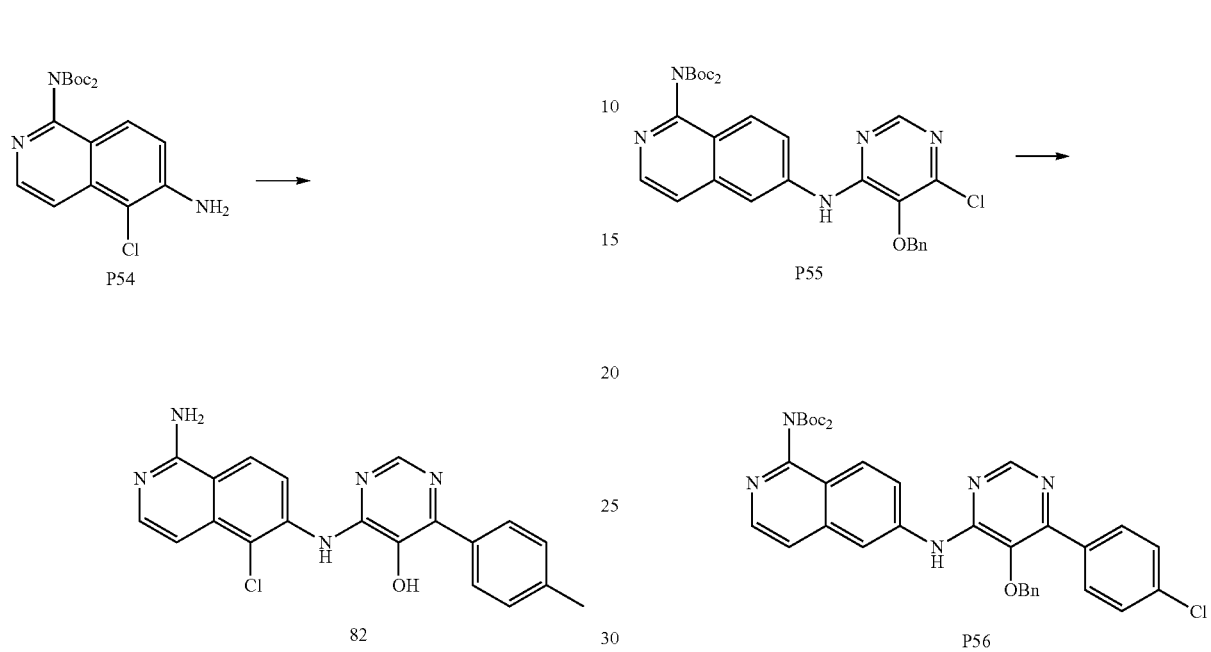

Compound P54 was converted to compound 82 in a similar fashion as Preparation of Compound 81 from P53. LCMS: 378.2 (MH+).

Compound P55 was converted to compound P56 by a conventional Suzuki coupling method.

Example 83

4-[(1-AMINO-6-ISOQUINOLINYL)AMINO]-6-(4-CHLOROPHENYL)-5-PYRIMIDINOL

Step 1

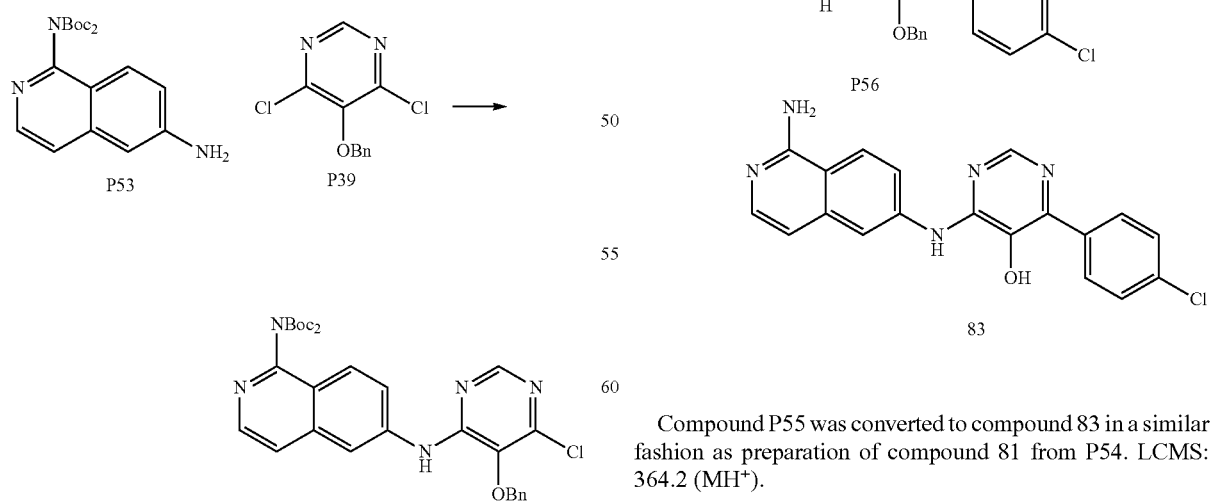

Compound P55 was converted to compound 83 in a similar fashion as preparation of compound 81 from P54. LCMS: 364.2 (MH+).

The following compounds were prepared from compound P55 using the method described above and using the appropriate boronic acid:

| Cpd. No. | Structure | LCMS (MH+) |
| --- | --- | --- |
| 84 | 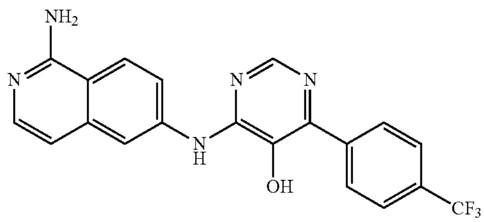 [SMILES: Nc1nccc2cc(Nc3ncnc(-c4ccc(C(F)(F)F)cc4)c3O)ccc12] | 398.2 |
| 85 | 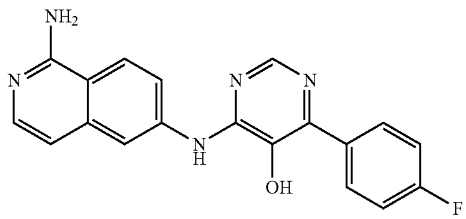 [SMILES: Nc1nccc2cc(Nc3ncnc(-c4ccc(F)cc4)c3O)ccc12] | 348.2 |

Preparative Example P57

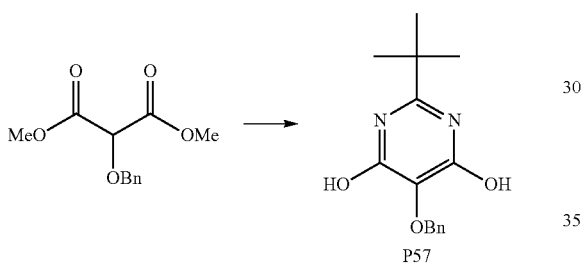

P57

To a solution of dimethyl 2-(benzyloxy)malonate (7.0 g, 29 mmol) in MeOH (27 mL) at 0° C. was added NaOMe (5.5 g, 0.10 mol) portion wise over approximately 10 min. Tert-butylcarbamidine hydrochloride (4.23 g, 31 mmol) was then added portion wise over approximately 15 min and the resulting mixture was stirred for 30 min at 0° C. The mixture was affixed with a reflux condenser, heated to 85° C., and was stirred for 3.5 h. The mixture was cooled to 0° C., treated with conc. HCl (~0.10 mL), and stirred for 15 min. The resultant yellow solid was filtered off thru a medium glass-sintered funnel and was washed with cold water (3×15 mL). The solid was dried in a vacuum oven at 35° C. for 12 h to afford 5.8 g (73% yield) of an off-white solid which was used without further purification. LC-MS: M+H=275.2

Preparative Example P58

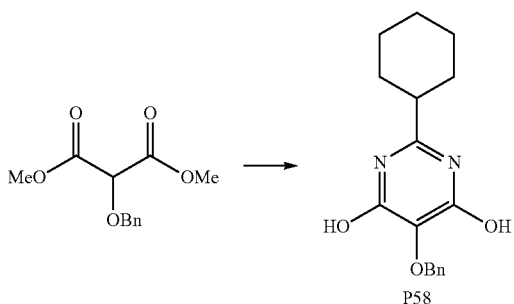

P58

Utilizing the procedure set forth in Preparative Example 2, dimethyl 2-(benzyloxy)malonate (7.0 g, 29 mmol) was treated with NaOMe (5.5 g, 0.10 mol) and cyclohexylcarboxamidine hydrochloride (5.0 g, 31 mmol) to afford 7.0 g (79% yield) of a light yellow solid which was used without further purification. LC-MS: M+H=301.2.

Preparative Example P59

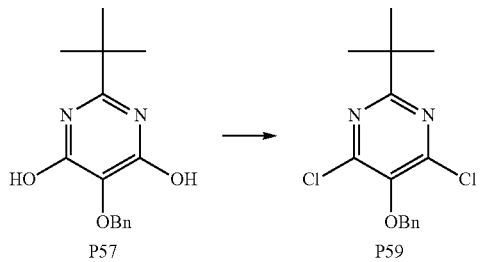

P57 → P59

To a solution of P57 (5.7 g, 20.7 mmol) from in toluene (40 mL) was added Et₃N (3.2 mL, 22.8 mmol). The mixture was affixed with a reflux condenser and was heated to 100° C. POCl₃ (4.3 mL, 46 mmol) was added drop wise over five minutes and the mixture was heated to 125° C. The mixture was stirred for 2.5 h, cooled to 0° C., and treated with ice (~20 g). The mixture was allowed to stir for 20 min while warming to rt. The layers were separated and the aqueous layer was extracted with toluene (2×15 mL). The organic layers were combined and were washed sequentially with sat. aq. NaHCO₃ (1×20 mL) and brine (1×20 mL). The organic layer was dried (Na₂SO₄), filtered, and concentrated to afford 5.1 g (79% yield) of an orange oil that was used without further purification. LC-MS: M+H=311.1.

Preparative Example P60

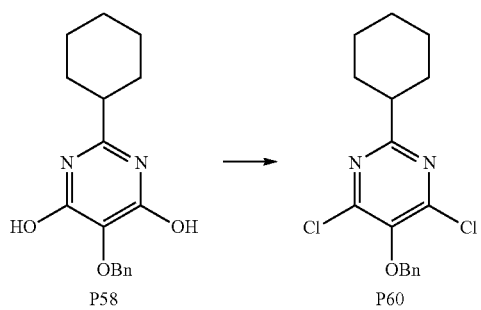

Utilizing the procedure set forth in Preparative Example P59, treatment of P58 (5.7 g, 19 mmol) with Et₃N (2.9 mL, 21 mmol) and POCl₃ (4.0 mL, 42.0 mmol) afforded 5.0 g (78% yield) of a yellow semisolid which was used without further purification. LC-MS: M+H=337.

Preparative Example P61

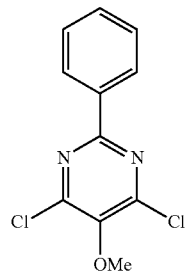 [SMILES: COc1c(Cl)nc(-c2ccccc2)nc1Cl]

The title compound was prepared according to the procedure set forth in US2005/046652.

Preparative Example P62

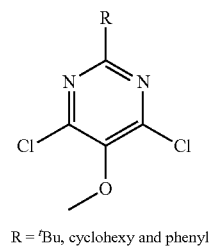

R = ᵗBu, cyclohexy and phenyl

Using a procedure, similar to the preparation of P15, Preparative Examples P62-P64 were prepared by coupling the appropriate pyrimidine chloride with p-tolylboronic acid.

TABLE 1

| Starting Reagent | Product | cmpd 1) yield (%) 2) LC-MS (M + H) |
|---|---|---|
| 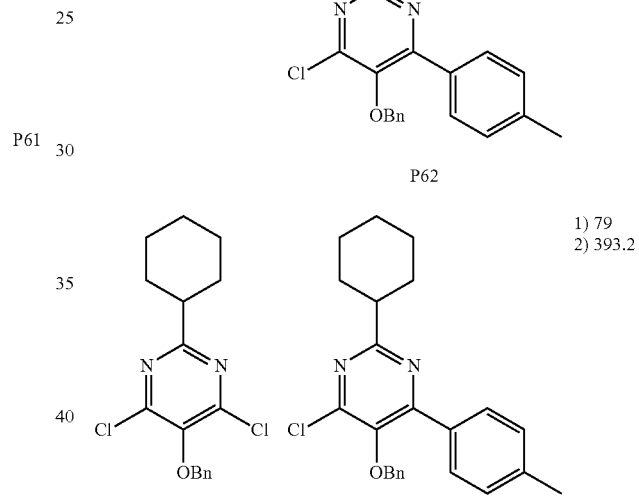 | | 1) 89 2) 367.2 |
| | | 1) 79 2) 393.2 |
| 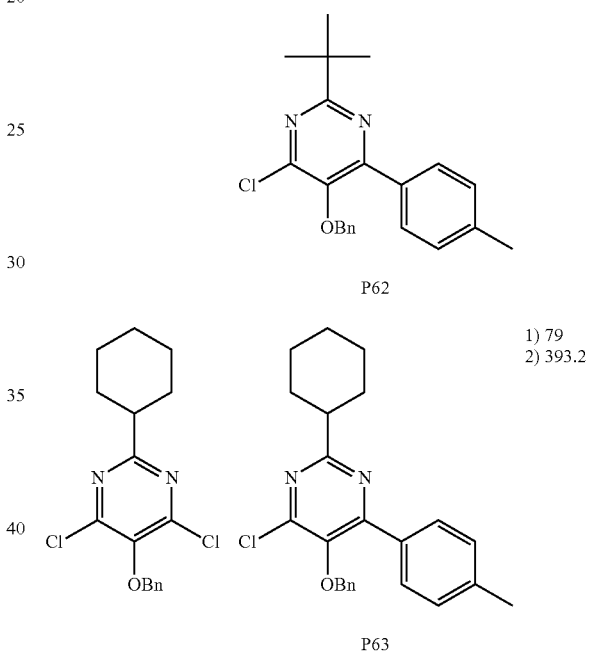 | | |
| 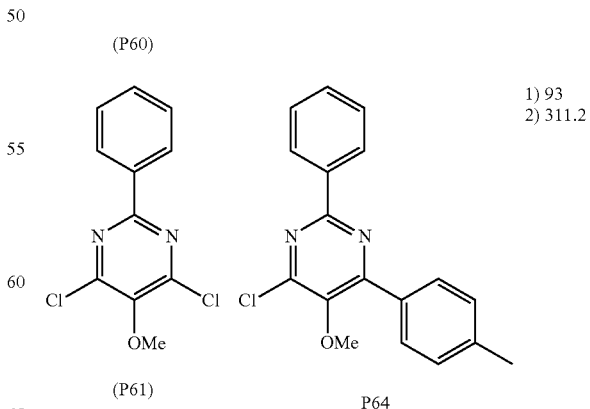 | | 1) 93 2) 311.2 |

Example 86

1,1-Dimethylethyl 4-[[5-methoxy-6-(4-methylphenyl)-4-pyrimidinyl]amino]-1-piperidinecarboxylate

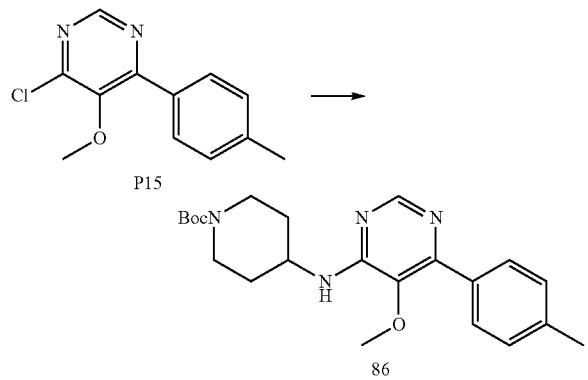

To a solution of P15 (0.14 g, 0.60 mmol) in n-BuOH (3 ml) at rt was added Et$_3$N (0.42 ml, 3 mmol) followed by 4-amino-1-Bocpiperidine (0.18 g, 0.89 mmol). The mixture was affixed with a condenser and was heated to 115° C. The mixture was stirred for 14 h whereupon an additional portion of amine (100 mg, 0.5 mmol) and stirred for 8 h. The mixture was cooled to rt, concentrated under reduced pressure, and placed under high vacuum. The crude material was purified by preparative thin-layer chromatography eluting with 30:1 CH$_2$Cl$_2$/MeOH to afford 0.16 g (67% yield) of 86. LCMS=399.2 (MH$^+$)

By essentially the same procedure set forth in Example 86, only substituting the amines of Table 2 and reacting with chlorides P15 or P64.

TABLE 2

| Example | Amines | Products | cmpd 1) yield (%) 2) LC-MS (M + H) |
|---------|--------|----------|-----------------------------------|
| 87 | BocHN-cyclohexyl-CH$_2$-NH$_2$ | BocHN-cyclohexyl-CH$_2$-NH-pyrimidine-OMe-tolyl | 1) 66  2) 427.3 |
| 88 | H$_2$N-tetrahydrobenzothiazole-NH$_2$ | H$_2$N-tetrahydrobenzothiazole-NH-pyrimidine-OMe-tolyl | 1) 90  2) 368.2 |
| 89 | BocHN-cyclohexyl-NH$_2$ | BocHN-cyclohexyl-NH-pyrimidine-OMe-tolyl | 1) 60  2) 413.3 |

TABLE 2-continued

| Example | Amines | Products | cmpd 1) yield (%) 2) LC-MS (M + H) |
|---|---|---|---|
| P65 | (structure) | (structure) | 1) 9  2) 444.2 |

Example 90

4-(4-Methylphenyl)-6-(4-piperidinylamino)-5-pyrimidinol

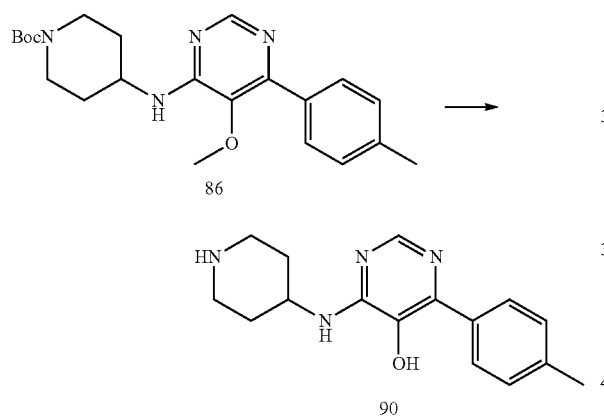

To a solution of 5-methoxypyrimidine (0.13 g, 0.33 mmol) from Example 1 in $CH_2Cl_2$ (1.5 ml) at 0° C. was added $BBr_3$ (1.49 ml, 1.0 M soln in $CH_2Cl_2$) drop wise. The mixture was allowed to warm to rt and stir for 14 h whereupon the mixture was treated with $H_2O$ (3 mL). The mixture was stirred for 30 min and the resultant solid was filtered off and placed under high vacuum. The crude material was purified by reverse phase HPLC(C18 column: 95:5 $H_2O:CH_3CN$ (w/0.1% TFA) to 90:10 $CH_3CN:H_2O$) to afford 84 mg (70% yield) of light orange solid as the TFA salt. LC-MS: M+H (-TFA)=285.2.

Examples 91-99

By essentially the same procedure set forth in Preparative Example 6 only substituting the precursor adducts, the corresponding products were made in Table 3:

TABLE 3

| Example | Precursor | Product | cmpd 1) yield (%) 2) LC-MS (M + H) |
|---|---|---|---|
| 91 (87) | (structure) | (structure) | 1) 35  2) 427.3 |

TABLE 3-continued

| Example | Precursor | Product | cmpd 1) yield (%) 2) LC-MS (M + H) |
|---|---|---|---|
| 92 | (88) | | 1) 18 2) 354.2 |
| 93 | (P65) | | 1) 80 2) 430.2 |

Preparative Example P66

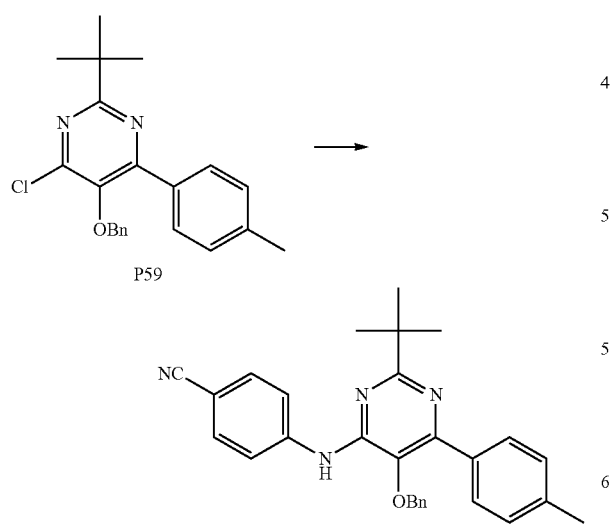

To a solution of 4-aminobenzonitrile (97 mg, 0.82 mmol) in THF (4.5 mL) at 0° C. was added NaH (78 mg, 3.27 mmol) and the mixture was stirred for 15 min. P59 (0.30 g, 0.82 mmol) was added in one portion and the mixture was stirred at rt for 12 h. The mixture was cooled to 0° C. and was treated with water (3 mL) followed by dilution with EtOAc (9 mL). The layers were separated and the aqueous layer was extracted with EtOAc (2×9 mL) and the organic layers were combined. The organic layer was washed with brine (1×5 mL), dried (Na$_2$SO$_4$), filtered and concentrated under reduced pressure. The crude product was purified by flash chromatography using a 50:1 mixture of CH$_2$Cl$_2$/MeOH as eluent to afford 0.27 g (73% yield) of the title compound as a yellow solid. LC-MS: M+H=449.2.

Preparative Example P67, P68

By essentially the same procedure set forth in Preparative Example P66 except utilizing the chloro adduct indicated, the products in Table 4 were prepared:

TABLE 4

| Starting Reagent | Product | cmpd 1) yield (%) 2) LC-MS (M + H) |
|---|---|---|
| (P64) | (P67) | 1) 87 2) 393.2 |
| (P63) | (P68) | 1) 71 2) 475.3 |

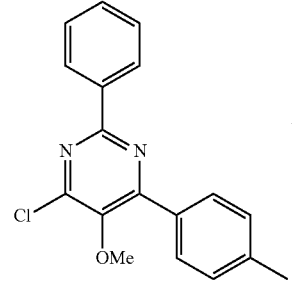 [SMILES: COc1c(Cl)nc(-c2ccccc2)nc1-c1ccc(C)cc1]

Example 94

N-[5-Methoxy-6-(4-methylphenyl)-4-pyrimidinyl]-7-isoquinolinamine

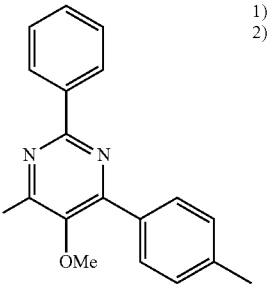

Using a procedure analogous to the one outlined for P66, 7-aminoquinoline (0.15 g, 1.05 mmol) was treated with NaH (0.18 g, 4.4 mmol) in the presence of P15 (0.30 g, 1.2 mmol) to afford 0.20 g (59% yield) of an orange solid. LC-MS: M+H=343.2.

Example 95

4-[[2-Cyclohexyl-5-hydroxy-6-(4-methylphenyl)-4-pyrimidinyl]amino]benzonitrile

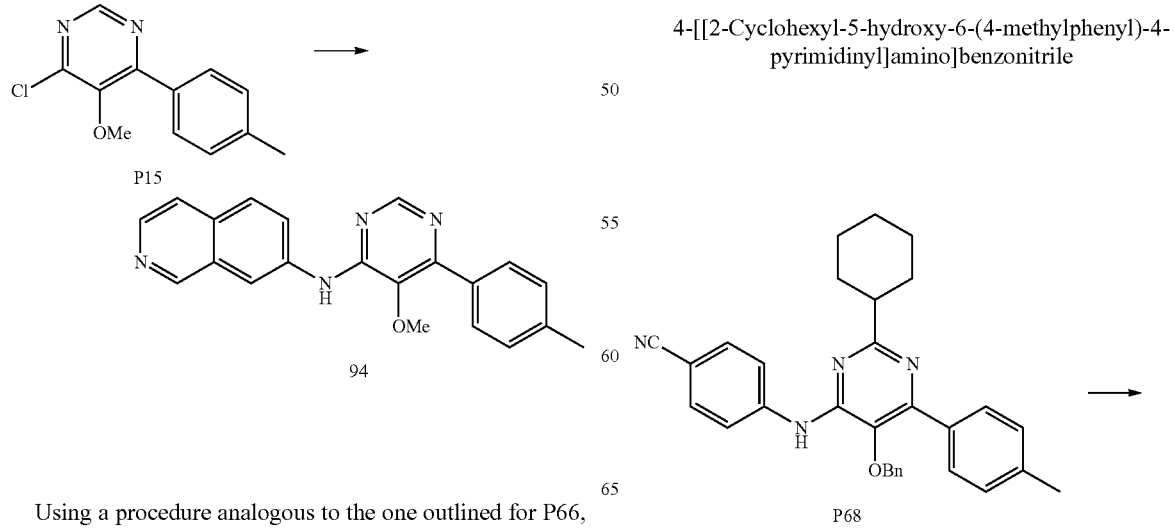

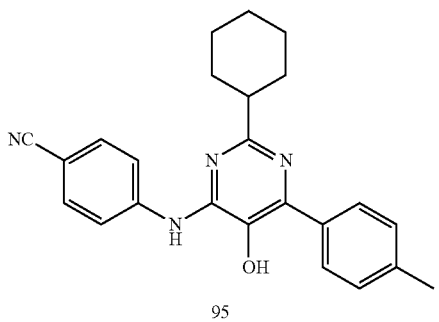

95

To a solution of P68 (0.43 g, 0.91 mmol) in MeOH/THF (2:1; 25 ml total) at rt was added 10% Pd/C (40 mg). The mixture was degassed and filled with $N_2$ followed by repeating the procedure except filling with $H_2$. The mixture was stirred for 1 h under a $H_2$ balloon and was filtered through a pad of CELITE. The CELITE pad was washed with the MeOH/THF (4:1; 100 ml total) and the resultant filtrate was concentrated under reduced pressure and placed under high vacuum to afford 0.35 g (99% yield) of a light yellow solid. LC-MS: M+H=385.2. This material was used without further purification.

Example 96

4-[[2-(1,1-Dimethylethyl)-5-hydroxy-6-(4-methylphenyl)-4-pyrimidinyl]amino]benzonitrile

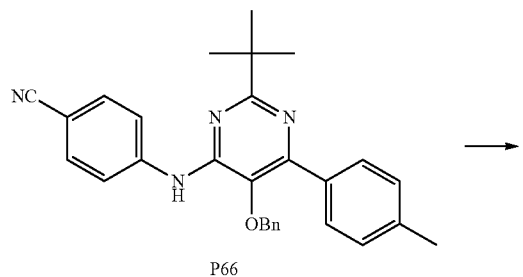

P66

Using the procedure outlined in example 95, P66 (0.43 g, 0.96 mmol) from was converted to 0.33 g (99% yield) of the title compound as a yellow solid which was used without further purification. LC-MS: M+H=359.5.

Example 97

4-[[5-Hydroxy-6-(4-methylphenyl)-2-phenyl-4-pyrimidinyl]amino]benzonitrile

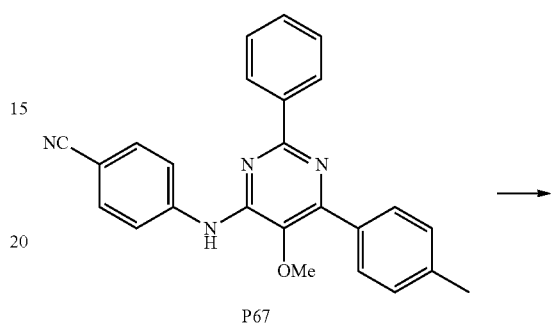

P67

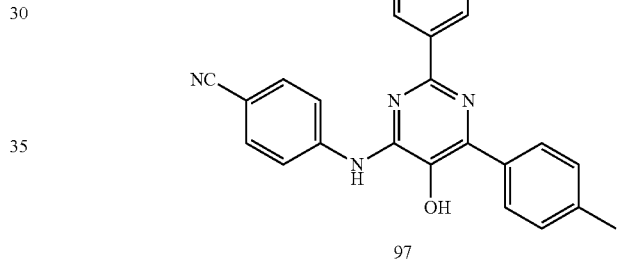

97

Treatment of P67 (0.20 g, 0.52 mmol) under the conditions listed for the preparation of example 90 yielded 80 mg (41% yield) of the title compound as a yellow solid. LC-MS: M+H=379.2.

Example 98

4-[[4-(Aminomethyl)phenyl]amino]-2-cyclohexyl-6-(4-methylphenyl)-5-pyrimidinol

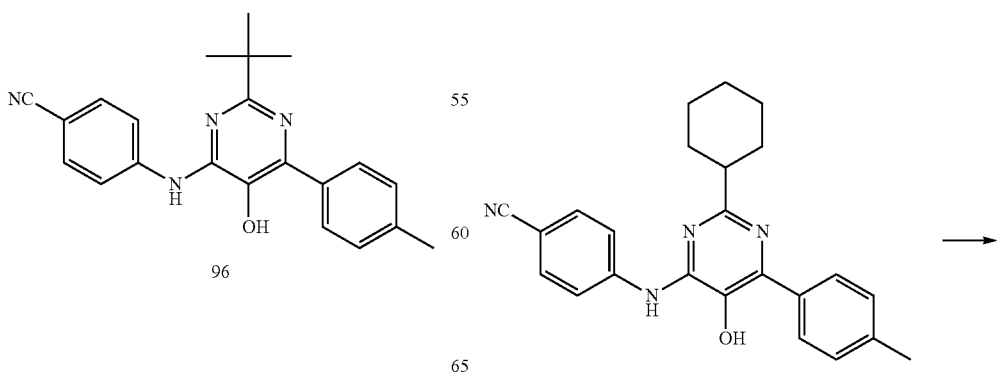

95

-continued

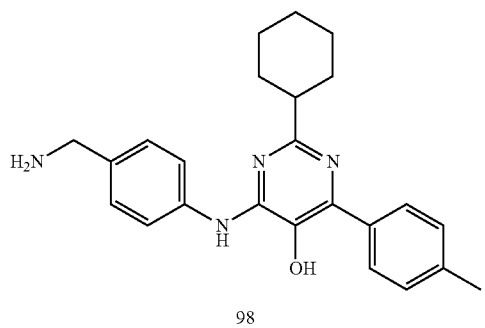

98

To a pressure bottle charged with 95 (0.10 g, 0.26 mmol) in 7M $NH_3$ in MeOH (5 mL) at rt was added 50% Raney Ni in $H_2O$ (~4 mL). The mixture was shaken under 50 psi of $H_2$ for 3 h and purged to $N_2$. The mixture was filtered thru a pad of CELITE which was generously washed with 7M $NH_3$ in MeOH (50 mL). The filtrate was concentrated under reduced pressure and was placed under high vacuum. The crude material was purified by reverse phase HPLC(C18 column: 95:5 $H_2O:CH_3CN$ (w/0.1% TFA) to 90:10 $CH_3CN:H_2O$) to afford 110 mg (70% yield) of light orange solid as the monohydrochloride salt after HCl treatment. LC-MS: M+H=285.2.

By essentially the same procedure set forth in Example 98, only substituting the precursor nitriles, the compounds in Table 5 were prepared:

TABLE 5

| Example | Precursor Nitrile (Ex.) | Product | cmpd 1) yield (%) 2) LC-MS (M + H) |
|---|---|---|---|
| 99 | (structure) | (structure) | 1) 99 2) 383.2 |
| 100 | (97) (structure) | (structure) | 1) 40 2) 363.2 |
| | (96) | | |

Examples 101-102

4-[[5-Hydroxy-6-(4-methylphenyl)-2-phenyl-4-pyrimidinyl]amino]benzamide (101)

4-[[5-Hydroxy-6-(4-methylphenyl)-2-phenyl-4-pyrimidinyl]amino]benzenecarboximidamide (102)

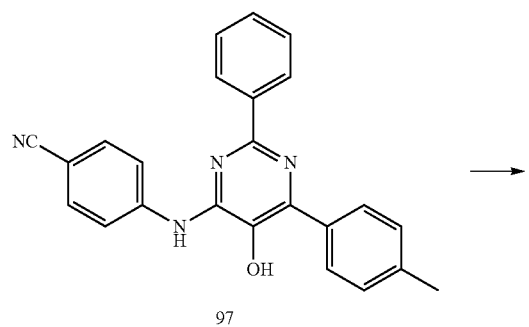

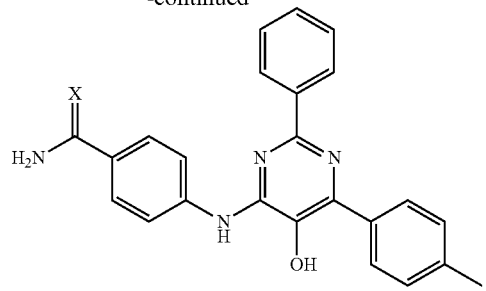

101: X = O
102: X = NH

To a pressure tube charged with 97 (50 mg, 0.07 mmol) in MeOH (2 mL) at 0° C. was added AcCl (2 mL) drop wise. The tube was purged to $N_2$, capped, and stirred at it for 12 h. The mixture was concentrated under reduced pressure and placed under high vacuum to remove trace volatiles. The crude imidate product was taken up in 7 M $NH_3$ in MeOH (10 mL), transferred to a pressure tube. The tube was capped and stirred for 72 h. The solution was concentrated under reduced pressure and the crude mixture was purified by reverse-phase HPLC to afford 3 mg (11% yield) of amide 101 (LC-MS=M+H=397) and 50 mg (87% yield) of amidine 102 as the monohydrochloride after HCl treatment (LC-MS=M+H(—HCl)=396.2).

By essentially the same procedure set forth in Examples 101-102 only substituting the precursor nitriles, the compounds in Table 6 were prepared:

TABLE 6

| Example | Precursor Nitrile (Ex.) | Product | cmpd 1) yield (%) 2) LC-MS (M + H) |
|---|---|---|---|
| 103 | (95) | | 1) 40 2) 402.2 |
| 104 | (95) | | 1) 5 2) 403.2 |

TABLE 6-continued

| Example | Precursor Nitrile (Ex.) | Product | cmpd 1) yield (%) 2) LC-MS (M + H) |
|---|---|---|---|
| 105 | (96) | | 1) 95 2) 376.2 |

Examples 106

4-(7-Isoquinolinylamino)-6-(4-methylphenyl)-5-pyrimidinol

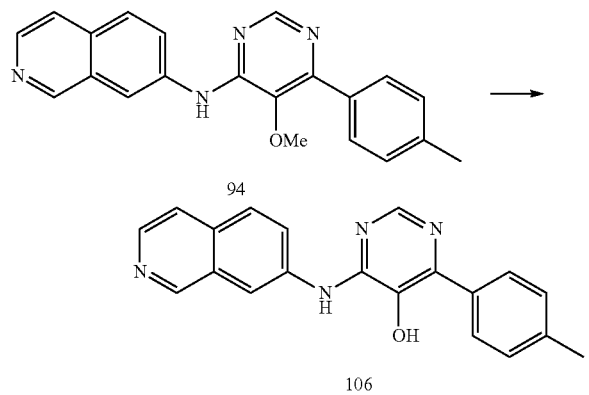

Treatment of 94 (0.20 g, 0.50 mmol) under the reaction conditions outlined for the preparation of Example 90 afforded 25 mg (16% yield) of the title compound as brown solid. LC-MS: M+H=329.2.

Example 107

2-(5-Hydroxy-6-p-tolylpyrimidin-4-yl)-1H-benzo[d]imidazole-5-carboximidamide

Step 1: Preparation of 5-hydroxy-6-p-tolylpyrimidine-4-carbonitrile P69

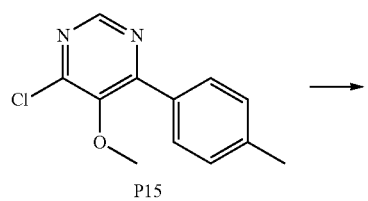

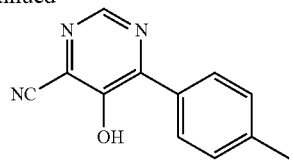

To a solution of 4-chloro-5-methoxy-6-p-tolylpyrimidine P5 (100 mg, 0.43 mmol) in DMF (2 mL) and NMP (0.5 mL) was added triethylenediamine (62 mg, 0.55 mmol) and potassium cyanide (55 mg, 0.85 mmol). The reaction mixture was stirred at room temperature for 18 hours. Dichloromethane and 1 N hydrochloric acid were added. The organic layer was dried over anhydrous sodium sulfate. The organic solvent was evaporated under reduced pressure. The crude product was purified by flash column chromatography to afford the desired 5-hydroxy-6-p-tolylpyrimidine-4-carbonitrile P69 (70 mg, 0.33 mmol).

Step 2: Preparation of 5-hydroxy-6-p-tolylpyrimidine-4-carboxylic acid P70

To 5-hydroxy-6-p-tolylpyrimidine-4-carbonitrile P69 (360 mg, 1.71 mmol) was added water (20 mL) and concentrated sulfuric acid (20 mL). The reaction mixture was heated under reflux for 4 hours. The reaction mixture was poured onto ice. The precipitate was filtered and washed with water. The solid product was dried under reduced pressure to afford the desired 5-hydroxy-6-p-tolylpyrimidine-4-carboxylic acid P70 (210 mg, 0.91 mmol).

Step 3: Preparation of benzyl 5-(benzyloxy)-6-p-tolylpyrimidine-4-carboxylate P71

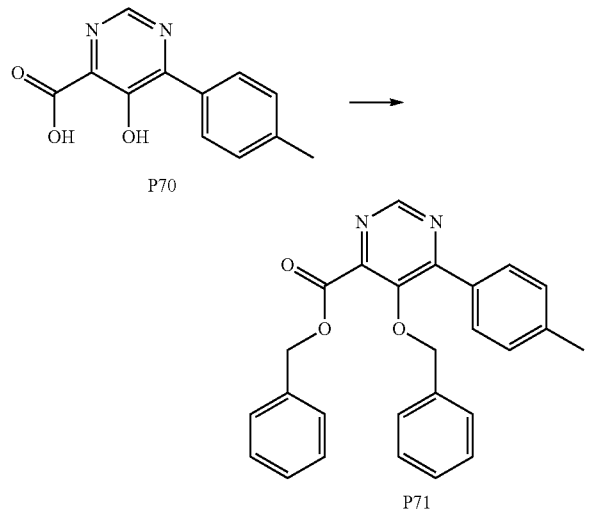

To a solution of 5-hydroxy-6-p-tolylpyrimidine-4-carboxylic acid P70 (40 mg, 0.17 mmol) in anhydrous DMF (2 mL) was add potassium tert-butoxide (39 mg, 0.35 mmol) and benzyl bromide (44 mg, 0.26 mmol). The reaction mixture was stirred at room temperature for 18 hours. Organic solvent was evaporated under reduced pressure. Ethyl acetate and 1 N hydrochloric acid were added. The organic layer was washed with saturated brine and dried over anhydrous sodium sulfate. The organic solvent was evaporated under reduced pressure. The crude product was purified by flash column chromatography to afford the desired benzyl 5-(benzyloxy)-6-p-tolylpyrimidine-4-carboxylate P71 (50 mg, 0.12 mmol).

Step 4: Preparation of 5-(benzyloxy)-6-p-tolylpyrimidine-4-carboxylic acid P72

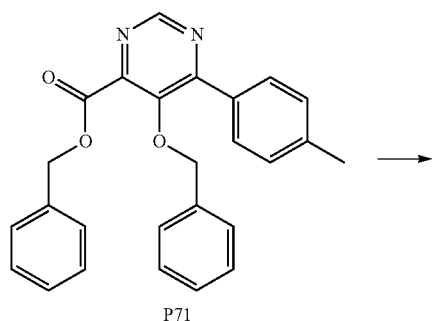

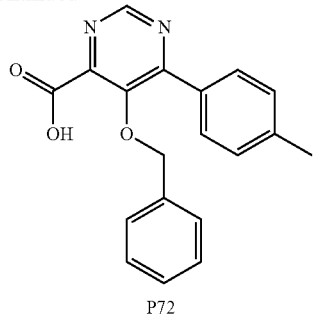

To a solution of benzyl 5-(benzyloxy)-6-p-tolylpyrimidine-4-carboxylate P71 (90 mg, 0.22 mmol) in methanol (5 mL) was added lithium hydroxide monohydrate (46 mg, 1.10 mmol). The reaction mixture was heated in a microwave reactor at 90° C. for 10 minutes. The organic solvent was evaporated under reduced pressure. Ethyl acetate and 1 N hydrochloric acid were added. The organic layer was washed with water and saturated brine. The organic layer was dried over anhydrous sodium sulfate. The organic solvent was evaporated under reduced pressure. The solid product was dried under reduced pressure to afford the desired 5-(benzyloxy)-6-p-tolylpyrimidine-4-carboxylic acid P72 (70 mg, 0.22 mmol).

Step 5: Preparation of 2-(5-hydroxy-6-p-tolylpyrimidin-4-yl)-1H-benzo[d]imidazole-5-carbonitrile P73

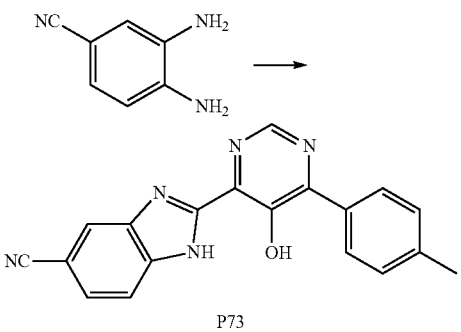

To a solution of 5-(benzyloxy)-6-p-tolylpyrimidine-4-carboxylic acid P72 (80 mg, 0.25 mmol) in DMF (3 mL) was added 3,4-diaminobenzonitrile (40 mg, 0.30 mmol), HATU (124 mg, 0.33 mmol) and diisopropylethylamine (48 mg, 0.37 mmol). The reaction mixture was stirred at room temperature for 18 hours. The organic solvent was evaporated under reduced pressure. Ethyl acetate and 1 N hydrochloric acid were added. The organic layer was washed with water and saturated brine. The organic layer was dried over anhydrous sodium sulfate. The organic solvent was evaporated under reduced pressure. The intermediate was purified by flash column chromatography. The intermediate was dissolved in acetic acid (5 mL) and heated in a microwave reactor at 160° C. for 1 hour. The organic solvent was evaporated under reduced pressure. Trifluoroacetic acid (5 mL) was added and the solution was heated in a microwave reactor at 120° C. for 30 minutes. The organic solvent was evaporated under reduced pressure. The crude product was purified by RP-HPLC to afford the desired 2-(5-hydroxy-6-p-tolylpyrimidin-4-yl)-1H-benzo[d]imidazole-5-carbonitrile P73 (16 mg, 0.049 mmol).

Step 6: Preparation of 2-(5-hydroxy-6-p-tolylpyrimidin-4-yl)-1H-benzo[d]imidazole-5-carboximidamide P74

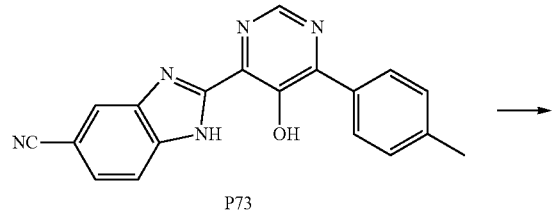

P73

→

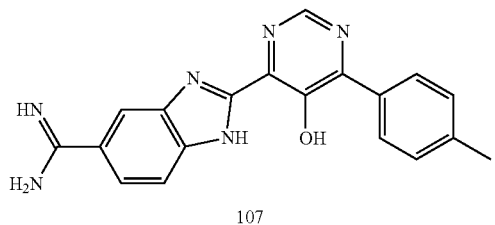

107

To a solution of 2-(5-hydroxy-6-p-tolylpyrimidin-4-yl)-1H-benzo[d]imidazole-5-carbonitrile P73 (16 mg, 0.049 mmol) in absolute ethanol (2 mL) cooled in an ice bath was added acetyl chloride (2 mL). The reaction mixture was stirred at room temperature for 18 hours. The organic solvent was evaporated under reduced pressure. A methanolic ammonia solution (7 N, 5 mL) was added to the intermediate. The reaction mixture was stirred at room temperature for 18 hours. The organic solvent was evaporated under reduced pressure. The crude product was purified by RP-HPLC to afford the desired 2-(5-hydroxy-6-p-tolylpyrimidin-4-yl)-1H-benzo[d]imidazole-5-carboximidamide 107 (3 mg, 0.0087 mmol).

LCMS: 345 (MH$^+$)

Example 108

2-(5-hydroxy-6-phenyl-4-pyrimidinyl)-1h-benzimidazole-6-carboximidamide

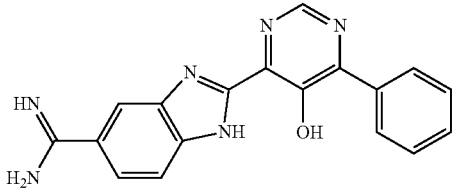

108

Example 107 was prepared using a procedure similar to the preparation of 106.

LSMS: 331 (MH$^+$)

The following compounds were synthesized using analogous procedures from the appropriate starting material.

UTILITY

The compounds of this invention are inhibitors of factor IXa and are useful as anticoagulants for the treatment or prevention of thromboembolic disorders in mammals (i.e., factor IXa-associated disorders). In general, a thromboembolic disorder is a circulatory disease caused by blood clots (i.e., diseases involving fibrin formation, platelet activation, and/or platelet aggregation).

The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors:

factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory dystress syndrome, hereditary angioedema or other inherited or acquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations can be made in 50 mM HEPES buffer at pH 7.4 containing 145 mM NaCl, 5 mM KCl, and 0.1% PEG 8000 (polyethylene glycol; JT Baker or Fisher Scientific). Determinations can be made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. Compounds tested in the Factor XIa assay are considered to be active if they exhibit a K, of equal to or less than 15 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM.

Factor VIIa determinations can be made in 0.005 M calcium chloride, 0.15 M sodium chloride, 0.05 M HEPES buffer containing 0.5% PEG 8000 at a pH of 7.4. Determinations can be made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-11e-Pro-Arg-pNA (S-2288; Chromogenix or BMPM-2; AnaSpec) at a concentration of 0.001 M. Compounds tested in the Factor VIIa assay are considered to be active if they exhibit a $K_i$ of equal to or less than 15 µM.

Factor IXa determinations were made according to the following assay procedure:
Buffer:
50 mM Tris pH 8.0
5 mM $CaCl_2.2H_2O$
100 mM NaCl
15% vol/vol Ethylene Glycol
Enzyme:
Human plasma factor IXa. (American Diagnostica Inc. product)
Enzyme is diluted 1:800 in buffer to achieve 0.0057 ug/ml working stock for use in assay. Mix by inversion.
Substrate:
Spectrozyme factor IXa Fluorogenic substrate (American Diagnostica Inc.)
The substrate (10 umoles lyophilized) is reconstituted with 1 ml water to give a 10 mM stock. The substrate is then further diluted to 300 uM in buffer for use in assay. Mix by inversion.
Procedure in 384 Well Plate:
Add 10 ul vehicle or compound
Add 10 ul Factor IXa enzyme.
    Add 10 ul Fluorogenic substrate.
Incubate reaction at room temperature for 2 h.
Quench with 5 ul 50% acetic acid.
Read Fluorescence—Absorbance 360 nm; Emission 440 nm
    Factor Xa determinations are made according to the following assay procedure:
Buffer:
20 mM Tris pH 8.0
2.5 mM $CaCl_2.2H_2O$
200 mM NaCl
Enzyme:
Human plasma factor Xa. (American Diagnostica Inc.)
Resuspend enzyme in water to 80 ug/ml.
Enzyme is diluted to 0.133 ug/ml in buffer. Mix by inversion.
Substrate:
Spectrozyme factor IXa Fluorogenic substrate (American Diagnostica Inc.)
Reconstitute with 1 ml water to give a 10 mM stock. The substrate is then further diluted to 300 uM in buffer for use in assay. Mix by inversion.
Procedure in 384 Well Plate:
Add 10 ul vehicle or compound
Add 10 ul Factor Xa enzyme.
Add 10 ul Fluorogenic substrate.
Incubate reaction at room temperature for 2 h.
Quench with 5 ul 50% acetic acid.
Read Fluorescence—Absorbance 360 nm; Emission 440 nm
    IC50 determinations for factor IXa and Xa were made for the present compounds as described below
IC50 Calculation
Compounds were tested at multiple concentrations beginning at 100 uM and decreasing at half log intervals. IC50 values for compounds at each coagulation factor were then generated using nonlinear curvefit software within ActivityBase (IDBS software). Each compound that was tested was tested in at least 2 separate assays (4 replicates per experiment). The final IC50 values obtained represent the average of all determinations.

In one embodiment, the compounds of the present invention have factor IXa $IC_{50}$ (nM; nanomolar) values ranging from about 10 nM to greater than 25,000 nM. In another embodiment, for some of the compounds, the values range from about 10 nM to about 20,000 nM, and in another embodiment from about 20 nM to about 10,000 nM, and in another embodiment from about 20 nM to about 1000 M, and in another embodiment from about 20 nM to about 500 nM, and in another embodiment from about 20 nM to about 100 nM, and in another embodiment from about 5 nM to about 100 nM.

In one embodiment, some of the compounds of the present invention are selective factor IXa inhibitors, i.e., selective for factor IXa over other coagulation factors, such as factor Xa.

Selectivity Calculation

Selectivity for Factor IXa activity over Factor Xa activity can be determined by the following calculation: (IC50 Factor Xa)/(1050 Factor IXa). Similar calculations can be made for selectivity of compounds for Factor IX compared to other coagulation factors.

Plasma kallikrein determinations can be made in 0.1 M sodium phosphate buffer at a pH of 7.4 containing 0.2 M sodium chloride and 0.5% PEG 8000. Determinations can be made using purified human kallikrein (Enzyme Research Laboratories) at a final assay concentration of 200 µM and the synthetic substrate S-2302 (H-(D)-Pro-Phe-Arg-pNA; Chromogenix) at a concentration of 0.00008-0.0004 M. The Km value useful for calculation of $K_i$ is 0.00005 to 0.00007 M. Compounds tested in the plasma kallikrein assay are considered to be active if they exhibit a $K_i$ of equal to or less than 15 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM.

Thrombin determinations can be made in 0.1 M sodium phosphate buffer at a pH of 7.4 containing 0.2 M sodium chloride and 0.5% PEG 8000. Determinations are made using purified human alpha thrombin (Haematologic Technologies or Enzyme Research Laboratories) at a final assay concentration of 200-250 µM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 15 µM.

Compounds of the present invention are useful as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease can be determined at 25° C. using the method of Lineweaver and Burk. Values of $K_i$ are determined by allowing the protease to react with the substrate in the presence of the inhibitor. Reactions are allowed to go for periods of 20-180 minutes (depending on the protease) and the velocities (rate of absorbance or fluorescence change versus time) are measured. The following relationships were used to calculate K; values:

$(v_o - v_s)/v_s = I/(K_i(1+S/K_m))$ for a competitive inhibitor with one binding site; or $v_s/v_o = A + ((B-A)/1 + ((IC_{50}/(I)^n)))$ and
$K_i = IC_{50}/(1+S/K_m)$ for a competitive inhibitor
where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model: The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model: The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANOX®), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art. Factor IXa inhibitors different from the compounds of Formulae I-III include monoclonal antibodies, synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulents. *Arterioscler Thromb Vasc Biol.* 2007; 27: 722-727.)

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, J. Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and WO 01/96330 and 10/271,715.

Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamili nifedipine, amlodipine and mybef radii); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor IXa in serum samples could be determined by careful titration of protease activity in the presence of the relevant chromogenic substrate, S2366, with a potent and selective Factor IXa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to Covera bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound of Formula (I)

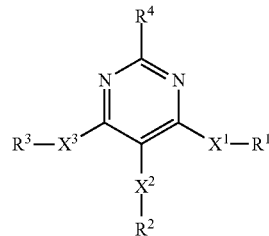

Formula (I)

or a pharmaceutically acceptable salt or solvate thereof, wherein:

$X^1$ is a covalent bond;

$R^1$ is substituted aryl, wherein when said substituted aryl has substituents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substituents on adjacent carbon atoms, said substituents can optionally be taken together with the carbon atoms to which they are attached to form a second five- or six-membered cycloalkyl, heterocyclyl, aryl or heteroaryl;

$X^2$ is —O—;

$R^2$ is H;

$X^3$ is —NH—;

$R^3$ is selected from the group consisting of substituted aryl, substituted heteroaryl, or isoquinoline wherein when each of said substituted aryl, substituted heteroaryl, or isoquinoline has substituents on adjacent carbon atoms, said substituents can optionally be taken together with the carbon atoms to which they are attached to form a first five- or six-membered cycloalkyl, heterocyclyl, aryl or heteroaryl, wherein when said first five- or six-membered cycloalkyl, heterocyclyl, aryl or heteroaryl has substituents on adjacent carbon atoms, said substituents can optionally be taken together with the carbon atoms to which they are attached to form a second five- or six-membered cycloalkyl, heterocyclyl, aryl or heteroaryl; and $R^4$ is selected from the group consisting of H alkyl, cycloalkyl, heterocyclyl, aryl and heteroaryl.

2. The compound of claim 1, wherein $R^3$ is alkyl which is unsubstituted or substituted with an aryl substituent, wherein when said aryl has substitutents on adjacent carbon atoms, said substituents can optionally be taken together with the carbon atoms to which they are attached to form a five- or six-membered aryl or heteroaryl.

3. The compound of claim 2, wherein $R^3$ is alkyl-benzopyridyl, wherein the benzopyridyl is attached to the alkyl through the benzene ring of said benzopyridyl, wherein said benzopyridyl is unsubstituted or substituted with a ring system substitutent that is —NH$_2$.

4. The compound of claim 1, wherein $R^3$ is aryl, wherein when said aryl has substitutents on adjacent carbon atoms, said substituents can optionally be taken together with the carbon atoms to which they are attached to form a five- or six-membered cyclohexyl, aryl, or heteroaryl.

5. The compound of claim 4, wherein said $R^3$ aryl is selected from the group consisting of phenyl,

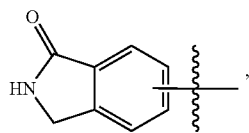

isoindolinyl, benzoimidazolyl, benzoxazolyl, benzopyrrolyl, benzopyrrazolyl,

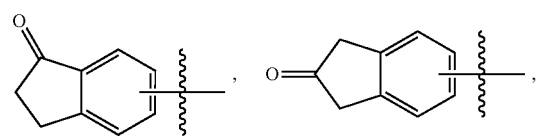

benzopyridyl,

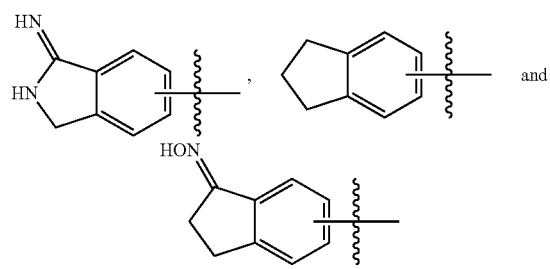

each of which is independently unsubstituted or substituted with at least one ring system substituent selected from the group consisting of alkyl, aminoalkyl, —NH$_2$, —C(=NH)NH$_2$, cyano, halo, —C(=O)O-alkyl, alkoxy, haloalkoxy, heteroaryl, hydroxyl, and —C(=O)NH$_2$, and wherein

indicates the point of attachment of the $R^3$ aryl.

6. The compound of claim 1, wherein $R^3$ is substituted heteroaryl, wherein when said substituted heteroaryl has substituents on adjacent carbon atoms, said substituents can optionally be taken together with the carbon atoms to which they are attached to form a five- or six-membered aryl or heteroaryl.

7. The compound of claim 6, wherein said $R^3$ heteroaryl is selected benzopyrrolidinyl which is unsubstituted or substituted with at least one ring system substituent selected from the group consisting of cyano, alkyl, and aminoalkyl-.

8. The compound of claim 1, wherein $R^4$ is alkyl and is t-butyl.

9. The compound of claim 1, wherein $R^4$ is cycloalkyl and is selected from the group consisting of cyclopropyl and cyclohexyl.

10. The compound of claim 1, wherein $R^4$ is aryl and is phenyl.

11. The compound of claim 1, selected from the group consisting of:

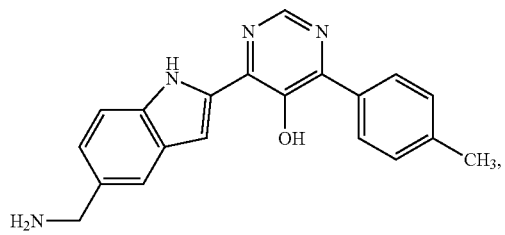

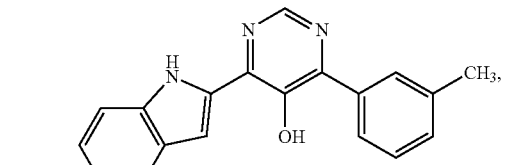

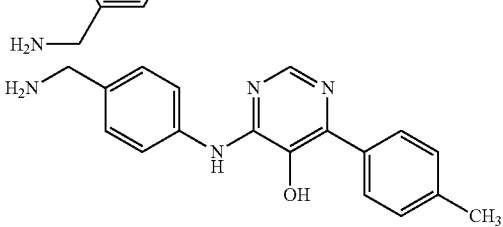

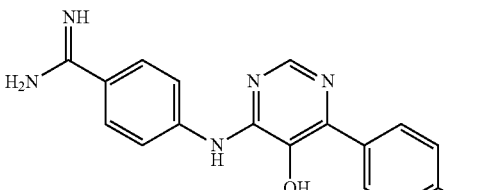

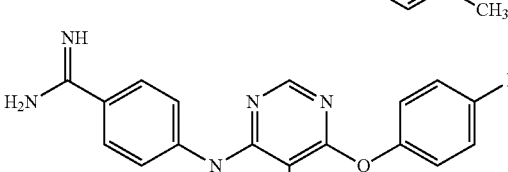

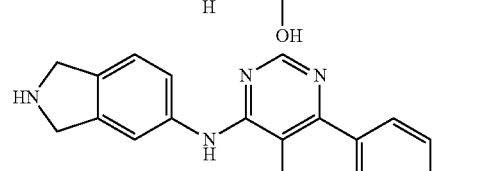

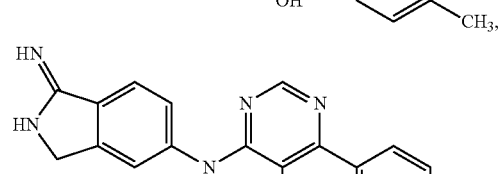

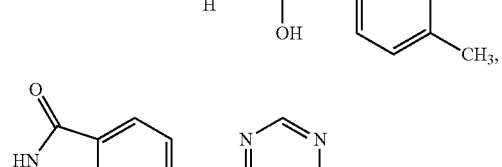

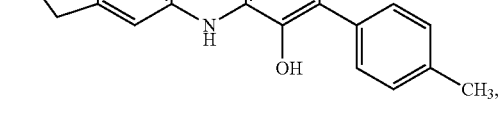

129
-continued
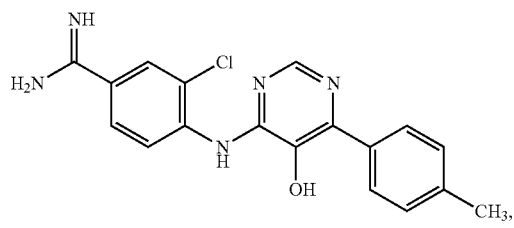
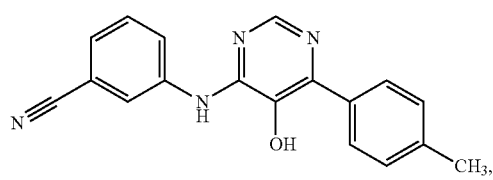
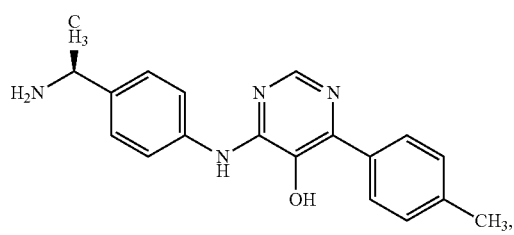
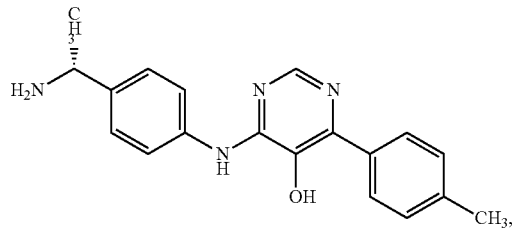
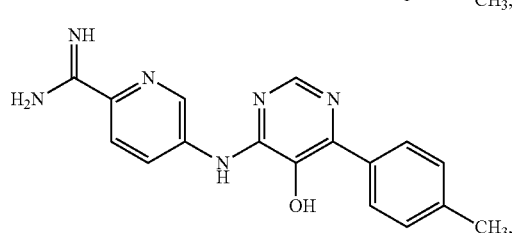
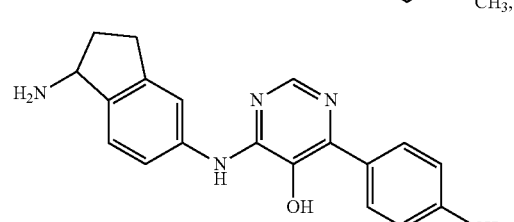
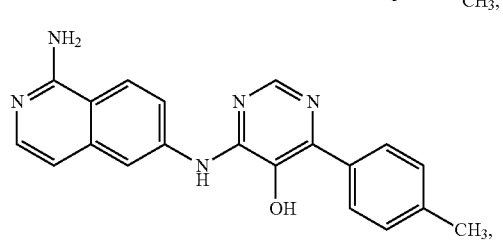
130
-continued
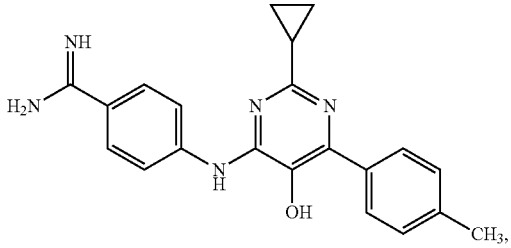
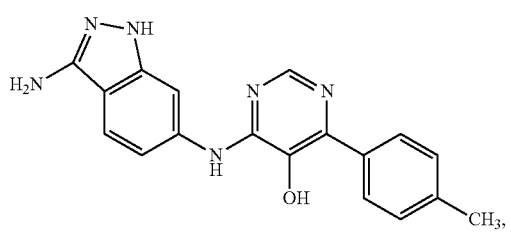
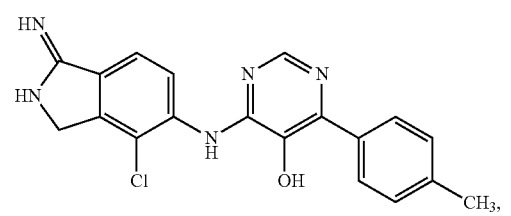
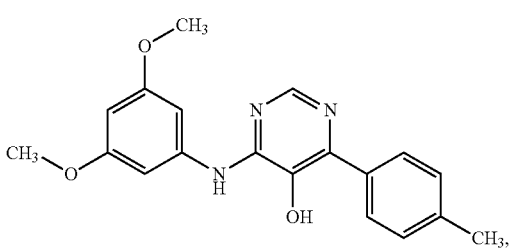
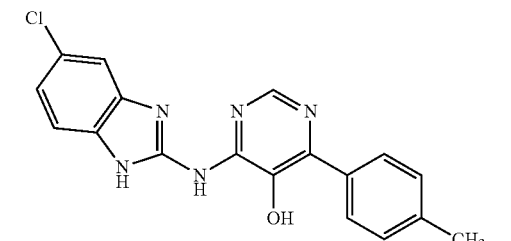
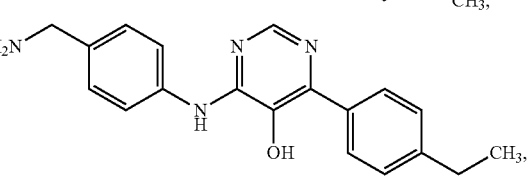
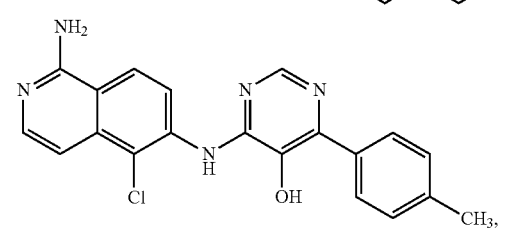

131
-continued
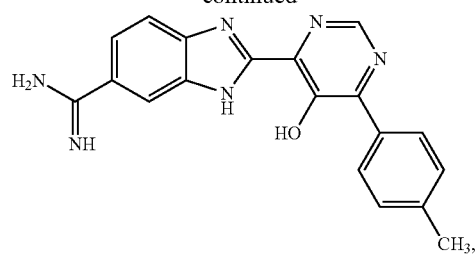
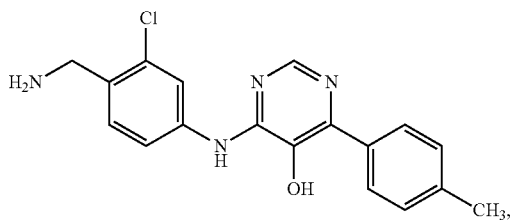
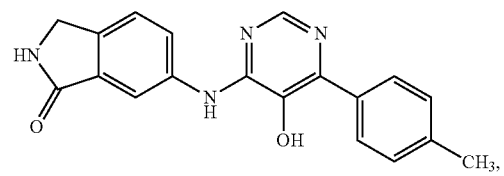
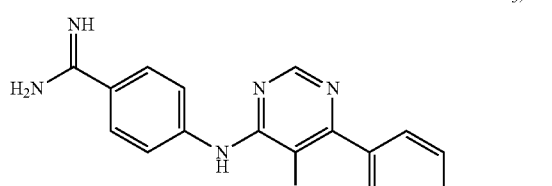
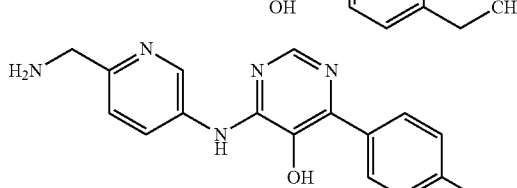
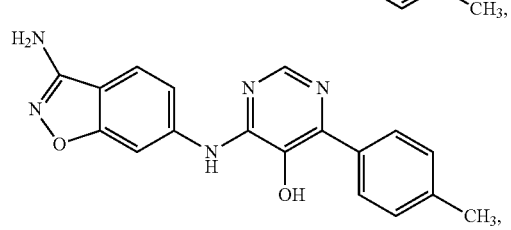
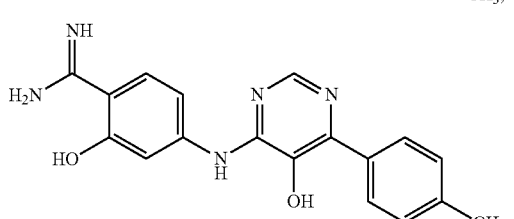
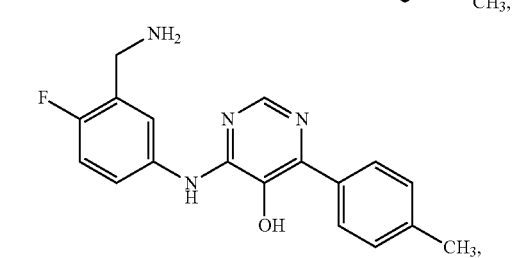
132
-continued
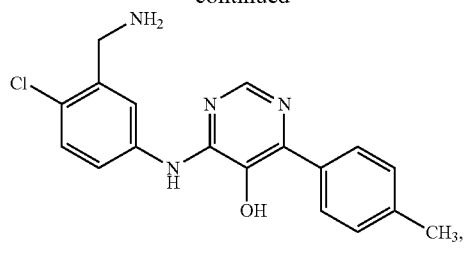
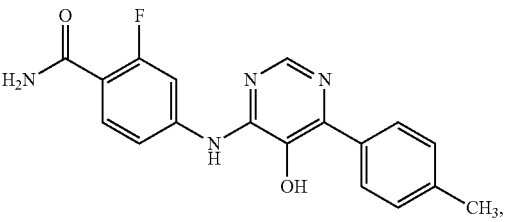
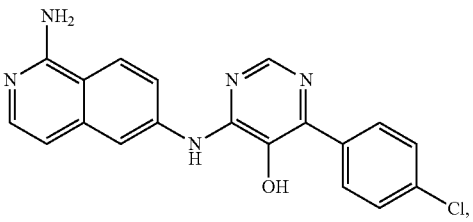
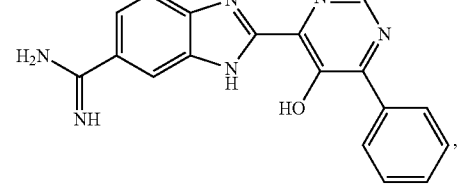
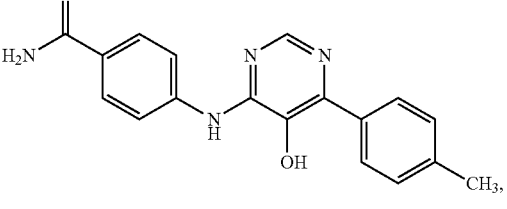
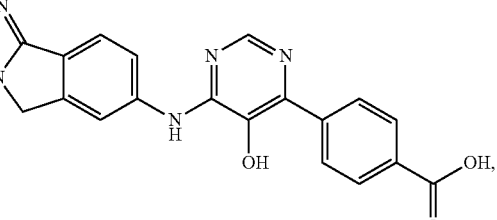
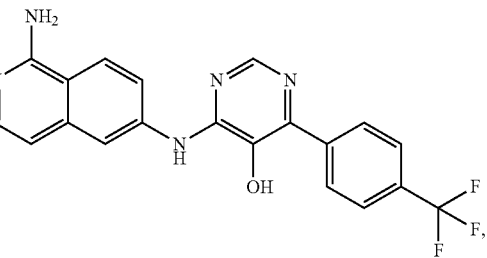

133
-continued
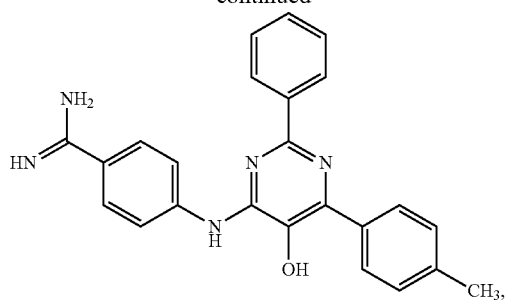
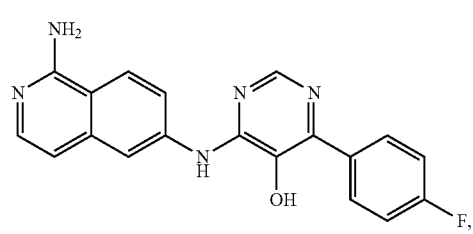
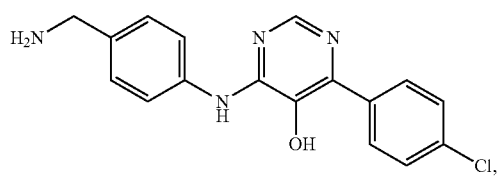
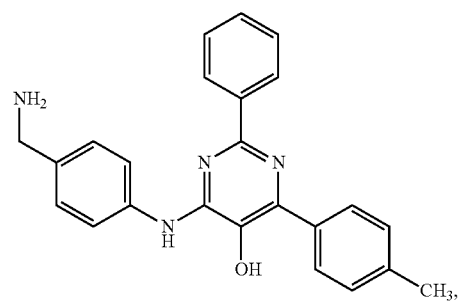
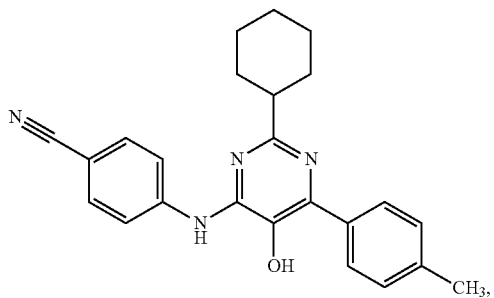
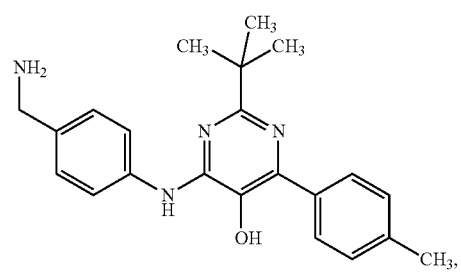
134
-continued
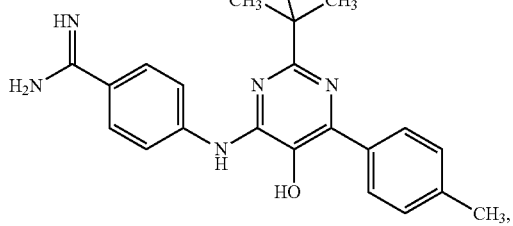
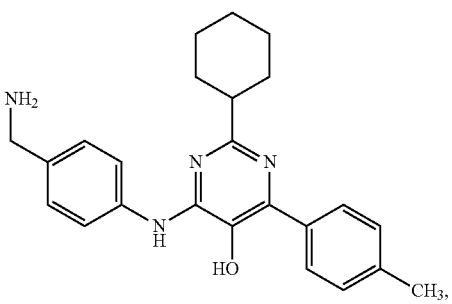
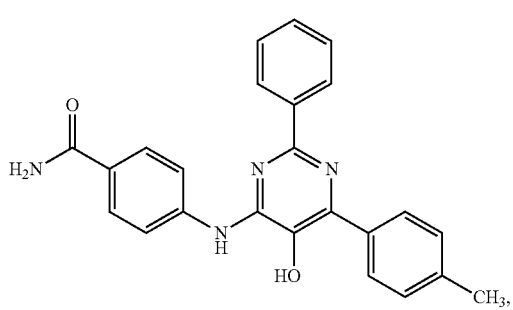
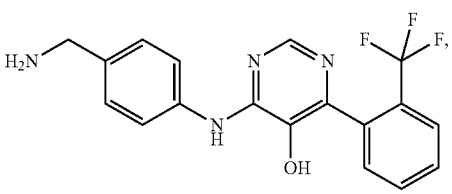
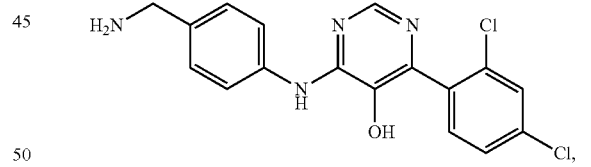
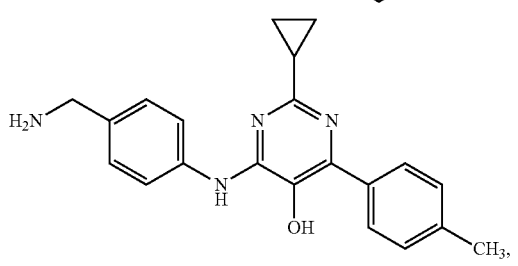

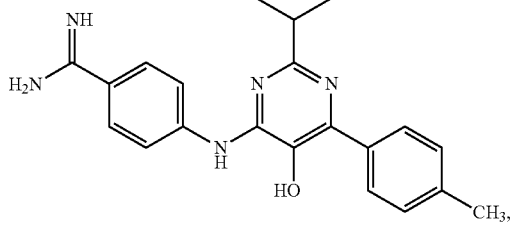
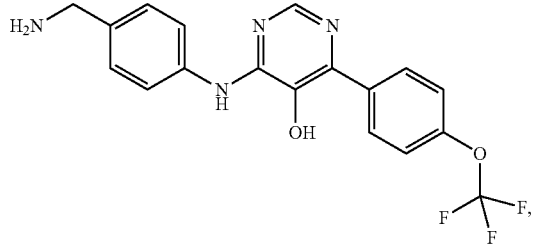
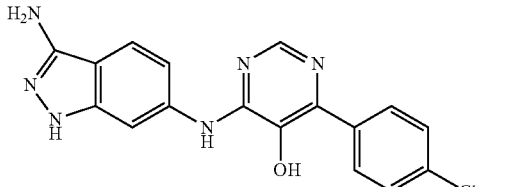
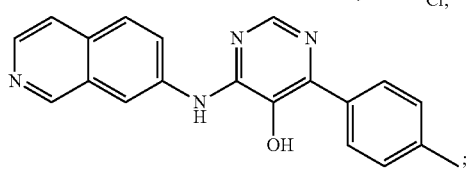
or a pharmaceutically acceptable salt or solvate thereof.
12. A pharmaceutical composition comprising at least one compound of claim 1, or a pharmaceutically acceptable salt, and at least one pharmaceutically acceptable carrier.
* * * * *